United States Patent
Ohlfest et al.

(10) Patent No.: US 9,624,303 B2
(45) Date of Patent: Apr. 18, 2017

(54) SINGLE-CHAIN VARIABLE FRAGMENT ANTI-CD133 ANTIBODIES AND USES THEREOF

(71) Applicant: REGENTS OF THE UNIVERSITY OF MINNESOTA, Minneapolis, MN (US)

(72) Inventors: John R. Ohlfest, Minneapolis, MN (US); Jayanth Panyam, Plymouth, MN (US); Suresh Kumar Swaminathan, Minneapolis, MN (US); Daniel A. Vallera, St. Louis Park, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/990,501

(22) Filed: Jan. 7, 2016

(65) Prior Publication Data
US 2016/0215058 A1    Jul. 28, 2016

Related U.S. Application Data

(62) Division of application No. 13/699,944, filed as application No. PCT/US2010/059827 on Dec. 10, 2010, now Pat. No. 9,249,225.

(60) Provisional application No. 61/348,348, filed on May 26, 2010, provisional application No. 61/390,011, filed on Oct. 5, 2010.

(51) Int. Cl.
*C07K 16/28* (2006.01)
*A61K 39/00* (2006.01)
*C07K 16/30* (2006.01)

(52) U.S. Cl.
CPC ...... *C07K 16/2896* (2013.01); *C07K 16/2863* (2013.01); *C07K 16/30* (2013.01); *C07K 16/303* (2013.01); *C07K 16/3015* (2013.01); *C07K 16/3046* (2013.01); *A61K 2039/505* (2013.01); *A61K 2039/507* (2013.01); *C07K 2317/622* (2013.01); *C07K 2317/73* (2013.01); *C07K 2319/42* (2013.01); *C07K 2319/55* (2013.01); *G01N 2333/70596* (2013.01)

(58) Field of Classification Search
None
See application file for complete search history.

(56) References Cited

U.S. PATENT DOCUMENTS

| 5,843,633 A | 12/1998 | Yin et al. |
| 6,455,678 B1 | 9/2002 | Yin et al. |
| 7,608,259 B2 | 10/2009 | Bergstein |
| 2006/0083682 A1 | 4/2006 | Bergstein |
| 2008/0118432 A1 | 5/2008 | Bergstein et al. |
| 2008/0118518 A1 | 5/2008 | Cirrito et al. |

FOREIGN PATENT DOCUMENTS

| WO | WO 2008/030538 A2 | 3/2008 |
| WO | WO 2008/030616 A2 | 3/2008 |
| WO | WO 2008/030617 A2 | 3/2008 |
| WO | WO 2008/127735 A1 | 10/2008 |
| WO | WO 2009/102493 A2 | 8/2009 |
| WO | WO 2009/102493 A3 | 8/2009 |

OTHER PUBLICATIONS

Asselin-Labat et al., "Steroid hormone receptor status of mouse mammary stem cells," *J. Natl. Cancer Inst.*, Jul. 2006; 98(14):1011-1014.
Barbas et al., *Phage Display: A laboratory manual*, Cold Spring Harbor Laboratory Press, Cold Spring Harbor, NY, 2001.
Bidlingmaier et al., "The utility and limitations of glycosylated human CD133 epitopes in defining cancer stem cells," *J. Mol. Med. (Berl).*, Sep. 2008; 86(9):1025-32. Available online Jun. 6, 2008.
Cerqueira et al., "Understanding ribonucleotide reductase inactivation by gemcitabine," *Eur. J. Chem.*, Oct. 2007; 13(30):8507-8515. Available online Jul. 18, 2007.
Dalerba et al., "Phenotypic characterization of human colorectal cancer stem cells," *PNAS USA*, Jun. 2007; 104(24):10158-10163.
Evangelista et al., "The hedgehog signaling pathway in cancer," *Clin. Cancer. Res.*, Oct. 2006; 12(20):5924-5928.
Holliger et al., "Engineered antibody fragments and the rise of single domains," *Nature Biotechnology*, 2006, 23:1126-1136.
International Preliminary Report on Patentability, issued Nov. 27, 2012, International Application No. PCT/US2010/059827, filed Dec. 10, 2010; 10 pgs.
International Search Report, mailed May 11, 2011, International Application No. PCT/US2010/059827, filed Dec. 10, 2010; 6 pgs.
Jemal et al., "Cancer Statistics, 2006," *CA Cancer J. Clin.*, Mar./Apr. 2006; 56(2):106-130. Available online Feb. 2009.
Kawamura et al., "Induction of Antiidiotypic Antibodies by Donor-Specific Blood Transfusions: Establishment of a Human-Mouse Hybridoma Secreting the MLR-Inhibiting Factor," *Transplantation*, Sep. 1989; 48(3):459-463.
Kemper et al., "The AC133 epitope, but not the CD133 protein, is lost upon cancer stem cell differentiation," *Cancer Res.*, Jan. 15, 2010; 70(2):719-29. Available online Jan. 12, 2010.
Lehle et al., "The specific site of tunicamycin inhibition in the formation of dolichol-bound N-acetylglucosamine derivatives," *FEBS Lett*, Nov. 15, 1976; 72(1):167-70.
Liao et al., "Enrichment of a population of mammary gland cells that form mammospheres and have in vivo repopulating activity," *Cancer Res.*, Sep. 2007; 67(17):8131-8138.
Mimeault et al., "Cytotoxic Effects Induced by Docetaxel, Gefitinib, and Cyclopamine on Side Population and Nonside Population Cell Fractions from Human Invasive Prostate Cancer Cells," *Mol. Cancer Ther.*, Mar. 2010; 9(3):617-630. Available online Feb. 23, 2010.
Naor et al., "CD44 in Cancer," *Crit. Rev. Clin. Lab. Sci.*, Jan. 2002; 39(6):527579.

(Continued)

*Primary Examiner* — Julie Wu
(74) *Attorney, Agent, or Firm* — Mueting, Raasch & Gebhardt, PA

(57) ABSTRACT

Disclosed herein are a monoclonal antibody that specifically binds to human CD133 and single-chain variable fragments thereof. Also disclosed herein is a hybridoma that produces the monoclonal antibody that specifically binds to human CD133.

3 Claims, 18 Drawing Sheets

(56) References Cited

OTHER PUBLICATIONS

National Center for Biotechnology Information, GenBank Locus NM_006017, Accession No. NM_006017, "*Homo sapiens* prominin 1 (PROM1), transcript variant 1, mRNA." [online]. Bethesda, MD [retrieved on Jan. 16, 2014]. Retrieved from the internet; http://www.ncbi.nlm.nih.gov/nuccore/NM_006017.2; 6pgs.
Neuzil et al., "Tumour-initiating cells vs. cancer 'stem' cells and CD133: What's in the name?" *Biochem. Biophys. Res. Commun.*, Apr. 2007; 355(4):855-859.
O'Brien et al., "Broadening the impact of antibody phage display technology. Amplification of immunoglobulin sequences from species other than humans or mice," *Methods Mol. Biol.*, 2002; 178:73-86.
Oettle et al., "Adjuvant chemotherapy with gemcitabine vs observation in patients undergoing curative-intent resection of pancreatic cancer: a randomized controlled trial," *JAMA*, Jan. 2007; 297(3):267-277.
Oh et al., "A Novel Reduced Immunogenicity Bispecific Targeted Toxin Simultaneously Recognizing Human Epidermal Growth Factor and Interleukin-4 Receptors in a Mouse Model of Metastatic Breast Carcinoma," *Clin. Cancer Res.*, Oct. 1, 2009; 15(19):6137-6147.
Ohlfest et al., "Immunotxoin targeting CD133+ breast carcinoma cells," *Drug Delivery and Translational Research*, Apr. 2013; 3(2):195-204. Available online May 2, 2012.
Onda et al., "An immunotoxin with greatly reduced immunogenicity by identification and removal of B cell epitopes," *Proc . Natl. Acad. Sci. U.S.A.*, Aug. 12, 2008; 105(32):11311-11316. Available online Aug. 4, 2008.
Orian-Rousseau, "CD44, a therapeutic target for metastasising tumours," *Eur. J. Cancer*, May 2010; 46(7):1271-1277. Available online Mar. 22, 2010.
Osmond et al., "Glioblastoma cells negative for the anti-CD133 antibody AC133 express a truncated variant of the CD133 protein," *Int. J. Mol. Med.*, Jun. 2010; 25(6):883-888. Available online Jun. 1, 2010.
Pavlinkova et al., "Effects of humanization and gene shuffling on immunogenicity and antigen binding of anti-TAG-72 single chain FVs," *Int. J. Cancer*, Dec. 2001; 94(5):717-726.
Rappa et al., "The Stem Cell-Associated Antigen CD133 (Prominin-1) is a Molecular Therapeutic Target for Metastatic Melanoma," *Stem Cells*, Dec. 2008; 26(12):3008-3017. Available online Sep. 18, 2008.
Rosok et al., "A combinatorial library strategy for the rapid humanization of anticarcinoma BR96 Fab.," *J. Biol. Chem*, Sep. 1996; 271(37):22611-22618.
Shimamura et al., "Interleukin-4 cytotoxin therapy synergizes with gemcitabine in a mouse model of pancreatic ductal adenocarcinoma," *Cancer Res.*, Oct. 2007; 67(20):9903-9912.
Shipitsin et al., "Molecular definition of breast tumor heterogeneity," *Cancer Cell*, Mar. 2007; 11(3):259-273.
Shmelkov et al., "AC133/CD133/Prominin-1," *Int. J. Biochem. Cell Biol.*, Apr. 2005; 37(4):715-9.
Sidhu, *Phage Display in Biotechnology and Drug Discovery*, CRC Press/Taylor & Francis Group, Boca Raton, FL; 2005.
Skubitz et al., "Targeting CD133 in an in vivo ovarian cancer model reduces ovarian cancer progression," *Gynecologic Oncology*, 2013; 130(2013):579-587. Available online May 27, 2013.
Sleeman et al., "CD24 staining of mouse mammary gland cells defines luminal epithelial, myoepithelial/basal and non-epithelial cells," *Breast Cancer Res*, 2006; 8(1):R7, 6 pgs. Available online Dec. 12, 2005.
Smith et al., "CD133/prominin-1 is a potential therapeutic target for anti-body drug conjugates in hepatocellular and gastric cancers," *British Journal of Cancer*, Jul. 2008; 99(1):100-109. Available online Jun. 10, 2008.
Stish et al., "Design and modification of EGF4KDEL 7Mut, a novel bispecific ligand-directed toxin, with decreased immunogenicity and potent anti-mesothelioma activity," *British Journal of Cancer*, 2009; 101:114-1123.
Swaminathan et al., "Identification of a novel monoclonal antibody recognizing CD133," *J. Immunol. Methods*, Sep. 2010; 361:110-115. Available online Jul. 30, 2010.
Swaminathan et al., "Identification and characterization of a novel scFv recognizing human and mouse CD133," *Drug Delivery and Translational Research*, Apr. 2013, 3(2):143-151.
Tatusova et al., "BLAST 2 Sequences, a new tool for comparing protein and nucleotide sequences," *FEMS Microbiology Letters*, 1999, May; 174(2):247-250.
Tkacz et al., "Tunicamycin inhibition of polyisoprenyl N-acetylglucosaminyl pyrophosphate formation in calf-liver microsomes," *Biochem. Biophys Res. Commun.*, Jul. 8, 1975; 65(1):248-257.
Vallera et al., "Bioengineering a unique deimmunized bispecific targeted toxin that simultaneously recognizes human CD22 and CD19 receptors in a mouse model of B-cell metastases," *Mol Cancer Ther.*, Jun. 2010; 9(6):1872-83. Available online Jun. 8, 2010.
Von Der Maase et al., "Gemcitabine and cisplatin versus methotrexate, vinblastine, doxorubicin, and cisplatin in advanced or metastatic bladder cancer: results of a large, randomized, multinational, multicenter, phase III study," *J. Clin. Oncol.*, Sep. 2000; 18(17):3068-3077.
Waldron et al., "Targeting Tumor-Initiating Cancer Cells with dCD133KDEL Shows Impressive Tumor Reductions in a Xenotransplant Model of Human Head and Neck Cancer," *Molecular Cancer Therapeutics*, 2011; 10:1829-1838. Available online Aug. 23, 2011.
Weigmann et al., "Prominin, a novel microvilli-specific polytopic membrane protein of the apical surface of epithelial cells, is targeted to plasmalemmal protrusions of non-epithelial cells," *Proc. Natl. Acad. Sci. U.S.A.*, Nov. 1997; 94:12425-30.
Written Opinion, mailed May 11, 2011, International Application No. PCT/US2010/059827, filed Dec. 10, 2010; 9 pgs.
Yin et al., "AC133, a novel marker for human hematopoietic stem and progenitor cells," *Blood*, Dec. 15, 1997; 90(12):5002-12.

SINGLE-CHAIN VARIABLE FRAGMENT ANTI-CD133 ANTIBODIES AND USES THEREOF

CROSS-REFERENCE TO RELATED APPLICATION

This application claims priority to U.S. Provisional Patent Application Ser. No. 61/348,348, filed May 26, 2010 and U.S. Provisional Patent Application Ser. No. 61/390,011, filed Oct. 5, 2010, each of which is hereby incorporated by reference in its entirety.

BACKGROUND

Cancer cells differentiate, as do normal cells. The tumor cell populations include a relatively small cohort of less differentiated, self-renewing, tumor initiating stem cells and a relatively larger cohort of more differentiated tumor cells. More differentiated cells are more susceptible to chemotherapy and the minor fraction of less differentiated cancer stem cells are more drug resistant, thus contributing to drug refractory relapse. CD133 is an established marker for cancer stem cells Human CD133 is a cell surface glycoprotein that has been used as a marker of hematopoietic stem cells, neural stem cells, and for enrichment of a tumor initiating cell population in many cancers including colon carcinoma and glioblastoma (Kemper et al.; Weigmann et al., 1997; Yin et al., 1997). Anti-CD133 antibodies are important tools useful in the identification, isolation and targeting of these stem cell populations. Although many CD133 antibodies are commercially available, they have several limitations. First, the most widely used anti-CD133 monoclonal antibodies recognize what was initially thought to be poorly-defined glycosylated epitopes (Bidlingmaier et al., 2008), but more recently reported to be non-glycosylated epitopes that are lost during differentiation, perhaps due to epitope masking (Kemper et al.). In either case, these antibodies do not detect cells expressing certain post-translationally modified CD133 epitopes and therefore cannot be used to determine the total CD133 expression. Second, commercially available anti-CD133 antibodies that target an unmodified CD133 epitope are often polyclonal. Third, most of the currently available antibodies are only suitable for use in limited biological assays. To overcome these shortcomings, there is a need to generate a new anti-CD133 monoclonal antibody that specifically recognizes a non-glycosylated epitope of CD133 and is useful in multiple biological assays.

Carcinomas are invasive malignant tumors of transformed epithelial cells. Some of the deadliest cancers are carcinomas including drug refractory cancers of the pancreas, head and neck, prostate, breast, colon, and other organs. For example, in pancreatic cancer, only 10-15% of patients are found to be resectible at diagnosis because of its aggressive growth and rapid speed of metastasis to lymph nodes and liver. Median survival is 3-6 months with a 5-year survival rate of 1-4% when all stages are considered and more than 32,000 patients each year die in U.S. alone. Breast cancer, with a considerably better survival rate, still had an estimated 178,000 new cases in 2007 with an expected 40,000 fatalities according to the American Cancer Society. In the case of head and neck cancers, in the United States, of 40,000 in reported cases in 2006, about 11,000 died of their disease. The primary culprit is a metastatic reoccurrence of drug refractory disease, so alternative drugs are urgently needed.

SUMMARY OF THE INVENTION

In one aspect, the invention provides a monoclonal antibody that specifically binds to human CD133. In some embodiments, the monoclonal antibody is a monoclonal antibody produced by Hybridoma Clone 7, as described herein.

In another aspect, the invention provides the hybridoma identified herein as Hybridoma Clone 7.

In another aspect, the invention provides a single-chain variable-fragment (scFv) of the monoclonal antibody produced by Hybridoma Clone 7. In some embodiments, the scFv comprises the amino acid sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, or SEQ ID NO:55. In one particular embodiment, the scFv comprises the amino acid sequence of SEQ ID NO:53.

In another aspect, the invention provides an isolated polynucleotide comprising a nucleotide sequence that encodes the amino acid sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, or SEQ ID NO:55. In some embodiments, the isolated polynucleotide comprises a nucleotide sequence that encodes the amino acid sequence of SEQ ID NO:53. In one particular embodiment, the isolated polynucleotide comprises the nucleic acid sequence of SEQ ID NO:56.

In another aspect, the invention provides fusion polypeptides. Generally, a fusion polypeptide includes a targeting moiety and a toxin moiety. The targeting moiety can include a monoclonal antibody described herein or a scFv thereof that specifically binds to a marker that is differentially expressed by cancer stem cells. In some embodiments, the toxin moiety can include a deimmunized therapeutically active portion of a cytolytic toxin.

In another aspect, the invention provides compositions that include a plurality of fusion polypeptides as just described. In some embodiments, the composition can include a first fusion polypeptide and a second fusion polypeptide, wherein the first fusion polypeptide specifically binds to a first marker differentially expressed by cancer stem cells and the second fusion polypeptide specifically binds to a second marker differentially expressed by cancer stem cells. In one embodiment, one fusion polypeptide may specifically bind to CD133 and another fusion polypeptide may specifically bind to EGFR.

In another aspect, the invention provides compositions in which the monoclonal antibody or scFv thereof may be coupled to a nanoparticle. In certain embodiments, the nanoparticle may be biodegradable. In certain embodiments, the nanoparticle may contain a cytolytic toxin.

In another aspect, the invention provides therapeutic methods that include administering to a subject in need of such treatment a therapeutically effective amount of a composition that includes a monoclonal antibody described herein or a scFv thereof. In some embodiments, the monoclonal antibody or scFv thereof may be fused to a therapeutic moiety or coupled to a nanoparticle that contains a therapeutic compound.

In another aspect, the invention provides a composition that includes a monoclonal antibody as described herein or a scFv thereof coupled to a detectable marker.

In yet another aspect, the invention provides a method of detecting cells that express a cancer stem cell marker. Generally, the method includes contacting at least one cell that expresses CD133 and a composition that includes a monoclonal antibody as described herein or a scFv thereof coupled to a detectable marker and detecting a portion of the composition that specifically binds to the cell. In some embodiments, the composition may be administered to a subject.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2: Analysis of the newly generated CD133 hybridoma. Supernatants of hybridoma clones were tested as a primary antibody in western blot (A) and Immunofluorescence (B) assays. Pre-immunized serum (-ve) or post immune anti sera (a.s.) served as controls. For western blot, Caco-2 lysates normalized for protein concentration were loaded onto a SDS-PAGE gel, resolved, blotted onto a nitrocellulose membrane and cut into strips. Each strip was probed with supernatant from the identified hybridoma. Membrane in Lane 1 was probed with a commercially available antibody (ab 19898, Abcam) and served as an additional positive control. For immunofluorescence, Caco-2 cells were fixed and immunostained with the hybridoma supernatants. A commercially available antibody (293C3, Militenyi) was used as additional positive control. Scale bars in the panel represent 200 micrometers. Supernatant of Hybridoma Clone 7 was used in the immunohistochemical analysis of primary glioblastoma and kidney tissue (C).

DETAILED DESCRIPTION OF ILLUSTRATIVE EMBODIMENTS

Figure 1:
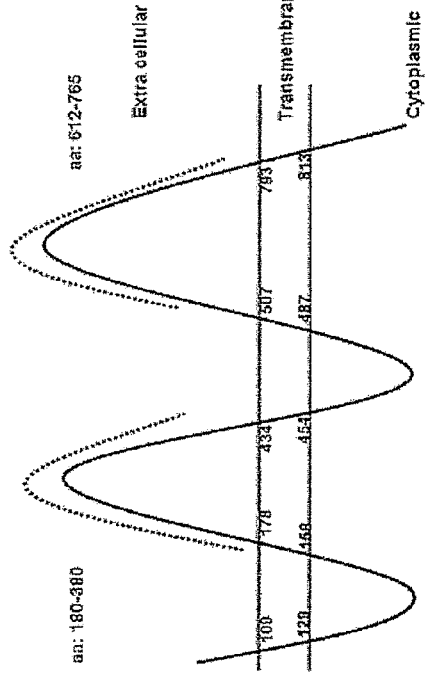
FIG. 1: CD133 antigen used for vaccination. Topology map (A) and amino acid sequence of CD133 protein (B, SEQ ID NO:1). A recombinant chimeric CD133 antigen (SEQ ID NO:2) consisting of amino acid residues 180-380 and 612-765 of SEQ ID NO:1, underlined in (B), was generated. This recombinant chimeric CD133 antigen (SEQ ID NO:2) was bacterially expressed, purified and demonstrated to have a molecular weight of 45 kDa by SDS-PAGE (C).

The present invention provides compositions and methods that exploit the discovery of monoclonal antibodies and fragments thereof that specifically bind to certain markers that are differentially expressed by cancer stem cells. The compositions and methods described herein may provide additional options for the detection and treatment of certain forms of cancer because the monoclonal antibodies (and fragments thereof) target a population of cancer stem cells. This may allow for earlier detection of certain forms of cancer and/or provide effective treatment by targeting a small but proliferative subpopulation of tumor cells.

Throughout the disclosure that follows, the following terms shall have the indicated meanings:

"Differentially expressed" refers to the character of a marker that is expressed to a different degree by a cancer stem cell compared to the expression of the marker by another cell type. In some cases, the differential expression may be that the marker is expressed to a greater degree by a cancer stem cell than by another cell type. In certain cases, the marker may be expressed by a cancer stem cell, but not expressed at a detectable level in a cell type other than a cancer stem cell.

"Moiety" and variations thereof refer to a portion of a chemical compound that exhibits a particular character such as, for example, a particular biological or chemical function (e.g., target specificity or cytolytic activity).

"Polypeptide" refers to a polymer of amino acids linked by peptide bonds. Thus, for example, the terms peptide, oligopeptide, protein, and enzyme are included within the definition of polypeptide. This term also includes post-expression modifications of the polypeptide, such as glycosylations, acetylations, phosphorylations, and the like. The term polypeptide does not connote any particular minimum length or maximum length of a polymer of amino acids. A polypeptide may be isolatable directly from a natural source, or can be prepared with the aid of recombinant, enzymatic, or chemical techniques.

"Specific" and variations thereof refer to having a differential or a non-general (i.e., non-specific) affinity, to any degree, for a particular target.

"Therapeutic" and variations thereof refer to a treatment or a moiety that ameliorates one or more existing symptoms or clinical signs associated with a condition. "Ameliorate" refers to any reduction in the extent, severity, frequency, and/or likelihood of a symptom or clinical sign characteristic of a particular condition. "Sign" or "clinical sign" refers to an objective physical finding relating to a particular condition capable of being found by one other than the patient. "Symptom" refers to any subjective evidence of disease or of a patient's condition.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

A significant disadvantage of the currently available CD133 antibodies is that each antibody is suitable only for a specific type of immunoassay, requiring use of multiple antibodies for a broad range of techniques. Here we report a novel anti-CD133 monoclonal antibody that recognizes the CD133 antigen in Western blotting, immunofluorescence, immunohistochemistry, and flow cytometry applications. The preliminary screening of hybridomas in our studies was accomplished by ELISA, suggesting that Hybridoma Clone 7 could potentially be used in ELISA applications as well. In addition, we have cloned the single-chain variable-fragment (scFv) of the Hybridoma Clone 7 antibody.

A second, related limitation of existing CD133 antibodies is that the most commonly used anti-CD133 antibodies, e.g., AC133 and 293C3, recognize what have been reported to be glycosylated CD133 epitopes (reviewed in Bidlingmaier et al., 2008). Alternatively, others proposed that these are not glycosylated epitopes, but rather epitopes that become masked as a consequence of glycosylation due to changes protein folding. Perhaps not surprisingly, there has been great controversy regarding the ability of cells sorted using these glycosylation-dependent CD133 antibodies to enrich for cells with increased tumor initiation and self-renewal capacity. Numerous reports have documented CD133+ cells with exclusive tumor-initiating potential, but many contradictory studies have demonstrated CD133− cells also initiate tumors in xenotransplantation assays (Bidlingmaier et al., 2008). In some cases, the so-called "CD133− cells" are CD133+ cells that have lost the AC133/293C3 epitopes. Indeed, differentiation of colon tumor-initiating cells may be accompanied by a loss of the AC133 epitope, tumorigenicity, and clonogenicity, despite stable levels of CD133 mRNA.

The combined use of glycosylation-dependent (e.g., AC133, 293C3) and glycosylation-independent (e.g., Hybridoma Clone 7) CD133 antibodies could be an extremely powerful tool to distinguish changes in CD133 glycosylation from changes in CD133 expression. This may be a distinction that is exploitable in the effort to test the cancer stem cell hypothesis using cells sorted based on surface markers such as CD133. The demonstrated reactivity of Hybridoma Clone 7 for glycosylated and non-glycosylated epitopes suggests it could be useful to target therapeutics to CD133+ cancer cells regardless of differentiation state.

A recombinant chimeric antigen consisting of amino acid residues 180-380 and 612-765 of the CD133 protein was designed (FIG. 1A, FIG. 1B) based on the reported structure of CD133 (Shmelkov et al., 2005). Hopp-Woods antigenic analysis plot, Kyte-Doolittle hydropathy characterization and Emini Surface probability analysis were used to identify and avoid hydrophobic, non-specific, and weakly immunogenic regions. The recombinant antigen was expressed in *E. coli*, purified, and analyzed by SDS-PAGE (FIG. 1C). The purified protein had a molecular weight of 45 kDa, which was in agreement with the predicted molecular weight.

The purified antigen was injected into BALB/c mice for the generation of monoclonal anti-CD133 antibody using standard hybridoma technology. Cell culture supernatants from the resulting hybridoma clones were screened for the production of antibodies against recombinant CD133 by ELISA. After two rounds of screening, 11 positive stable hybridoma clones secreting anti-CD133 antibodies were obtained.

Figure 2:
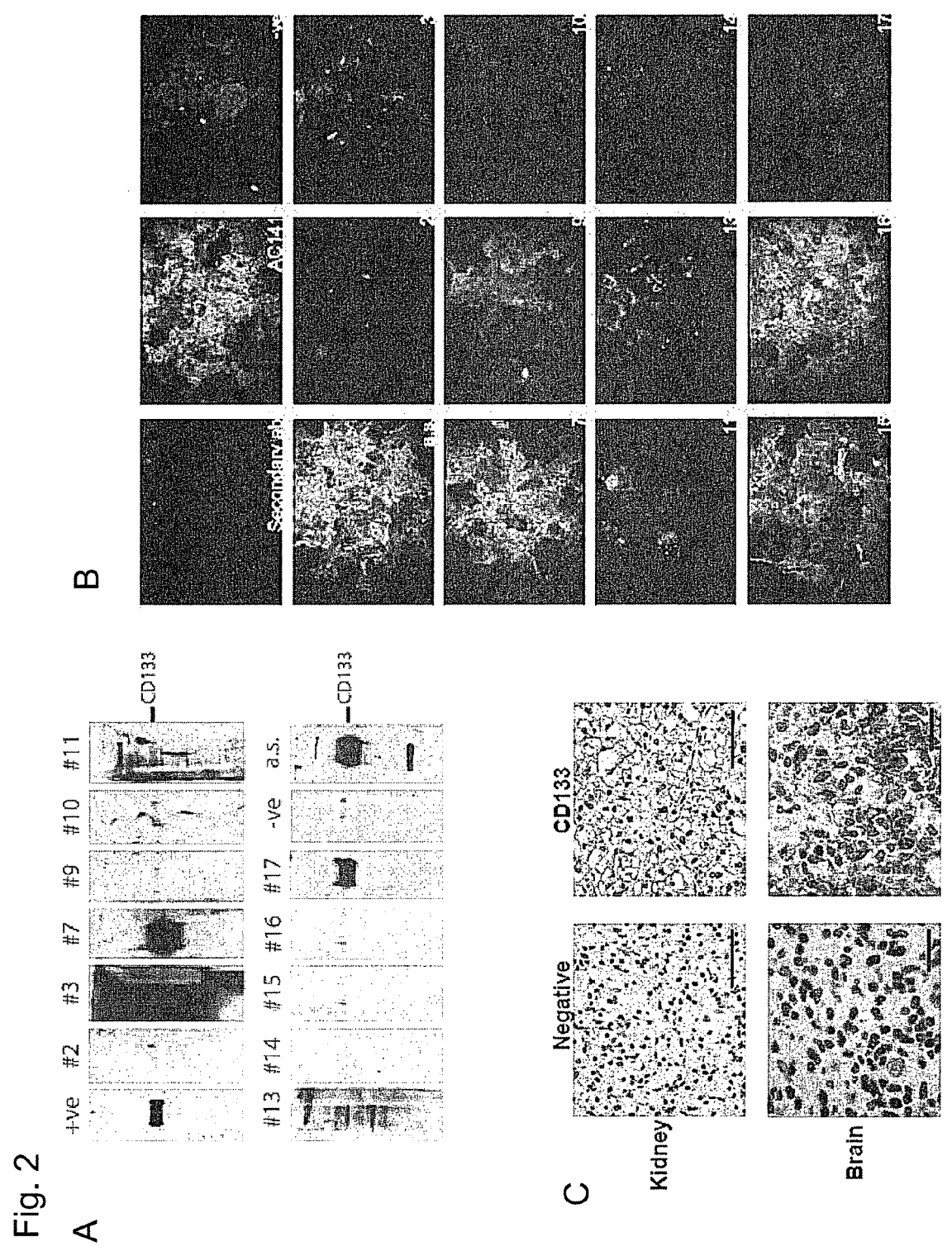

We validated the screened hybridomas by Western blot and immunofluorescence assays using CD133+ Caco-2 cells, which revealed a distinct band corresponding to the predicted molecular weight of CD133 with the supernatants of only Hybridoma Clone 7 and Hybridoma Clone 17 (FIG. 2A). In the immunofluorescence assay, however, supernatants from Hybridoma Clone 7, Hybridoma Clone 15, and Hybridoma Clone 16 robustly stained the Caco-2 cell membrane, while supernatant from Hybridoma Clone 9 and Hybridoma Clone 13 provided weak staining (FIG. 2B).

As Hybridoma Clone 7 was effective in recognizing the CD133 epitope in both the assays, we selected it for further characterization and to test its use in other applications. In the immunohistochemical analysis of human glioma and kidney tissue sections, Hybridoma Clone 7 resulted in membrane-specific staining (FIG. 2C). The staining was sharp and uniform in the kidney sections and more heterogeneous in the glioma tissue.

Figure 3:
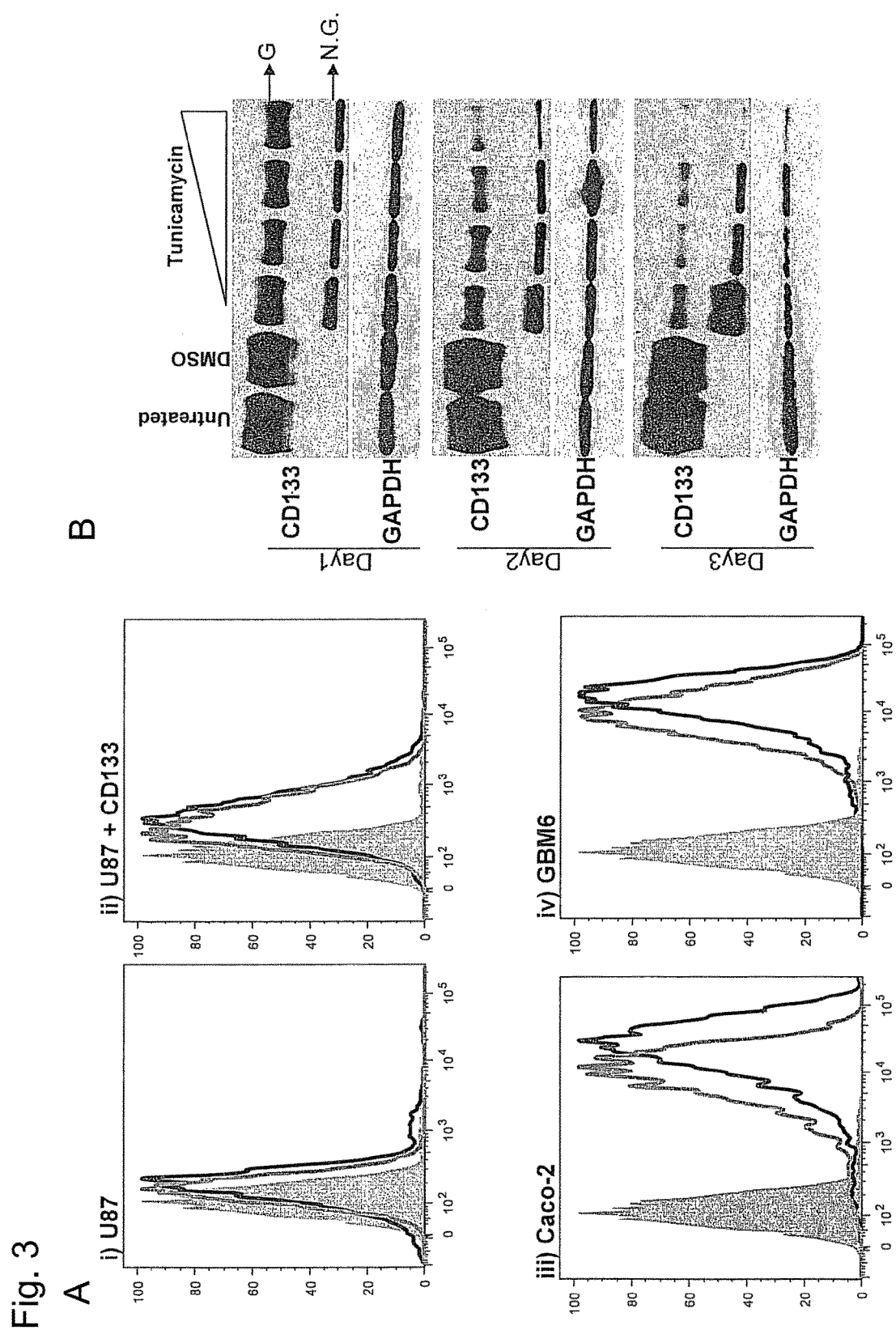
FIG. 3: Specificity of antibody produced by Hybridoma Clone 7. (A) Flow cytometry. Cells were incubated with primary antibody from either Hybridoma Clone 7 or 293C3 (Militenyi), followed by incubation with a labeled secondary antibody, and then analyzed by flow cytometry. Antibody from the newly developed anti-CD133 Hybridoma Clone 7 (open black histogram) stains very specifically the CD133-overexpressing cells, Caco-2 (iii), GBM6 (iv) and U87 cells transfected with CD133 (ii) but not CD133 negative U87 cells (i). Immunostaining using the monoclonal antibody produced by Hybridoma Clone 7 is compared to clone 293C3 (open grey histogram). Isotype control is represented by solid grey histogram. (B) Tunicamycin mediated glycosylation inhibition. Caco-2 cells were treated with increasing doses of tunicamycin (2.5, 5, 10, 20 µg/ml) for 3 days. DMSO treated cells or untreated cells served as controls. Cells were lysed and then analyzed by Western blotting using the monoclonal antibody produced by Hybridoma Clone 7 or GAPDH antibodies.

We next determined the specificity of Hybridoma Clone 7 to CD133. CD133$^{low/-}$U87 cells were transfected with an expression plasmid encoding the human CD133 cDNA, stained with either Hybridoma Clone 7 or a commercially-available CD133 antibody (293C3) and analyzed by flow cytometry. Appropriate isotype antibody and mock transfected U87 cells were used as controls. Hybridoma Clone 7 and 293C3 antibody did not appreciably stain non-transfected U87 cells (FIG. 3A(i) and FIG. 3A(ii)). In contrast, both antibodies labeled CD133-transfected cells, demonstrating the specificity of Hybridoma Clone 7 for CD133. Next, Hybridoma Clone 7 was able to immunostain Caco-2 and GBM6 cells that endogenously express CD133 like the 293C3 antibody. (FIG. 3A(iii) and FIG. 3A(iv)).

Next, we determined whether Hybridoma Clone 7 recognizes a glycosylated epitope. Caco-2 cells were treated with tunicamycin, a well-documented protein glycosylation inhibitor (Tkacz and Lampen, 1975; Lehle and Tanner, 1976), prior to Western blot analysis. In tunicamycin treated samples, a 130 kDa band corresponding to glycosylated CD133 protein and a 95 kDa band likely from non-glycosylated protein were seen. In contrast, only the glycosylated CD133 band was seen in control samples. The 130 kDa band was present even in samples treated with high doses of tunicamycin and following prolonged treatment, indicating incomplete inhibition of CD133 glycosylation in these cells. Higher doses of tunicamycin resulted in apparent cytotoxicity as is evident from declining GAPDH bands. These results strongly suggest that Hybridoma Clone 7 specifically binds to an non-glycosylated epitope.

Next, Hybridoma Clone 7 was used to clone the scFv of the CD133-specific monoclonal antibody produced by Hybridoma Clone 7. Initially, a mouse scFv library was constructed using RNA derived from Hybridoma Clone 7. After total RNA purification and first-strand cDNA synthesis, the scFv-encoding gene repertoire was amplified (Example 10). The VH and VL gene pools were separately amplified from the synthesized cDNA. The scFv genes were assembled randomly by fusing VH and VL fragments using an overlap PCR. The scFv cDNA and vector were digested by a single, rarely-cutting restriction endonuclease, SfiI. After ligation, the recombinant constructs were transformed into electrocompetent *E. coli* XLI-BLUE.

After overnight incubation, the amplified recombinant phagemid was extracted from the host bacteria. The library construction was achieved in only one transformation and had a theoretical size of $1.0 \times 10^7$.

Standard panning was performed for three rounds, after which 30 randomly-selected clones were assayed for their reactivity against CD133 using phage ELISA. Nine positive clones were identified, each producing a scFv: SEQ ID NO:47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55. DNA sequencing showed that five of the nine CD133-specific clones were identical, strongly suggesting that they are all derived from the single Hybridoma Clone 7.

Recombinant Clone 11 (encoding SEQ ID NO:53) was selected for transformation into *E. coli* Top 10F' for expression. In that process, Recombinant Clone 11 was truncated at both the 5' end and the 3' end so that the scFv polypeptide encoded by the clone possess a deletion of N-terminal amino acids and C-terminal amino acids. The cloned coding sequence is reflected in SEQ ID NO:57 and the encoded scFv polypeptide is reflected in SEQ ID NO:58. As compared to SEQ ID NO:53, SEQ ID NO:58 is truncated by six amino acids at the N-terminal and 16 amino acids at the C-terminal. SEQ ID NO:58 also possesses a methionine at the N-terminal, which is an artifact of the cloning process.

Soluble expression of the scFv (SEQ ID NO:58) was achieved by using *E. coli* secretion machinery and induced at low temperature (30° C.). The expressed scFv (SEQ ID NO:58) was found mainly in the culture medium and *E. coli* periplasmic space.

Soluble scFv ELISA was performed to confirm the binding specificity to CD133. The Recombinant Clone 11 scFv (SEQ ID NO:58), present in both the culture medium and the periplasmic space, was specific for human CD133.

Thus, in one aspect, the invention provides a scFv of the monoclonal antibody produced by Hybridoma Clone 7, as described herein. As used herein, a scFv of the monoclonal antibody produced by Hybridoma Clone 7 can include a polypeptide that includes any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:58 or a polypeptide structurally similar to a reference polypeptide that includes any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:58.

In one embodiment, the scFv includes the amino acid sequence of SEQ ID NO:53. In other embodiments, the scFv is a polypeptide that is structurally similar to a reference polypeptide, in which the reference polypeptide includes the amino acid sequence of SEQ ID NO:53.

In another embodiment, the scFv includes the amino acid sequence of SEQ ID NO:58. In other embodiments, the scFv is a polypeptide that is structurally similar to a reference polypeptide, in which the reference polypeptide includes the amino acid sequence of SEQ ID NO:58.

As used herein, a polypeptide is "structurally similar" to a reference polypeptide if the amino acid sequence of the polypeptide possesses a specified amount of identity compared to the reference polypeptide. Structural similarity of two polypeptides can be determined along the entire length of the longer polypeptide by aligning the residues of the two polypeptides (for example, a candidate polypeptide and the polypeptide of, for example, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide. A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids along the entire length of the longer polypeptide. "Similarity" refers to the presence of not only identical amino acids but also the presence of conservative substitutions along the entire length of the longer polypeptide. A conservative substitution for an amino acid may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or non-contiguous amino acids that do not eliminate a functional activity of the polypeptide are also contemplated.

A polypeptide of the present invention can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to the reference amino acid sequence.

A polypeptide of the present invention can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the reference amino acid sequence.

Whether assessing amino acid similarity or amino acid identity, a reference amino acid sequence can be any on of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58. Thus, in some embodiments, the reference amino acid sequence includes the amino acid sequence of SEQ ID NO:47. In other embodiments, the reference amino acid sequence includes the amino acid sequence of SEQ ID NO:48. In other embodiments, the reference amino acid sequence includes the amino acid sequence of SEQ ID NO:49. In other embodiments, the reference amino acid sequence includes the amino acid sequence of SEQ ID NO:50. In other embodiments, the reference amino acid sequence includes the amino acid sequence of SEQ ID NO:51. In other embodiments, the reference amino acid sequence includes the amino acid sequence of SEQ ID NO:52. In other embodiments, the reference amino acid sequence includes the amino acid sequence of SEQ ID NO:53. In other embodiments, the reference amino acid sequence includes the amino acid sequence of SEQ ID NO:54. In other embodiments, the reference amino acid sequence includes the amino acid sequence of SEQ ID NO:55. In other embodiments, the reference amino acid sequence includes the amino acid sequence of SEQ ID NO:58.

In one particular embodiment, the reference amino acid sequence includes SEQ ID NO:53. In another particular embodiment, the reference amino acid sequence includes the amino acid sequence of SEQ ID NO:58.

For example, as described above, SEQ ID NO:58 is a scFv polypeptide that represents a somewhat truncated version of SEQ ID NO:53. SEQ ID NO:58 possesses 243 amino acids, 242 of which are identical to corresponding amino acids in SEQ ID NO:53, which possesses 263 amino acids. Accordingly, SEQ ID NO:58 possess 92% sequence identity compared to SEQ ID NO:53. Similar truncations of the amino acids sequences of SEQ ID NO:47, SEQ ID NO:48, SEQ ID NO:49, SEQ ID NO:50, SEQ ID NO:51, SEQ ID NO:52, SEQ ID NO:54, or SEQ ID NO:55 may similarly provide suitably functional polypeptides.

A polypeptide of the present invention can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

In another aspect, the invention provides an isolated polynucleotide molecule that encodes a scFv of a monoclonal antibody produced by Hybridoma Clone 7, as described herein. Exemplary isolated polynucleotides include an isolated polynucleotide that encodes the amino acid sequence of any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58, or a polypeptide structurally similar to a reference polypeptide that includes any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58. Exemplary polynucleotides also include the complements of such polynucleotide sequences. Also included in the present invention are polynucleotides that hybridize, under standard hybridization conditions, to a polynucleotide that encodes the amino acid sequence of any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:58, or a polypeptide structurally similar to a reference polypeptide that includes any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58, and the complements of such polynucleotide sequences.

Also included in the present invention are polynucleotides having a sequence identity of at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a reference nucleotide sequence that encodes the amino acid sequence of any one of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58.

In some embodiments, the reference nucleotide sequence can encode the amino acid sequence of SEQ ID NO:53. In one embodiment, the reference nucleotide sequence can include the nucleotide sequence of SEQ ID NO:56.

In other embodiments, the reference nucleotide sequence can encode the amino acid sequence of SEQ ID NO:58. In one embodiment, the reference nucleotide sequence can include the nucleotide sequence of SEQ ID NO:57.

As used herein, "sequence identity" refers to the identity between two polynucleotide sequences. Sequence identity is generally determined by aligning the residues of the two polynucleotides to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence. For example, two polynucleotide sequences can be compared using the Blastn program of the BLAST 2 search algorithm, as described by Tatiana et al., *FEMS Microbiol Lett.*, 1999; 174: 247-250, and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, about 700, or about 800 nucleotides in length. Alternatively, such a portion may be about 10 nucleotides to about 100 nucleotides in length.

A monoclonal antibody, scFv, or polynucleotide of the invention can be used to identify whether a sample from a subject possesses cells that express CD133. Human CD133 is a cell surface glycoprotein that has been used as a marker of hematopoietic stem cells, neural stem cells, and for enrichment of a tumor initiating cell population in many cancers including colon carcinoma and glioblastoma. Thus, identification, localization, and/or quantitation of CD133-expressing cells may provide medical practitioners with information regarding whether the subject from which a sample is obtained has, or is at risk of developing, a condition characterized at least in part by cells that express CD133. In some embodiments, identifying cells that express CD133 in a biological sample obtained from a subject may indicate that the subject has, or is at risk for developing, colon cancer and/or glioblastoma.

Generally, a monoclonal antibody, scFv, or polynucleotide of the invention can be contacted with at least a portion of a biological sample obtained from a subject. In the case of monoclonal antibody or scFv, the biological sample can include cells that express CD133, fragments of cells that express CD133, and/or CD133 that is at least partially isolated from cells in the biological sample. In the case of polynucleotide, the biological sample can include, for example, lysed cells, genomic DNA, mRNA, and/or cDNA (or other products of mRNA amplification by, for example, PCR).

One can detect whether the monoclonal antibody, scFv, or polynucleotide specifically binds to a component of the biological sample in a manner that is indicative of CD133 expression by cells in the sample. For example, the specific binding of the monoclonal antibody or scFv to at least a portion of CD133 may be detected. Similarly, specific binding (e.g., hybridization) of a polynucleotide of the invention—denatured, if necessary—to at least a portion of a polynucleotide from the sample—again, denatured, if necessary—that is indicative of CD133 expression.

The cancer stem cell compartment contains more than one stem cell population and CD133KDEL is highly effective against at least one of these populations expressing CD133. We detected about 5% CD133 cells/95% CD133-cells in the various carcinomas that we examined. For example, Table 1 shows several lines. The anti-CD133 scFV was labeled with FITC and then standard flow cytometry was performed. The levels of CD133 expression (4-7.1%) are in agreement with values reported values. CaCo-2 colorectal carcinoma is a cell line known to express high levels of CD133+ cells so we included it as a positive control. Anti-CD45-FITC and anti-CD19 FITC are negative controls that preferentially recognize hematopoietic cells.

TABLE 1

CD133+ Expression on Various Carcinoma Lines.

| Cell Line | Cancer Origin | % Positive Cells | | | |
|---|---|---|---|---|---|
| | | CD133+ | EGFR+ | CD45+ | CD19+ |
| MDA-MB231 | breast | 4.0 | 82.5 | — | 0.4 |
| MDA-MD468 | breast | 5.2 | 96.1 | 0.9 | — |
| SKBR3 | breast | 4.2 | 99.8 | 0.7 | — |
| BT474 | breast | 4.0 | 99.9 | 0.6 | — |
| NA | head & neck | 5.9 | — | — | 1.1 |
| UMSCC-11B | head & neck | 6.0 | 98.0 | 0.5 | 0.3 |
| MiaPaCa-2 | pancreas | 7.1 | 97.3 | 0.8 | — |
| Caco-2 | colon | 62.8 | 82.7 | — | 0.3 |

Thus, the monoclonal antibody and/or the scFv may be used in diagnostic methods designed to detect the presence of cancer stem cells in a subject that may indicate that the subject has or is at risk of having a neoplastic condition such as, for example, a carcinoma. Such diagnostic methods can include obtaining an appropriate biological sample from a subject, contacting the monoclonal antibody and/or scFv with a portion of the biological sample in vitro, and detecting specific binding of the monoclonal antibody and/or scFv to cells in the biological sample. In other cases, a diagnostic method can include administering a composition that includes the monoclonal antibody and/or scFv, coupled to an appropriate detectable marker, to a subject and then detecting specific binding of the at least a portion of the composition to cells of the subject in vivo.

Therapeutic Uses

Although the anti-CD133 antibody was originally developed as a diagnostic tool, studies indicate that CD133 is rapidly internalized upon binding by a ligand such as, for example, the anti-CD133 antibody described herein. Because cells that have markers that are rapidly internalized are very good targets for targeted toxins, we synthesized CD133 targeted toxin by assembling a scFv fusion molecule that includes the toxin cloned onto the same molecule with our anti-CD133 scFv: the targeted toxin dCD133KDEL.

One source of cancer reoccurrence in chemotherapy-treated carcinoma patients is cancer stem cells. It is now recognized that cancer stem cells differentiate, as do normal cells. Thus, there is a small cohort of less differentiated, self-renewing, tumor initiating stem cells. There is also a larger cohort of more differentiated cancer stem cells. Unfortunately, it is the more differentiated cells that are more susceptible to chemotherapy and the minor fraction of less differentiated cancer stem cells that are more drug resistant. Furthermore, these less differentiated cancer stem cells have the capacity to self-renew their numbers and initiate tumors, thus contributing to metastatic disease. This now is established in a variety of carcinomas in which cancer stem cells are sorted using established stem cell markers such as CD133 or CD44. The sorted cells are xenografted into mice and the rate at which the tumors initiate and self renew is markedly enhanced in tumor initiation assays. Because stem cells can be more resistant to chemotherapy than tumor cells that are not stem cells, a drug that can selectively destroy these cancer stem cells would be extremely valuable for the prevention of relapse and metastasis. Targeted toxins are powerful catalytic inhibitors of protein synthesis and numerous reports show that they kill drug-resistant cells by an entirely different mechanism than conventional chemotherapeutic drugs. Thus, we used genetic engineering to design a TT that would eliminate cancer stem cells.

CD133 is a stem cell marker for various cancers. Expression of CD133 in cancer-initiating cells is well documented for brain, prostate, and colon cancers and more recently in breast cancer. CD133, also known as prominin-1, is a cell-surface glycoprotein with five transmembrane domains and two large glycosylated extracellular loops that localize to membrane protrusions. The function of CD133 in cancer stem cells has not been established, but one alternatively-spliced form binds cholesterol and thus may be involved in Hedgehog signaling, which is required for primitive cell differentiation and epithelial-mesenchymal interactions.

Some studies regarding CD133 have been criticized because the available commercial anti-CD133 monoclonal antibodies recognize glycosylated CD133 and thus are not desirable because they do not detect cells expressing post-translationally modified CD133 epitopes and are not accurate for determining total CD133 expression. As a solution, the monoclonal antibody identified herein as produced by Hybridoma Clone 7 and the scFv therefrom and described herein were developed.

Targeted toxins (TT), on a molecule/cell basis, are potent killers of cancer target cells. They are enzymatic inhibitors of protein synthesis. Since they are enzymes catalyzing the ADP-ribosylation of Elongation Factor-2, they travel through the cytosol completing one chemical reaction and then initiate the next. Chemotherapeutic agents do not share this mechanism and on a single molecule basis are less efficient. Importantly, patient tumors often become refractory to chemotherapy, and in many instances, administration of chemotherapy is not an option because it has become too toxic, particularly to the hematopoietic system. Because catalytic toxins have a different anti-cancer mechanism, targeted toxins represent a compelling alternative to conventional therapies, especially since they synergize with chemotherapy, even in pancreatic cancer. There are many published reports regarding synergy of targeted toxin and chemotherapeutic agents. Therefore we assembled an anti-CD133 targeted toxin consisting of the anti-CD133 scFV and a downstream pseudomonas exotoxin. The endoplasmic reticulum retention sequence KDEL was added to the c-terminus because it known to promote the entry of toxin into the cytosolic compartment and enhance killing. We called the molecule dCD133KDEL.

Thus, we have produced a first of its kind anti-stem cell biological dCD133KDEL capable of killing tumor stem cells. Although CD133+ stem cells represent only a minority (4-7%) of the tumor cell population, we are surprised by the fact that in culture nearly all of the cells were killed over time with treatment with dCD133KDEL. We have produced a novel anti-CD133 monoclonal that recognizes the non-glycosylated backbone of the CD133 extracellular domain.

The scFv-TT fusion has surprisingly high anti-carcinoma activity in vitro and high anti-tumor efficacy when injected systemically in vivo. This is the first drug of its type recognizing an established stem cell marker, CD133.

Still, combining dCD133KDEL with EGF4KDEL markedly enhanced systemic carcinoma killing in vivo compared to individual administration of either CD133KDEL or EGF4KDEL alone. (EGF4KDEL is a bispecific TT targeting EGFR.) An interpretation of our combined in vitro and in vivo findings is that there is more than one stem cell fraction.

One candidate is a population of CD44+ cancer stem cells, which is believed to be independent of CD133+ stem cells in colon cancer. CD44, however, is a receptor for hyaluronic acid and is ubiquitously expressed in normal cells. Thus, a CD44-based therapeutic would, in contrast to the CD133-based therapeutics described herein, be likely exhibit substantial cross-reactivity with non-target organs. Another candidate is epidermal growth factor (EGF). Still another is epithelial cell adhesion molecule (EpCAM), which is also widely expressed on carcinomas and is expressed on cancer stem cells. Antibody microarray analysis may ultimately identify additional targets.

Thus, in another aspect, the invention includes therapeutic uses of the monoclonal antibody, scFv, or polynucleotide of the invention. In one embodiment, the scFv was used to clone a targeted toxin (TT) that includes the scFv fused to truncated pseudomonas exotoxin that was effectively deimmunized so that repeated treatments could be given with a reduced consequence of the generation of anti-toxin antibodies. Despite the presence of only a small fraction of CD133+ cancer stem cells measured by flow cytometry, the scFv-TT fusion (dCD133KDEL) was highly effective in reducing the expansion of cultured carcinoma cells in vitro using breast cancer and head and neck cancer cell lines. When tested in vivo, the drug was effective inducing complete remissions in a high percentage of animals. CD133, alone, had impressive effects, but the scFv-TT fusion had even better effects.

The scFv-TT fusion represents a new tool for recognizing and eliminating CD133+ cancer stem cells. As used herein, "eliminate" and variations thereof refer to reducing the proliferation of living cells in the population being "eliminated" to any degree with respect to an appropriate control population of cells. Thus, in some circumstances, "eliminating" certain cells can include an increase in the actual population of "eliminated" cells, but the increase is less than the corresponding population increase observed in an appropriate control population. Thus, in some embodiments, "eliminating" cells can include reducing the population of eliminated cells by at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95, at least 96%, at least 97%, at least 98%, at least 99%, or 100% compared to an appropriate control population. In other embodiments, "eliminating" cells may refer to an actual decrease in the number of cells in the population. In these embodiments, "eliminating" cells can include reducing the actual number of eliminated cells by at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95, at least 96%, at least 97%, at least 98%, at least 99%, or 100%.

For example, one can eliminate CD133+ stem cells from cell cultures using the scFv-TT fusion and then study what stem cell populations remain. The remaining cell populations may be detected using, for example, 2-color and 3-color fluorescence. Such a strategy can allow one to identify a second cancer stem cells population that expresses prominent carcinoma markers. For example, we have evidence that EGFR/EpCAM expressing cells remain after eliminating CD133+ cells using dCD133KDEL.

As another example, one can eliminate CD133+ stem cells in vivo to provide anti-cancer therapy to a subject in need of such treatment. A scFv-TT fusion that includes an anti-CD133 scFv can provide targeted delivery of the targeted toxin to CD133+ cancer stem cells. CD133+ cancer stem cells have been identified in a number of different carcinomas, glioblastomas, astrocytomas, and sarcomas. Consequently, a scFv-TT fusion containing an anti-CD133+ scFv may provide a single therapeutic option capable of treating one or multiple tumors of various origins. Exemplary tumors include brain tumors (e.g., glioblastomas, astrocytomas, etc.), muscle tumors (e.g., sarcomas), and/or various carcinoma such as, for example, breast cancer, pancreatic cancer, head and neck cancer, prostate cancer, colon cancer, any of the carcinomas listed in Table 2, or any combination of carcinomas.

TABLE 2

Exemplary carcinomas

| Classification | Name (NOS = not otherwise specified) |
|---|---|
| (8010-8040) | Epithelial neoplasms, NOS |
| (8050-8080) | Squamous cell neoplasms |
| (M8070/3) | Squamous cell carcinoma, NOS |
| (8090-8110) | Basal cell neoplasms |
| (M8090/3) | Basal cell carcinoma, NOS |
| (8120-8130) | Transitional cell papillomas and carcinomas |
| (8140-8380) | Adenomas and Adenocarcinomas (glands) |
| (M8140/0) | Adenoma, NOS |
| (M8140/3) | Adenocarcinoma, NOS |
| (M8142/3) | Linitis plastica |
| (M8151/0) | Insulinoma, NOS |
| (M8152/0) | Glucagonoma, NOS |
| (M8153/1) | Gastrinoma, NOS |
| (M8155/3) | Vipoma |
| (M8160/3) | Cholangiocarcinoma |
| (M8170/3) | Hepatocellular carcinoma, NOS |
| (M8200/3) | Adenoid cystic carcinoma |
| (M8240/1) | Carcinoid tumor, NOS, of appendix |
| (M8271/0) | Prolactinoma |
| (M8290/0) | Oncocytoma |
| (M8290/0) | Hurthle cell adenoma |
| (M8312/3) | Renal cell carcinoma |
| (M8312/3) | Grawitz tumor |
| (M8360/1) | Multiple endocrine adenomas |
| (M8380/0) | Endometrioid adenoma, NOS |
| (8390-8420) | Adnexal and Skin appendage Neoplasms |
| (8430-8439) | Mucoepidermoid Neoplasms |
| (8440-8490) | Cystic, Mucinous and Serous Neoplasms |
| (M8440/0) | Cystadenoma, NOS |
| (M8480/6) | Pseudomyxoma peritonei |
| (8500-8540) | Ductal, Lobular and Medullary Neoplasms |
| (8550-8559) | Acinar cell neoplasms |
| (8560-8580) | Complex epithelial neoplasms |
| (M8561/0) | Warthin's tumor |
| (M8580/0) | Thymoma, NOS |
| (8590-8670) | Specialized gonadal neoplasms |
| (M8590/1) | Sex cord-stromal tumor |
| (M8600/0) | Thecoma, NOS |
| (M8620/1) | Granulosa cell tumor, NOS |
| (M8630/1) | Arrhenoblastoma, NOS |
| (M8631/0) | Sertoli-Leydig cell tumor |
| (8680-8710) | Paragangliomas and Glomus tumors |
| (M8680/1) | Paraganglioma, NOS |

Carcinoma cell lines from relevant carcinomas include, for example, MDA-MB-231/luc and MDA-MB-468/luc (breast cancer), MiaPaCa-2/luc and SW1990/luc (pancreatic cancer), PC-3/luc (prostate cancer), UMSCC-11B/luc and NA/luc (head and neck cancer) and HT-29/luc (colon cancer). Stem cells represent 4-11% of the total cell populations in the various carcinomas.

Once a stem cell population is identified through sorting and tumor initiation assays, one can determine whether other targeted toxins among highly selective ligand-directed toxins are useful in killing these cancer stem cells. For example, one can combine CD133KDEL with targeted toxins recognizing other cancer stem cells in nude mouse models. In principle, we already have shown this approach has value since dCD133KDEL recognizing the CD133+ cancer stem cells combined with EGF4KDEL had superior anti-carcinoma effects in vivo. Also, since cancer stem cells are often more drug resistant to chemotherapeutic agents than more differentiated cancer cells, one can test combination therapies that involve administering a scFv-TT fusion in combination with one or more chemotherapeutic agents against various cancer stem cells.

As a follow-up to the identification of secondary cancer stem cell populations, one can use the general scFv-TT model established with the construction of the dCD133KDEL to produce targeted toxins directed against other cancer stem cell populations. For example, in vivo data suggests that a combined therapy using dCD133KDEL, described above, and a corresponding scFv-TT fusion that targets EGFR (dEGF4KDEL), expressed by a cohort of cancer stem cells remaining after CD133+ cancer stem cells are eliminated, exhibits superior anti-carcinoma effects than dCD133KDEL alone.

Thus, a scFv-TT fusion can include any suitable targeting scFv that specifically binds to a marker expressed by a target cell population. Suitable markers for a stem cell population include, for example, CD133, CD44, EpCAM (epithelial cell adhesion molecule). EGFR (epidermal growth factor receptor, e.g., a HER1, a HER2, a HER3, or a HER4), uPAR (urokinase receptor), PSCA (prostate stem cell antigen), mesothelin, and MUC1 (mucin 1).

Also, the targeted toxin (TT) portion of the fusion can include any suitable therapeutic moiety. Suitable therapeutic moieties can include compounds that exert direct or indirect cytotoxic activity such as, for example, a small molecule, a radiological agent, and/or a toxic polypeptide. A toxic polypeptide can include, for example, a Diphtheria toxin, a Pseudomonas exotoxin A, a Pseudomonas exotoxin (PE), bryodin, gelonin, α-sarcin, aspergillin, restrictocin, angiogenin, saporin, abrin, a prokaryotic ribonuclease, a eukaryotic ribonuclease, ricin, pokeweed antiviral protein (PAP), a pro-apoptotic polypeptide, a ribosomal inhibitory protein, or a biologically active fragment of any of the foregoing. A pro-apoptotic polypeptide can be, e.g., Bax, Fas, Bad, Bak, Bim, Bik, Bok, Hrk, FasL, TRAIL, or TNF-α.

A suitable therapeutic moiety also can include, for example, a biodegradable nanoparticle that contains one or more therapeutic materials (e.g., cytotoxic compounds). Example 21 demonstrates that a CD133 monoclonal antibody can be coupled to a nanoparticle carrying a functional molecule (6-coumarin) and that the functional can retain its function after the nanoparticle is conjugated to the monoclonal antibody. Moreover, FIG. 21 demonstrates that the targeting moiety, in this case CD133, can cause target-directed cellular uptake of the antibody-nanoparticle, demonstrating the utility of the antibody-nanoparticle for targeted diagnostic and/or targeted therapeutic applications.

For example, a nanoparticle designed to be biodegradable, coupled to an antibody, and designed to contain a therapeutic compound. The antibody-nanoparticle composition may be administered to a subject systemically yet provide target-specific delivery to cells expressing a ligand of the antibody. Once taken up by a target cell, the nanoparticle can degrade, releasing the therapeutic compound inside the target cell. This can minimize systemic exposure of the therapeutic compound and, therefore, limit contact between the therapeutic compound and non-target cells. Of course, a nanoparticle may, like any other therapeutic moiety, be coupled to either a monoclonal antibody or an scFv thereof that is appropriate for an intended target cell population.

Deimmunized Toxin

Although their enzymatic nature renders targeted toxins among the most-effective single cell killers, they are immunogenic so that administering targeted toxins to a patient can result in anti-toxin antibodies that limit the targeted toxin's effectiveness. This has been a particular problem in the case of solid tumor studies where the patient immune system is intact. In one carcinoma study, anti-toxin responses occurred in all treated patients. To address this issue, we synthesized our anti-tumor stem cell drug using a toxin in which immunogenic amino acids were mutated using site-specific mutagenesis.

Figure 5:
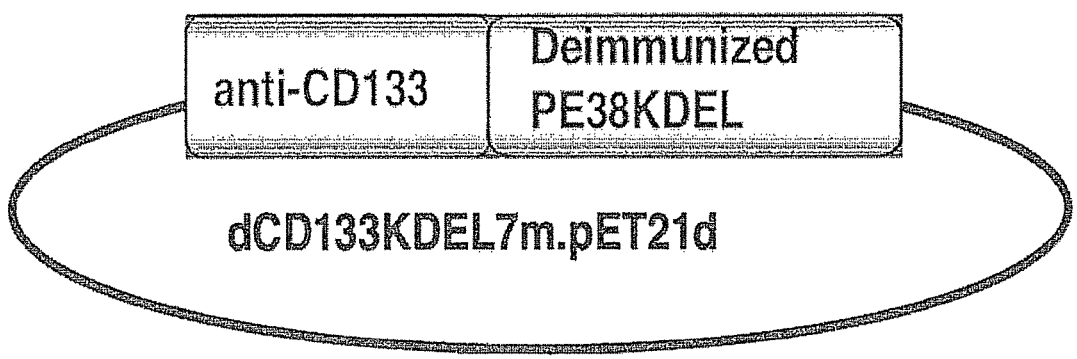
FIG. 5: The deimmunized CD133KDEL gene consists of the anti-CD133 scFV spliced to downstream PE38 with a terminal KDEL sequence.

We deimmunized the toxin on EGF4KDEL, a bispecific ligand-directed toxin (BLT) consisting of human cytokines EGF and IL-4 spliced to truncated pseudomonas exotoxin, using the epitope mapping strategy of Onda et al., "An Immunotoxin with Greatly Reduced Immunogencity by Identification and Removal of B Cell Epitopes," PNAS 2008 Aug. 12; 105(32):11311-11316. Epub 2008 Aug. 4. The terminal endoplasmic retention sequence KDEL was placed on the c-terminus to enhance drug potency. Our dEGF4KDEL is a powerful drug against breast, lung, prostate, pancreatic, and colorectal cancer. Thus, we have a drug that can be given repeatedly without generating an anti-toxin immune response that negates the efficacy of the drug. This same toxin cassette was used to synthesize dCD133KDEL (FIG. 5).

Figure 6:
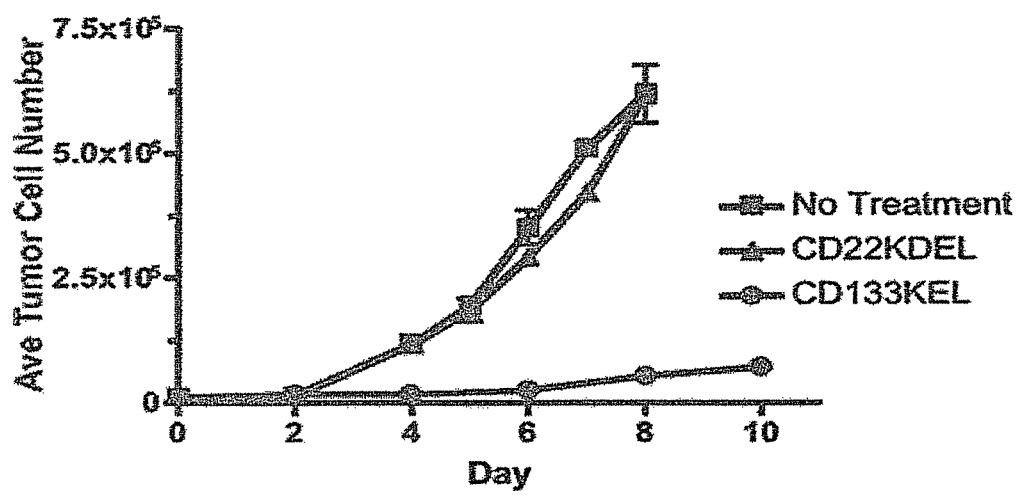
FIG. 6: Trypan blue viability assay in which viability is measured daily in cultured cells. UMSCC-11B head and neck cancer cells were treated with either dCD133KDEL (CD133KDEL) or control anti-B cell targeted toxin CD22KDEL.

We continuously cultured carcinoma cells in the presence of dCD133KDEL. Originally, we used radiolabeled thymidine uptake assays or leucine incorporation protein synthesis assays to measure activity, but this only measured activity on a single day. Thus, we devised an assay that would permit the continuous culture of the cancer cells in the presence of drug. We cultured dCD133KDEL in the presence of drug for several days and each day we changed media and counted viable cells by trypan blue dye exclusion. Surprisingly, FIG. 6 shows that dCD133KDEL was highly effective in inhibiting UMSCC-11B head and neck cancer cell growth measured by vital dye exclusion. The dCD133KDEL killed the cells at a concentration of 0.3 nM.

Figure 7:
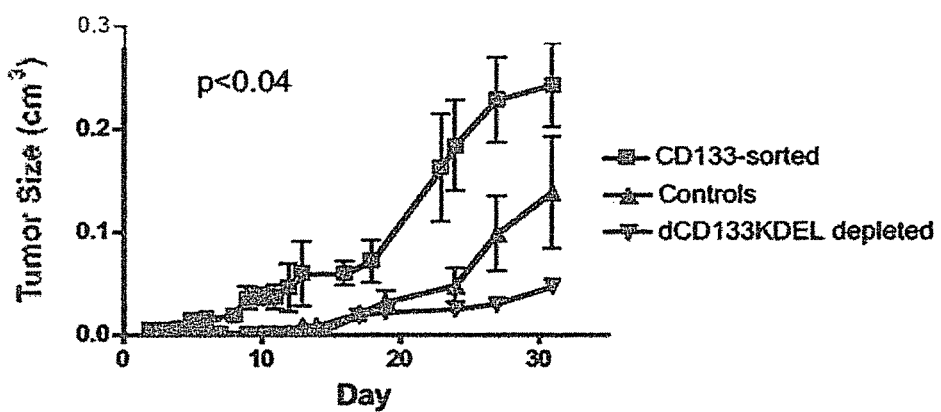
FIG. 7: The dCD133KDEL fusion protein prevents tumor initiation which is a characteristic of tumor stem cells. Tumor initiation assay in which sorted cells are injected into the flank of nude mice. The graph shows the rate of tumor growth for those tumors that grow. P value indicates the significance of the difference between the sorted and non-sorted (control) group.

FIG. 7 shows a tumor initiation assay in which CD133+ head and neck cancer cells UMSCC-11B cells were sorted using our CD133 scFv affixed to magnetic beads and then purified using a MAGS magnetic bead kit (STEMCELL Technologies, Inc., Vancouver, British Columbia, Canada).

Putative stem cells are injected into the flank of nude mice. If they are enriched stem cells, then they will grow at an accelerated rate with a higher level of tumor takes than non-stem cells. FIG. 7 shows that the sorted cells had the highest incidence of tumor initiation (75%), and these tumors had an average tumor growth significantly higher than that obtained with unsorted tumor cells (p<0.04). This provides evidence that CD133scFv does indeed recognize tumor stem cells. Interestingly, when a sample of cells was treated with dCD133KDEL prior to injection, these cells had the slowest growth rate and only 1 of 4 tumors grew. This verifies that our CD133scFv is indeed enriching cancer stem cells.

Figure 8:
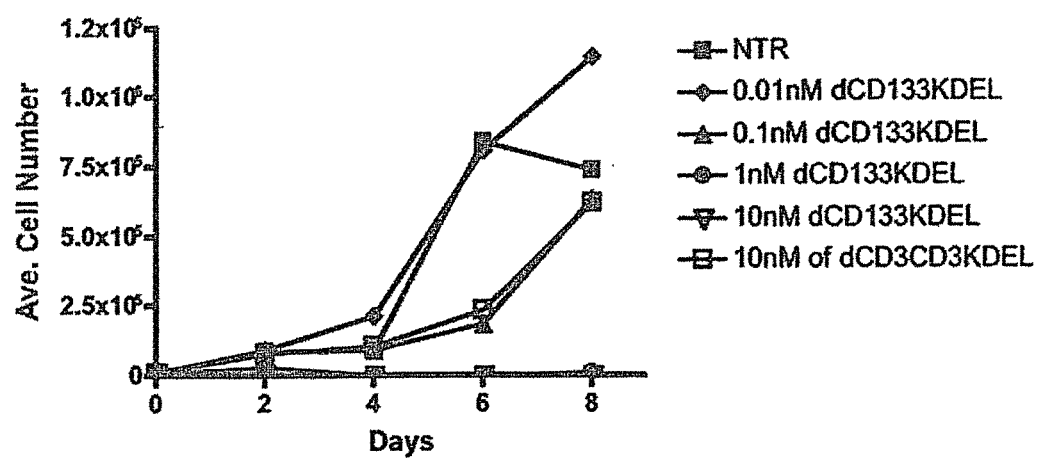
FIG. 8: Trypan blue viability assay measuring the effect of dCD133KDEL on cultured MDA-MB-231 cells over time. NTR—No treatment.

Other carcinomas are affected by dCD133KDEL treatment. CD133+ cancer stem cells have been identified in breast cancer and our flow cytometry studies indicate the presence of cancer stem cells in the breast cancer cell line MDA-MB-231. Therefore, just as in FIG. 6, we cultured MDA-MB-231 cells in the presence of dCD133KDEL and viability measured daily with trypan blue. FIG. 8 shows that dCD133KDEL markedly inhibited breast cancer cells, but control CD3CD3KDEL did not. CD3CD3KDEL recognizes CD3 epsilon T cell receptor. Thus, killing was specific.

Additional cancer stem cells markers may be identified so that the same strategy just described in connection with CD133 may be used to generate targeted toxin drugs that are specific to other cohorts of cancer stem cells. We have already identified EGFR and EpCAM as additional relevant cancer stem cells markers. Additional cancer stem cell markers may be identified using standard, routine techniques. Suitable techniques include, for example, analysis using the Antibody Array 500 (Clontech Laboratories, Inc., Mountain View, Calif.). Such antibody arrays provide a measure of relative protein abundance between samples.

Thus, in certain embodiments, the scFv-TT fusion can include a deimmunized targeted toxin portion. As used herein, "deimmunized" and variants thereof refer to amino acid sequences carrying one or more amino acid substitutions that (a) reduce the anti-toxin immune response by one to whom the toxin is administered, and (b) retains a therapeutically and/or prophylactically effective amount of toxin activity.

Using the deimmunizing strategy described above, we have observed significant anti-toxin antibody reductions and significant in vivo anti-cancer responses for three different scFv-TT fusions, also known as bispecific ligand directed toxins: deimmunized 2219KDEL7mut for leukemia therapy, deimmunized EGF4KDEL7mut for carcinoma therapy, and deimmunized EGFATFKDEL for glioma therapy. For example, to determine the extent to which the anti-toxin immune response is decreased using deimmunized 2219KDEL (referred to herein as 2219KDEL 7mut, d2219KDEL, or 2219ARLKDEL 7mut (e.g., in FIG. 11)), immunocompetent mice were used as a model of human immunogenicity because sera from human patients receiving pseudomonas exotoxin (PE)-based drugs recognize the same prominent immunogenic regions of PE as mice.

The deimmunized 2219KDEL7mut fusion polypeptide was expressed from a fusion gene synthesized using assembly PCR. In its final configuration, the 2219ARLKDEL fusion gene (from 5' end to 3' end) consisted of an EcoRI restriction site, then the anti-CD22 scFv gene. This anti-CD22 scFv gene was oriented with the $V_L$ domain preceding the $V_H$ domain and was conjoined by a fragment encoding the ARL linker (GSTSGSGKPGSGEGSTKG, SEQ ID NO:69). Next, a $G_4S$ linker (GGGGS) followed by anti-CD19 scFv (in the same $V_L/V_H$ orientation and same ARL linker) was cloned and then a downstream seven amino acid EASGGPE linker. The linker was followed by PE38 (360 aa) with its C-terminal REDLK replaced with the ER retention sequence KDEL, and finally, a NotI restriction site at the 3' end. The resultant 2650 bp EcoRI/NotI fragment gene was spliced into the pET21d bacteria expression vector under control of an isopropyl-b-D-thiogalactopyranoside (IPTG) inducible T7 promoter. DNA sequencing analysis (Biomedical Genomics Center, University of Minnesota) was used to verify that the gene was correct in sequence and cloned in frame. To create a mutated 2219ARLKDEL molecule (2219ARLKDEL7mut) with decreased immunogenicity, eight amino acids distributed among the seven major epitopes on $PE_{38}$ KDEL were mutated using the QuickChange Multi Site-Directed Mutagenesis Kit (Stratagene. La Jolla Calif., USA) and were confirmed by DNA sequencing. The following immunogenic, hydrophilic amino acids were altered: R490A, R513A, R467A, E548S, K590S, R432G, Q332S, R313A and confirmed by DNA sequencing.

The deimmunized EGFATFKDEL fusion polypeptide was expressed from a fusion gene synthesized using DNA-shuffling and DNA cloning techniques. In its final configuration, the EGFATFKDEL fusion gene (from 5' end to 3' end) consisted of an NcoI restriction site, an ATG initiation codon, the genes for human EGF, the downstream 135-amino terminal fragment (ATF) from uPA linked by a 20 amino-acid segment of human muscle aldolase (HMA), the 7 amino-acid EASGGPE linker, the first 362 amino acids of the pseudomonas exotoxin (PE) molecule with KDEL replacing the REDLK at the C terminus, and a NotII restriction site at the 3' end of the construct. The HMA segment was incorporated into the molecule as a flexible, non-immunogenic linker. The use of the ATF gene fragment was previously described by our laboratory. The resultant 1748 bp NcoI/NotII fragment gene was spliced into the pET28c bacteria expression vector under control of an isopropyl-b-D-thiogalactopyranoside inducible T7 promoter. DNA sequencing analysis (Biomedical Genomics Center, University of Minnesota) was used to verify that the gene was correct in sequence and had been cloned in frame. To create an EGFATFKDEL molecule with decreased immunogenicity, eight amino acids representing the seven major epitopes on PE38 were mutated using the QuickChange Site-Directed Mutagenesis Kit (Stratagene. La Jolla Calif.). The following amino acids were altered: R490A, R513A, R467A, E548S, K590S, R432G, Q332S, R313A and confirmed by DNA sequencing.

Figure 11:
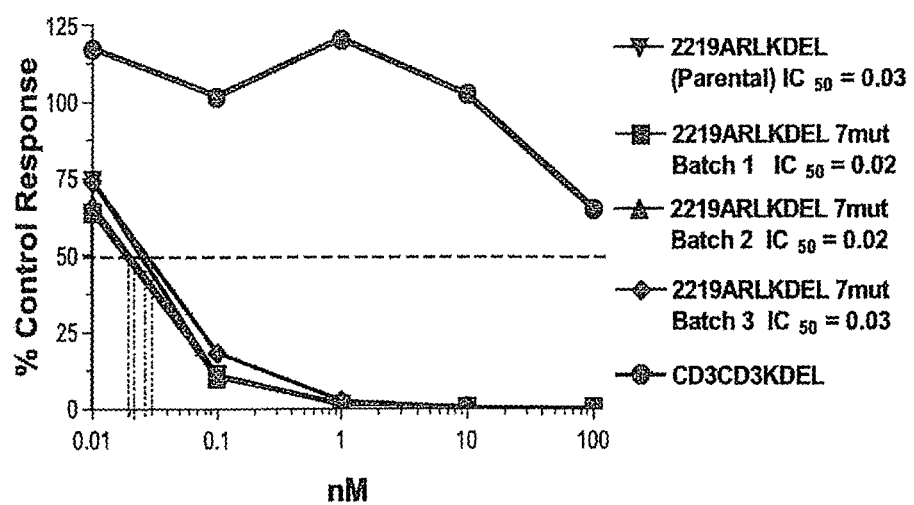
FIG. 11: $^3$H-thymidine uptake assays showing no activity loss when the mutated (2219ARLKDEL 7mut, Batch 1, Batch 2, and Batch 3) and non-mutated forms (2219AR-LKDEL (Parental)) were compared against Daudi cells. Cell killing was the same after 48 hours for all 3 batches of mutated and 1 batch of non-mutated drug.
Figure 12:
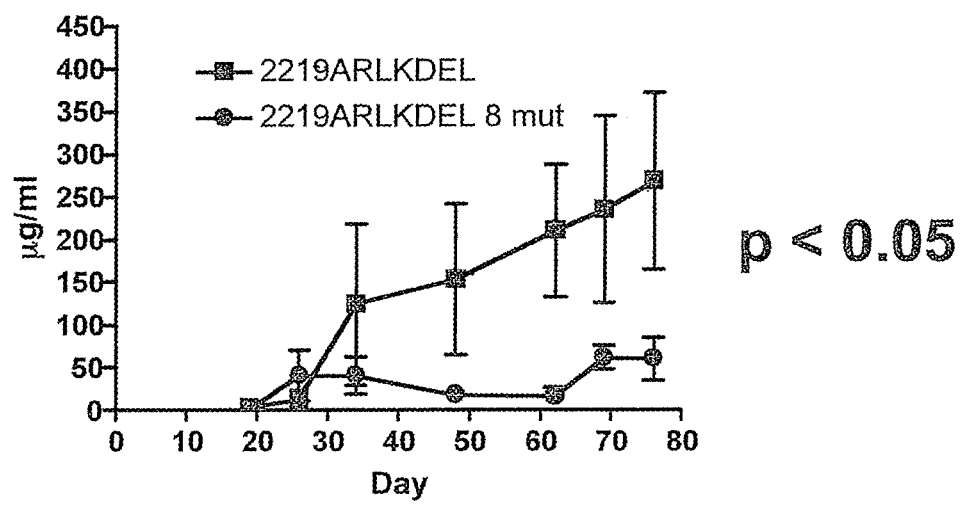
FIG. 12: Groups of normal mice were immunized weekly with mutated or non-mutated drug. Animals were bled and serum tested weekly for anti-toxin antibody using ELISA. Values were averaged and then analyzed by Student T test. Curves were significantly different ($p<0.05$).
Figure 13:
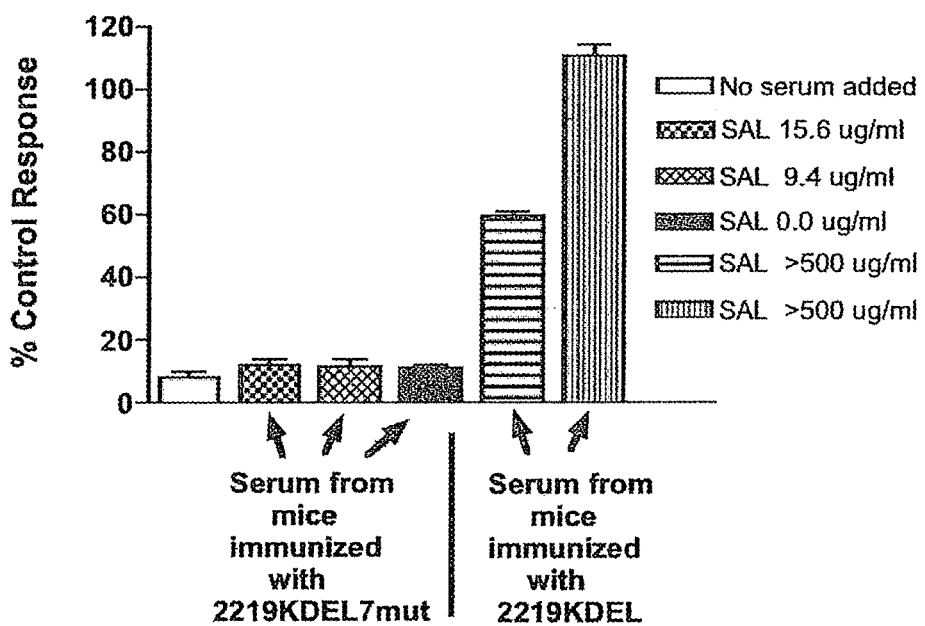
FIG. 13: The ability of serum samples from mice in FIG. 12 to neutralize the killing of a fixed amount of 2219KDEL. Serum was taken from four 2219KDEL7mut-immunized mice and two mice immunized with non-mutated 2219KDEL, then incubated with 0.2 nM 2219KDEL. Serum from the 2219KDELmut7 mice did not block cell killing by 2219KDEL.
Figure 14:
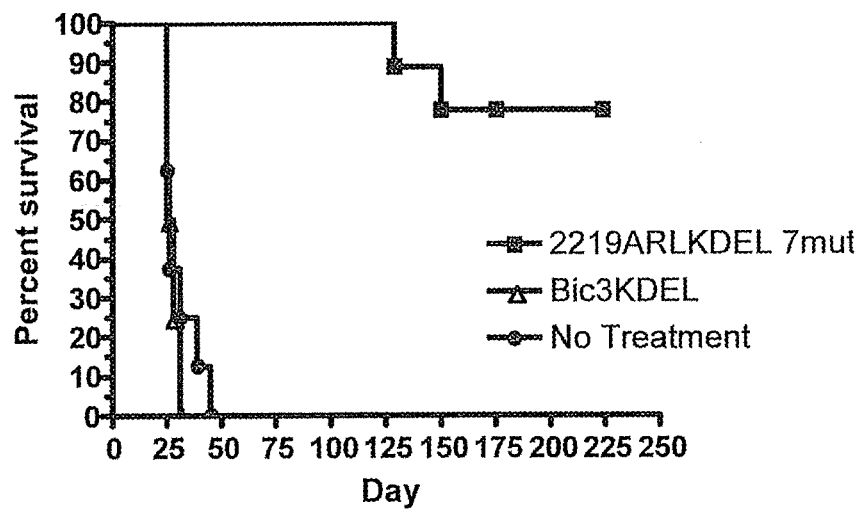
FIG. 14: Mice with systemic B cell disease were treated with mutated 2219KDEL7mut. Eighty percent of these were disease free survivors. Controls all died.

FIG. 11 shows that mutation did not affect drug activity compared to non-mutated parental drug. In FIG. 12, immunization studies with immunocompetent BALB/c mice were conducted to compare the immunogenicity of 2219ARLKDEL7mut compared to the parental 2219ARLKDEL molecule. Mice (n=6/group) were immunized and bled weekly for a total of nine weeks (10 injections). Serum samples from each animal were analyzed using ELISA to detect anti-PE38(KDEL) IgG. FIG. 12 shows that after nine (day 69) or 10 injections (day 76) with a clinical amount (10 μg/kg of drug), the level of anti-toxin IgG generated against deimmunized mutant (2219ARLKDEL8mut) was 20%-25% of the anti-toxin IgG generated against the non-mutated parent (2219ARLKDEL). Thus, mice given multiple injections of the deimmunized drug generated significantly lower anti-toxin levels than those injected with equal amount of parental form of the drug (p<0.05). Thus, one can give multiple injections of the deimmunized form of the drug and generate a limited anti-toxin immune response in a murine model that has been verified as a model of human immunogenicity. FIG. 13 shows that serum from mice immunized with non-deimmunized drug mice neutralized 2219KDEL killing in vitro. Serum from mice immunized with deimmunized drug did not neutralize 2219KDEL killing in vitro. Thus, multiple dosing with 2219KDEL7mut produces less neutralizing anti-toxin antibodies than multiple dosing with the non-deimmunized parental form. Finally, FIG. 14 shows that mutated drug elicited a powerful anti-cancer effect against systemic B cell malignancy using a system Raji-luc/scid mouse model in which tumor is injected intravenously. Survivors were verified as disease free as described in Vallera et al., "Bioengineering a unique deimmunized bispecific targeted toxin that simultaneously recognizes human CD22 and CD19 receptors in a mouse model of B-cell metastases," Mol Cancer Ther. 2010 June; 9(6):1872-83. Epub 2010 Jun. 8.

Figure 15:
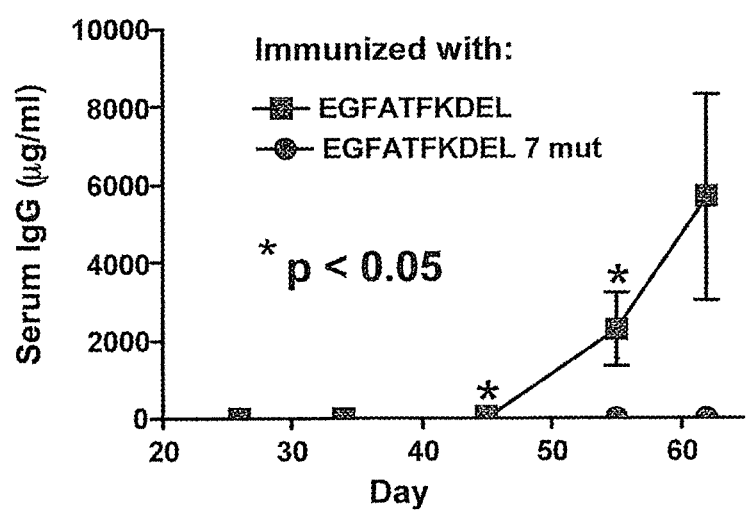
FIG. 15: Immunocompetent B6 mice (n=5/group) were immunized weekly with EGFATFKDEL 7mut and non-deimmunized EGFATFKDEL. Serum was removed weekly and anti-toxin (PE) levels were determined in sensitive ELISA assay. The response was significantly inhibited.

The data discussed immediately above was generated using deimmunized PE toxin by carrying eight amino acid substitutions located among the seven major subgroups associated with toxin immunogenicity by epitope mapping. The mutations were Q332S in epitope 1, R467A in epitope 2a, R313A in epitope 3, R432G in epitope 4a, R490A in epitope 5, R513A and E548S in epitope 6a, and K590S in epitope 7. A topographical epitope map of PE38 was generated using a mutual competition assay employing a panel of 60 monoclonal antibodies to various determinants of the toxin. With our most recent drugs, there was an 80% reduction in immune response after 12 or 14 weekly immunizations (FIG. 15).

The same approach may be taken to generate a deimmunized form of CD133KDEL (dCD133KDEL), which has demonstrated efficacy in vivo.

The activity of deimmunized variants may be screened using the trypan blue viability assay described herein. The cytolytic activity of a deimmunized scFv-TT construct can be compared to the non-deimmunized parental form. The cytolytic curves generated from these assays are highly reproducible. No statistically significant loss of activity has been observed with deimmunized versions of d2219KDEL, dEGF4KDEL, and dEGFATFKDEL. Thus, the deimmunization approach described herein appears to be generally applicable.

Deimmunization causes a drop in serum antibody levels in two different mouse strains with two different MHC haplotypes. This is relevant because different MHC molecules differ in their presentation of peptide fragments in the MHC groove and one haplotype might present different peptides than another. Thus, a potential problem with mutating B cell recognizing regions is that different MHC polymorphisms may recognize antigen differently. Deimmunization results, however, in significant anti-toxin reductions in both BALB/c (H-2d) and C57BL/6 (H-2b) strains. Therefore, this indicates that the strength of mutating all seven regions was enough to overcome these possible MHC differences. Moreover, anti-PE antibodies from BALB/c mice hyperimmunized with PE reacted with similar epitopes in humans, suggesting that the same B cell epitopes were recognized with distinct T cell support.

Targeting Stem Cells with Targeted Toxins

Figure 9:
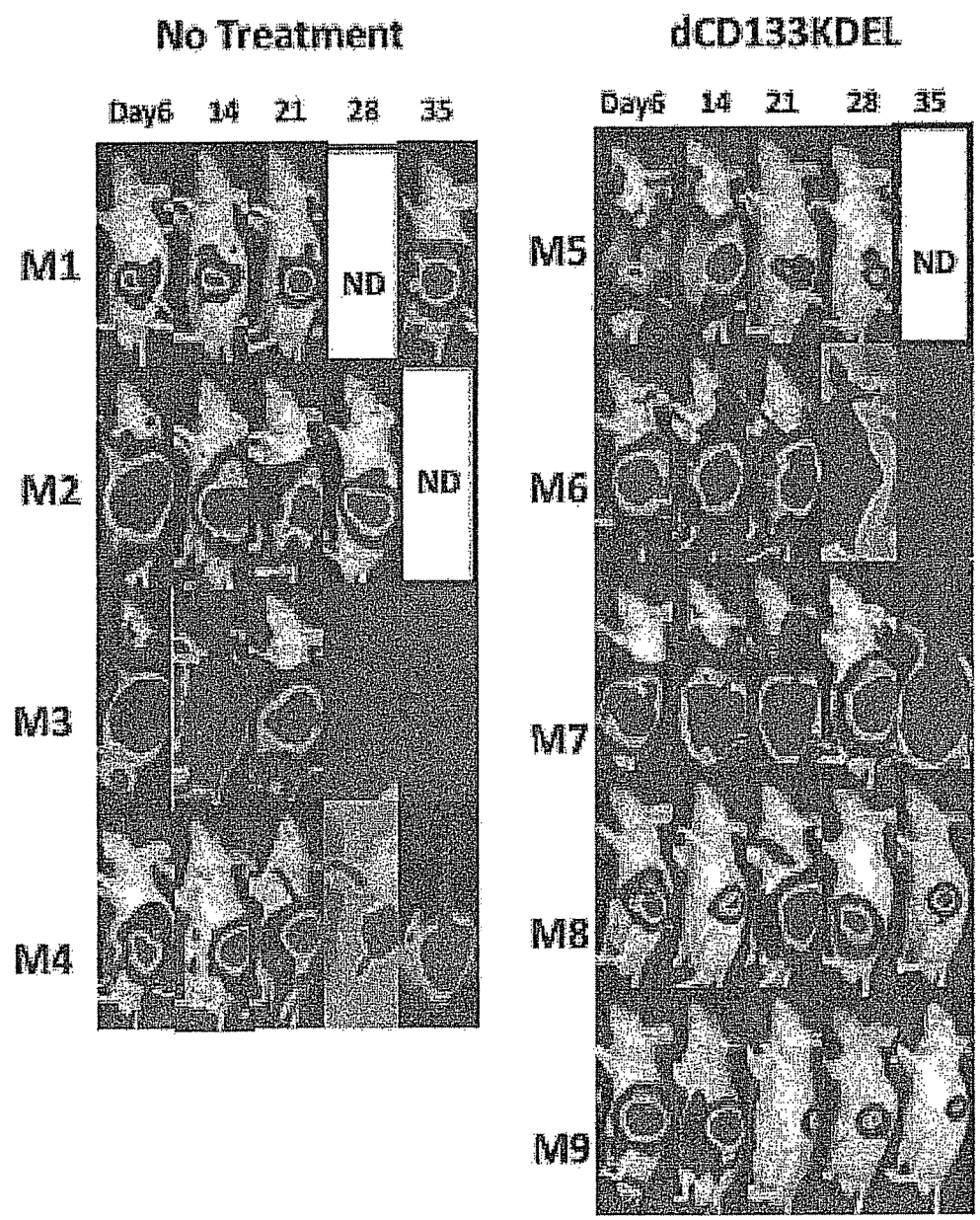
FIG. 9: The effect of dCD133KDEL on tumor progression in mice with systemic MDA-MB-231 tumors. Systemic tumors were induced in nude mice by giving 2 million cells via intrasplenic injection. Treatment of mice was begun on Day-6 post-tumor inoculation with dCD133KDEL. A single course of treatment consisted of an injection of 20 µg of drug given every other day (MWF) and mice were given 6 courses of treatment. Animals were imaged weekly. Bioluminescence intensity was measured as a function of photons/$sec/sr/cm^2$. Controls were untreated.

One strategy for eliminating cancer stem cells involves target-specific depletion. Our in vivo models allow one to measure the effects of targeted toxin against systemic carcinoma in vivo in real time by bioluminescent imaging. All of the carcinomas chosen for our studies have been transfected with the luciferase gene and grow exceptionally well in nude mice. In FIG. 9, we used our established MBA-MB-231 breast cancer model of systemic tumor growth in nude mice. Four million cells are surgically injected into the spleens of nude mice on Day 0. Treatment with dCD133KDEL was begun on Day 6. Weekly courses of MWF were given (20 µg/injection) for five weeks. The study shows that in vivo injection of dCD133KDEL resulted in an anti-tumor effect in 60% of the mice over the course of 35 days. Control mice given anti-T cells drug (CD3CD3KDEL) showed no effect (not shown). Together, these data provide evidence that dCD133KDEL is recognizing and killing tumor stem cells. Moreover, despite the fact that CD133+ cancer stem cells make up a low percentage of the tumor cell population, the general anti-tumor effects of dCD133KDEL are pronounced.

Figure 10:
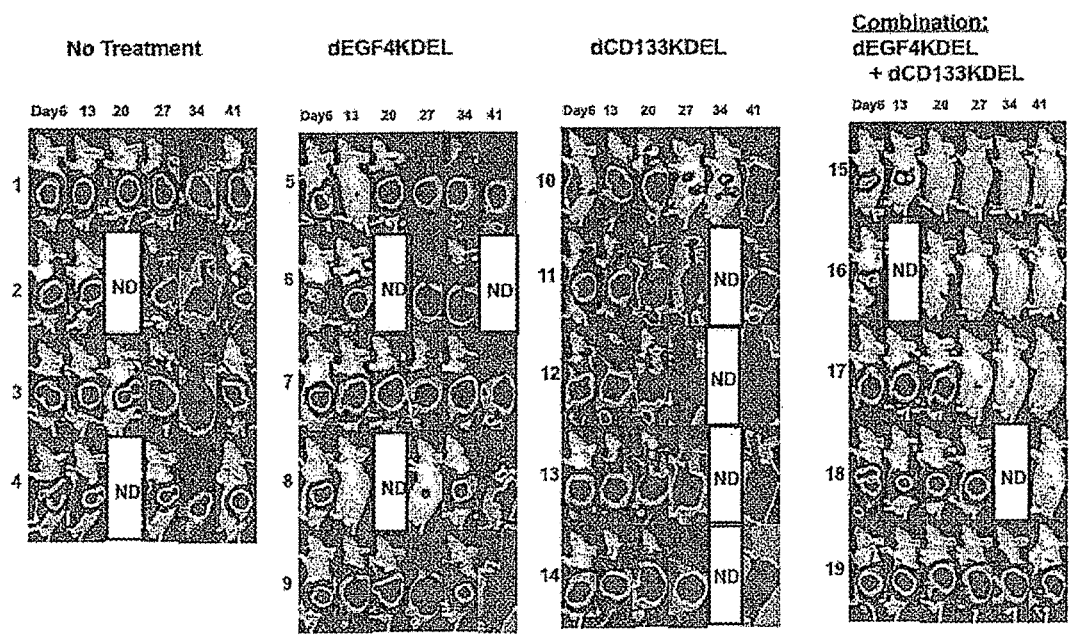
FIG. 10: Bioluminescence analysis of tumor progression in mice treated with dCD133KDEL, dEGF4KDEL, or a mixture of both.

Thus, cancer stem cells are a particularly effective target for scFv-TT therapy that is extendable to other subpopulations of cancer stem cells using scFv directed to other markers specific for those other subpopulations for delivery of targeted toxins. FIG. 10 shows the results of treating carcinoma using a combination of dCD133KDEL to destroy CD133+ cancer stem cells and then dEGF4KDEL to eliminate a second stem cell population, cancer stem cells expressing EGFR. As part of the experimental design, groups shown in FIG. 9 were treated with suboptimal dose of dCD133KDEL, a suboptimal dose of EGF4KDEL, or a combination of both suboptimal doses. When both agents were tested individually, the imaging data below showed only slight effects. When both agents were combined in the exact same doses and schedules, 4 of 5 animals showed complete responses with long-term disease free survivors indicating superior effects with combined treatment supporting the existence of another stem cell population besides CD133+ cancer stem cells.

A second strategy for eliminating cancer stem cells involves treatment with a scFv-TT fusion combined with established chemotherapeutic agents. Numerous studies show that targeted toxins are far more effective when combined with chemotherapy. Such combination therapies may be performed using any suitable chemotherapeutic agent. Suitable chemotherapeutic agents include, for example, alkylating agents such as, for example, cisplatin carboplatin, oxaliplatin, mechlorethamine, cyclophosphamide, chlorambucil, or ifosfamide; anti-metabolites such as, for example, azathioprine or mercaptopurine; plant alkaloids or terpenoids such as, for example, vinca alkaloids (e.g., vincristine, vinblastine, vinorelbine, vindesine, etc.), podophyllotoxin (e.g., etoposide or teniposide), or taxanes (e.g., paclitaxel); topoisomerase inhibitors such as for example Type 1 topoisomerase inhibitors (e.g., irinotecan or topotecan) or Type 2 topoisomerase inhibitors (e.g., amsacrine, etoposide, etoposide phosphate, or teniposide); or antineoplastics such as, for example, dactinomycin, doxorubicin, epirubicin, or bleomycin.

Formulations

A monoclonal antibody, scFv, polynucleotide, mAb-fusion, or scFv-fusion of the invention may be provided in a composition that can further include a pharmaceutically acceptable carrier. "Pharmaceutically acceptable" refers to a diluent, carrier, excipient, salt, etc, that is compatible with the other ingredients of the composition, and not deleterious to the recipient thereof. Typically, the composition includes a pharmaceutically acceptable carrier when the composition is used as described herein. The compositions of the present invention may be formulated in pharmaceutical preparations in a variety of forms adapted to the chosen route of administration, including routes suitable for stimulating an immune response to an antigen. Thus, a composition of the present invention can be administered via known routes including, for example, oral; parenteral including intradermal, transcutaneous, subcutaneous, intramuscular; intravenous; intraperitoneal, etc.; and topically, such as, intranasal, intrapulmonary, intramammary, intravaginal, intrauterine, intradermal, transcutaneous, and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

Exemplary embodiments of the invention include:

1. The hybridoma identified herein as Hybridoma Clone 7.

2. A monoclonal antibody produced by Hybridoma Clone 7.

3. A single-chain variable-fragment (scFv) of a monoclonal antibody produced by Hybridoma Clone 7.

4. The scFv of embodiment 3 comprising the amino acid sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58.

5. The scFv of embodiment 4 wherein the scFv comprises the amino acid sequence of SEQ ID NO:58.

6. An isolated polynucleotide comprising a nucleotide sequence that encodes the amino acid sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58.

7. The isolated polynucleotide of embodiment 6 wherein the isolated polynucleotide comprises a nucleotide sequence that encodes the amino acid sequence of SEQ ID NO:58.

8. The isolated polynucleotide of embodiment 7 wherein the isolated polynucleotide comprises the nucleic acid sequence of SEQ ID NO:57.

9. A composition comprising the monoclonal antibody of embodiment 1 or embodiment 2.

10. A composition comprising the scFv of any one of embodiments 3-5.

11. A fusion polypeptide comprising:
a targeting moiety comprising:
the monoclonal antibody of embodiment 2; or
the scFv of any one of embodiments 3-5; and
a toxin moiety comprising a therapeutically active portion of a cytolytic toxin.

12. The polypeptide of embodiment 11 wherein the toxin moiety is deimmunized.

13. A composition comprising:
a first fusion polypeptide of embodiment 11; and
a second fusion polypeptide comprising:
a second fusion polypeptide of embodiment 11; or
a fusion polypeptide comprising a monoclonal antibody or scFv thereof that specifically binds to a second marker differentially expressed by cancer stem cells.

14. The composition of embodiment 13 wherein at least one marker differentially expressed by cancer stem cells comprises CD133.

15. The composition of embodiment 13 or embodiment 14 wherein at least one marker differentially expressed by cancer stem cells comprises EGFR.

16. A method comprising:
administering to a subject in need of such treatment a therapeutically effective amount of:
the monoclonal antibody of embodiment 2;
the scFv of any one of embodiments 3-5;
the fusion polypeptide of embodiment 11 or embodiment 12; or
the composition of any one of embodiments 9, 10, or 13-15.

17. The composition of embodiment 9 further comprising a nanoparticle coupled to the monoclonal antibody.

18. The composition of embodiment 10 further comprising a nanoparticle coupled to the scFv.

19. A composition comprising a detectable marker coupled to:
the monoclonal antibody of embodiment 2, or
the scFv of any one of embodiments 3-5.

20. A method comprising:
contacting the composition of embodiment 19 with at least one cell that expresses CD133; and
detecting a complex comprising at least a portion of the composition specifically bound to the at least one cell that expresses CD133.

21. The method of embodiment 20 wherein the contacting comprises administering the composition to a subject comprising cancer stem cells that express CD133.

22. The method of embodiment 20 wherein detecting a complex comprising at least a portion of the composition specifically bound to the at least one cell that expresses CD133 indicates that the subject has or is at risk of having a neoplastic condition.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Cell Culture

Caco-2 cells were grown in Minimum Essential Medium (MEM) containing 20% FBS, 1% non-essential amino acids (Sigma-Aldrich Corp., St. Louis, Mo.), 1% sodium pyruvate (Sigma-Aldrich Corp., St. Louis, Mo.) and 1% penicillin-streptomycin. GBM6 cells were derived from a surgically isolated glioma specimen; these cells were grown in serum-free DMEM/F12 media supplemented with B27, N2, and 20 ng/ml EGF and FGF. U87 cells were cultured in Dulbecco's MEM containing 10% FBS and 1% penicillin-streptomycin. All reagents were purchased from Invitrogen (Carlsbad, Calif.) unless indicated otherwise.

Example 2

CD133 Antigen Design and Generation

Human CD133 (NCBI Reference Sequence NM_006017.1) encodes a protein of 865 amino acid residues. About 355 of them were theoretically predicted to be highly immunogenic. A 1065 bp oligonucleotide corresponding to this selected amino acid block was synthesized after incorporating codon optimizations to improve bacterial expression. The oligonucleotide sequence was PCR amplified, cloned into a PET30a vector that had an N-terminal His-tag, sequence verified and then transformed into a BL-21 (DE3) *E. coli* strain. For protein expression, 0.5 liters of transformed bacteria were grown in LB medium and were induced by 0.4 mM IPTG for two hours. The cells were pelleted by centrifugation, resuspended in Tris-HCl lysis buffer, and were disrupted by sonication on an ice bath. Protein expression in supernatant and pellet were analyzed by resolving them in a 12% SDS-PAGE gel and then staining by Coomasie Blue. Recombinant protein was purified from the pellet by using nickel-NTA beads.

Example 3

Immunization and Monoclonal Antibody Production

All animal protocols used in the study were approved by IACUC of the University of Minnesota. Balb/c mice were injected with the recombinant CD133 peptide fragment. Animals were periodically boosted three to four times with the antigen until sufficient serum titer against CD133 was obtained as analyzed by ELISA. Immunized animals were euthanized and their spleen was removed. Splenocytes obtained were fused with myeloma cells using PEG, and were cultured in HAT media. Culture supernatants were screened for the production of antibody against CD133 using ELISA.

Example 4

Screening of Hybridoma Supernatants by Western Blot

Caco-2 cells were lysed in RIPA buffer (Thermo Scientific, Waltham, Mass.) and centrifuged at 10,000 rpm and 4° C. to remove debris. The protein concentration of cell lysates was measured using BCA protein assay kit (Thermo Scientific, Waltham, Mass.), with bovine serum albumin as the standard. The cell lysates were resolved by a 10% SDS-PAGE gel (Bio-Rad Laboratories, Inc., Hercules, Calif.) and transferred onto a nitrocellulose membrane (Whatman Inc., Piscataway, N.J.) using a criterion blotter (Bio-Rad Laboratories, Inc., Hercules, Calif.,). The membrane was blocked with 5% non-fat dry milk in TBST for one hour and then incubated with the hybridoma supernatant or controls (negative control: pre immune serum; positive controls: anti-CD133 antibody, ab 19898 from Abcam and post-immune anti-sera) overnight at 4° C. The membrane was then washed thrice with TBST and then incubated with anti-mouse IgG conjugated to HRP (CalBiochem, San Diego, Calif.) in 5% non-fat dry milk/TBST for one hour at room temperature. The membrane was then washed three times with TBST and visualized using SuperSignal West Pico chemiluminescent substrate (Thermo Scientific, Waltham, Mass.).

Example 5

Immunofluorescence

Caco-2 cells were plated in 16-well chamber slides. After four days of growth, the cells were fixed with 4% paraformaldehyde, washed in DPBS and then incubated in 200 mM glycine for 10 minutes. The cells were then blocked with a solution of 0.5% BSA and 0.2% gelatin in PBS for 10 minutes. This was followed by incubation with hybridoma supernatants or relevant controls (negative control: pre immune serum; positive controls: anti-CD133 antibody, AC141 from Miltenyi Biotec (Auburn, Calif.) and post-immune anti-sera) overnight at 4° C. The cells were washed five times with PBS and then incubated with Alexa 594 coupled anti-mouse IgG for one hour at room temperature. The cells were further washed with PBS and then visualized under a fluorescence microscope. Images were taken using ProgRes C3® software and then processed using Adobe Photoshop.

Example 6

CD133 cDNA Transfection

CD133-IRES GFP or CMV GFP constructs were transfected into U87 cells using FuGENE HD transfection reagent according to the manufacturer's instructions. Briefly, cells were plated in a 10 cm dish. Twelve hours later, 10 µg of the pDNA was diluted in serum-free growth DMEM and mixed with 40 µl of the transfection reagent. Following incubation for 15 minutes, the transfection mix was added to the cells. Forty-eight hours later, cells were harvested using non-enzymatic cell dissociation buffer (Sigma-Aldrich Corp., St. Louis, Mo.) for flow cytometry.

Example 7

FACS Staining

Primary human glioblastoma GBM6 cells, U87, or Caco-2 cells were washed three times and suspended in 100 µl of PBS. Cells were stained with either CD133/2 (293C3) (Miltenyi Biotec, Auburn, Calif.) or 100 µl of Hybridoma Clone 7 supernatant, incubated for 30 minutes at 4° C., washed three times, and then suspended in 100 µl of PBS. Cells were further incubated with 10 µl of anti-mouse hylite 647 (1:40 dilution; American Qualex, San Clemente, Calif.) for 30 minutes at 4° C., washed three times, and analyzed by flow cytometry.

Example 8

Immunohistochemistry

5 µm paraffin sections of human kidney or glioblastoma tissue were mounted onto charged slides. The sections were deparaffinized and rehydrated using standard methods, rinsed in running tap-water and placed in a PBS bath for five minutes. The slides were then incubated in a pre-heated steamer bath with staining dish containing EDTA buffer (pH 8.0) for 30 minutes and then cooled for 20 minutes. The slides were washed with PBS (pH 7.4) for minimum of five minutes and then subjected to following incubation steps: blocking with serum-free background Sniper (Biocare Medical, Concord, Calif.), primary antibody at a 1:200 dilution of hybridoma supernatant at 4° C. overnight, Leica Bond post primary, Leica Bond polymer, and DAB chromagen developer. The sections were rinsed well, counterstained with hematoxylin, dehydrated, sealed with a cover slip and imaged.

Example 9

Tunicamycin Treatment and Analysis

Caco-2 cells were seeded in 6-well plates and treated with 2.5 µg/ml-20 µg/ml tunicamycin or vehicle (medium containing 0.1% DMSO) for three days. Samples were collected each day by removing the medium from a set of wells and lysing the cells in RIPA buffer. The lysates were centrifuged to remove cell debris and then analyzed by western blotting using either Hybridoma Clone 7 or anti-GAPDH (Sigma-Aldrich Corp., St. Louis, Mo.) as primary antibodies.

Example 10

Cloning and Expression of scFv

Summary

A clone scFv gene of a human prominin-1-specific mouse MAb, was generated. Initially, a mouse scFv library was constructed using RNA derived from the hybridoma cell line. Briefly, after total RNA purification and first-strand cDNA synthesis, a unique two-step PCR protocol was used to amplify the scFv-encoding gene repertoire. The VH and VL gene pools were amplified from the synthesized cDNA, separately. The scFv genes were assembled randomly by fusing VH and VL fragments using an over-lap PCR. The scFv cDNA and pCDisplay-4 vector were digested by a single, rarely-cutting restriction enzyme SfiI. After ligation, the recombinant constructs were transformed into electro-competent E. coli XLI-BLUE. After overnight culture at 37° C., the amplified recombinant phagemid was extracted from bacteria and kept at −20° C. The library construction was achieved by only one transformation and had a theoretical size of $1.0 \times 10^7$.

After that, a standard panning process was carried out. The re-amplified library was incubated with human prominin-1 pre-coated in 96-well plate for 1-2 hours at 37° C. After multiple washes, the binding phage antibody was eluted with a low pH buffer. The retrieved recombinant phages were amplified in E. coli for the next round of panning. After 3 rounds of panning, 30 randomly picked-up clones were checked for their reactivity against prominin-1 by phage ELISA, and nine positive clones were identified. The DNA sequencing results showed that five of them were identical, suggesting that they are all derived from the single hybridoma clone: a hybridoma cell line that secretes anti-prominin-1 MAb.

One of them, No. 11 clone, was transformed into E. coli Top10F' for expression. Soluble expression of scFv was achieved by utilizing E. coli secretion machinery and induced at low temperature (30° C.). The expressed scFv was found mainly in the culture medium and periplasmic space of E. coli.

Soluble scFv ELISA was performed to confirm the binding specificity to the target protein. The recombinant No. 11 scFv, expressed both in culture medium and periplasmic space, was specific for human prominin-1 protein, although the binding signal is lower than the positive control, the parent intact bivalent antibody.

In conclusion, we were able to successfully clone the scFv gene/cDNA from the selected hybridoma clone.

Materials and Reagents

Antigen: human prominin-1 expressed in E. coli as a 6*HIS fusion protein.

Hybridoma cell line: anti-human C-prominin-1 murine monoclonal antibody (No. 7).

EIA/RIA stripwell 96-well plates: Corning (New York, N.Y.)

Enzymes:
RT: SuperScript II Reverse Transcriptase, Invitrogen (Carlsbad, Calif.)
ExTaq: Takara Co. (Shiga, Japan)
T4 ligase: Invitrogen (Carlsbad, Calif.)
Restriction enzyme: SfiI, Roche (Basel, Switzerland)

E. coli XLI-Blue host strain: From Stratagene (La Jolla, Calif.). XLI-Blue is a suppressor strain, in which the amber stop codon would not be recognized and the mouse ScFv antibodies would be fused with phage coat protein III and displayed on the surface of phage virions.

E. coli Top10F' host strain: From Invitrogen (Carlsbad, Calif.). Top10F' is a non-suppressor strain, in which the amber stop codon would be recognized and the soluble scFv antibodies would be produced.

VCSM13 helper phage: from Stratagene (La Jolla, Calif.).

LB Medium: Per liter: 10 g Bacto-Tryptone, 5 g yeast extract, 5 g NaCl.

LB-A Plates: Add 15 g agar to 1 L LB medium, autoclave, when cool, add ampicillin (AMP) to 100 μg/mL.

SB Medium: Per liter: 10 g MOPS, 30 g tryptone, 20 g yeast extract. Stir to dissolve, titrate to pH 7.0. Autoclave at 121° C., 20 minutes.

Top agar: Add 0.35 g of bacto agar to 50 mL of LB medium. Autoclave.

PBS: Per liter: 8 g NaCl, 0.2 g KCl, 1.7 g $Na_2HPO_4$, 0.163 g $KH_2PO_4$, pH to 7.4 with HCl.

Coating Buffer: 0.1M $NaHCO_3$ (pH 8.6)

TBS Buffer: 50 mM Tris-HCl, pH 7.5, 150 mM NaCl.

Substrate: TMB and $H_2O_2$ from Pierce (Rockford, Ill.)

Blocking buffer1: TBS (pH 7.4), 1 mg/mLBSA, 0.02% $NaN_3$. Filter sterilized and stored at 4° C.

Blocking buffer2: PBS (pH 7.4), 5 mg/mL Non-fat Milk powder, 0.02% $NaN_3$, store at 4° C.

HOURP-conjugated anti-M13 antibody: From GE healthcare (Fairfield, Conn.)

HOURP-conjugated anti-HA tag antibody: From GenScript Co. (Piscataway, N.J.)

HOURP conjugated goat anti-mouse secondary antibody: From Golden Bridge Int., Inc. (Mukilteo, Wash.).

Acidic eluting buffer: 0.1M Glycine-HCl (pH 2.2).

Phage precipitant (PEG/NaCl): 20% (w/v) polyethylene glycol-6000, 2.5 M NaCl. Autoclave, store at room temperature.

Total RNA extraction kit: QIAGEN Co. (Valencia, Calif.).

Plasmid purification kit: QIAGEN Co. (Valencia, Calif.).

Vector: pCDisplay-4 vector.

Agarose gel DNA fragment recovery kit: Takara Co. (Shiga, Japan).

Nitrocellulose membrane: Bio-Rad Laboratories, Inc. (Hercules, Calif.).

TABLE 3

Mouse VK 5' primers.

| Primer name | Primer sequence (5' → 3') | SEQ ID NO |
|---|---|---|
| MSCVK-1 | GGG CCC AGG CGG CCG AGC TCG AYA TCC AGC TGA CTC AGC C | 3 |
| MSCVK-2 | GGG CCC AGG CGG CCG AGC TCG AYA TTG TTC TCW CCC AGT C | 4 |
| MSCVK-3 | GGG CCC AGG CGG CCG AGC TCG AYA TTG TGM TMA CTC AGT C | 5 |
| MSCVK-4 | GGG CCC AGG CGG CCG AGC TCG AYA TTG TGY TRA CAC AGT C | 6 |
| MSCVK-5 | GGG CCC AGG CGG CCG AGC TCG AYA TTG TRA TGA CMC AGT C | 7 |

TABLE 3-continued

Mouse VK 5' primers.

| Primer name | Primer sequence (5' → 3') | SEQ ID NO |
|---|---|---|
| MSCVK-6  | GGG CCC AGG CGG CCG AGC TCG AYA TTM AGA TRA MCC AGT C | 8 |
| MSCVK-7  | GGG CCC AGG CGG CCG AGC TCG AYA TTC AGA TGA YDC AGT C | 9 |
| MSCVK-8  | GGG CCC AGG CGG CCG AGC TCG AYA TYC AGA TGA CAC AGA C | 10 |
| MSCVK-9  | GGG CCC AGG CGG CCG AGC TCG AYA TTG TTC TCA WCC AGT C | 11 |
| MSCVK-10 | GGG CCC AGG CGG CCG AGC TCG AYA TTG WGC TSA CCC AAT C | 12 |
| MSCVK-11 | GGG CCC AGG CGG CCG AGC TCG AYA TTS TRA TGA CCC ART C | 13 |
| MSCVK-12 | GGG CCC AGG CGG CCG AGC TCG AYR TTK TGA TGA CCC ARA C | 14 |
| MSCVK-13 | GGG CCC AGG CGG CCG AGC TCG AYA TTG TGA TGA CBC AGK C | 15 |
| MSCVK-14 | GGG CCC AGG CGG CCG AGC TCG AYA TTG TGA TAA CYC AGG A | 16 |
| MSCVK-15 | GGG CCC AGG CGG CCG AGC TCG AYA TTG TGA TGA CCC AGW T | 17 |
| MSCVK-16 | GGG CCC AGG CGG CCG AGC TCG AYA TTG TGA TGA CAC AAC C | 18 |
| MSCVK-17 | GGG CCC AGG CGG CCG AGC TCG AYA TTT TGC TGA CTC AGT C | 19 |

TABLE 4

VK 3' antisense primers

| Primer name | Primer sequence (5' → 3') | SEQ ID NO |
|---|---|---|
| MSCJK12-BL | GGA AGA TCT AGA GGA ACC ACC CCC ACC ACC GCC CGA GCC ACC GCC ACC AGA GGA TTT KAT TTC CAG YTT GGT CCC | 20 |
| MSCJK4-BL  | GGA AGA TCT AGA GGA ACC ACC CCC ACC ACC GCC CGA GCC ACC GCC ACC AGA GGA TTT TAT TTC CAA CTT TGT CCC | 21 |
| MSCJK5-BL  | GGA AGA TCT AGA GGA ACC ACC CCC ACC ACC GCC CGA GCC ACC GCC ACC AGA GGA TTT CAG CTC CAG CTT GGT CCC | 22 |

TABLE 5

VH 5' sense primers

| Primer name | Primer sequence (5' → 3') | SEQ ID NO |
|---|---|---|
| MSCVH-1  | GGT GGT TCC TCT AGA TCT TCC CTC GAG GTR MAG CTT CAG GAG TC | 23 |
| MSCVH-2  | GGT GGT TCC TCT AGA TCT TCC CTC GAG GTB CAG CTB CAG CAG TC | 24 |
| MSCVH-3  | GGT GGT TCC TCT AGA TCT TCC CTC GAG GTG CAG CTG AAG SAS TC | 25 |
| MSCVH-4  | GGT GGT TCC TCT AGA TCT TCC CTC GAG GTC CAR CTG CAA CAR TC | 26 |
| MSCVH-5  | GGT GGT TCC TCT AGA TCT TCC CTC GAG GTY CAG CTB CAG CAR TC | 27 |
| MSCVH-6  | GGT GGT TCC TCT AGA TCT TCC CTC GAG GTY CAR CTG CAG CAG TC | 28 |
| MSCVH-7  | GGT GGT TCC TCT AGA TCT TCC CTC GAG GTC CAC GTG AAG CAG TC | 29 |
| MSCVH-8  | GGT GGT TCC TCT AGA TCT TCC CTC GAG GTG AAS STG GTG GAA TC | 30 |
| MSCVH-9  | GGT GGT TCC TCT AGA TCT TCC CTC GAG GTG AWG YTG GTG GAG TC | 31 |
| MSCVH-10 | GGT GGT TCC TCT AGA TCT TCC CTC GAG GTG CAG SKG GTG GAG TC | 32 |
| MSCVH-11 | GGT GGT TCC TCT AGA TCT TCC CTC GAG GTG CAM CTG GTG GAG TC | 33 |

TABLE 5-continued

VH 5' sense primers

| Primer name | Primer sequence (5' → 3') | SEQ ID NO |
|---|---|---|
| MSCVH-12 | GGT GGT TCC TCT AGA TCT TCC CTC GAG GTG AAG CTG ATG GAR TC | 34 |
| MSCVH-13 | GGT GGT TCC TCT AGA TCT TCC CTC GAG GTG CAR CTT GTT GAG TC | 35 |
| MSCVH-14 | GGT GGT TCC TCT AGA TCT TCC CTC GAG GTR AAG CTT CTC GAG TC | 36 |
| MSCVH-15 | GGT GGT TCC TCT AGA TCT TCC CTC GAG GTG AAR STT GAG GAG TC | 37 |
| MSCVH-16 | GGT GGT TCC TCT AGA TCT TCC CTC GAG GTT ACT CTR AAA GWG TST G | 38 |
| MSCVH-17 | GGT GGT TCC TCT AGA TCT TCC CTC GAG GTC CAA CTV CAG CAR CC | 39 |
| MSCVH-18 | GGT GGT TCC TCT AGA TCT TCC CTC GAG GTG AAC TTG GAA GTG TC | 40 |
| MSCVH-19 | GGT GGT TCC TCT AGA TCT TCC CTC GAG GTG AAG GTC ATC GAG TC | 41 |

TABLE 6

VH 3' antisense primers

| Primer name | Primer sequence (5' → 3') | SEQ ID NO |
|---|---|---|
| MSCG1ab-B | CCT GGC CGG CCT GGC CAC TAG TGA CAG ATG GGG STG TYG TTT TGG C | 42 |

TABLE 7

Overlap extension primers

| Primer name | Primer sequence (5' → 3') | SEQ ID NO |
|---|---|---|
| RSC-F | GAG GAG GAG GAG GAG GAG GCG GGG CCC AGG CGG CCG AGC TC | 43 |
| RSC-B | GAG GAG GAG GAG GAG GAG CCT GGC CGG CCT GGC CAC TAG TG | 44 |

Experimental Procedures
Validation of Antigen-Antibody Reaction

The hybridoma cells were cultured in DMEM with 10% FBS. When the cells were confluent, they were grown for additional 2-3 days. The supernatant was harvested for ELISA. The recombinant C-prominin-1 protein was coated at a 1:1000 dilution in 96-well plate and incubated at 4° C. overnight. The coating buffer was discarded, the protein was washed 1 time, 300 μl/well of 5% milk buffer was added, and incubated at 4° C. overnight.

ELISA.

The hybridoma supernatant was diluted with 5% milk buffer at 1:1, 1:10, 1:100, 1:500 and 50 μL/well was added and incubated at 37° C. for one hour. The wells were washed four times, and 50 μL/well goat anti-mouse secondary antibody-HOURP conjugate was added at a dilution of 1:2000 and incubated at 37° C. for one hour. Washed four times, and added 50 μL/well substrate.

Preparation of XLI-BLUE Electrocompetent Cells and VCSM13 Helper Phage
Preparation of Electrocompetent E. coli-XLI-Blue.

15 mL of pre-warmed SB was inoculated in a 50-mL flask with a single E. coli colony from a glycerol stock that was freshly streaked onto an agar plate. Tetracycline was added to 30 μg/mL and cell were grown overnight at 250 rpm and 37° C. 2.5 mL of the culture was diluted into each of six two-liter flasks with 500 mL of SB, 10 mL of 20% glucose, and 5 mL of 1 M $MgCl_2$. No antibiotics were added. Flasks were shaken at 250 rpm and 37° C. until the optical density (OD) at 600 nm was about 0.7 after 2.5 hour. The six flask cultures and twelve 500-mL centrifuge bottles were chilled on ice for 15 minutes. Everything was kept on ice and done as rapidly as possible.

The flask cultures were poured into six pre-chilled 500-mL centrifuge bottles and spun at 3,000 g for 20 minutes at 4° C. The supernatant was poured off and each of the pellets was resuspended in 25 mL of pre-chilled 10% glycerol using 25-mL pre-chilled plastic pipettes. Two resuspended pellets were combined in one pre-chilled 500-mL centrifuge bottle and pre-chilled 10% glycerol was added up to about 500 mL. The other pellets were combined similarly and spun as before. Each pellet was resuspended in 500 mL of 10% pre-chilled glycerol and spun as before. The supernatant was poured off and each pellet was resuspended in 25 mL of pre-chilled 10% glycerol until complete homogeneity is reached. The suspensions were transferred into pre-chilled 50-mL tubes and spun at 2,500 g for 15 minutes at 4° C. Meanwhile, about 50 1.5 mL microcentrifuge tubes were set up in a rack in a dry ice/ethanol bath.

The supernatant from each tube was carefully poured off until the pellet began to slide out. The supernatant was discarded. Using a 25-mL pre-chilled plastic pipette, each pellet was resuspended in the remaining volume and the three suspensions were combined. A 1-mL pipette tip with a snipped-off end was used to immediately aliquot 300-4 volumes into the microcentrifuge tubes that were placed in the dry ice/ethanol bath. The tubes were capped and stored at −80° C.

Preparation of Helper Phage-VCSM13.

200 µg/mL of XLI-Blue at OD600 0.4 was infected with 10 µL of 100-fold serial dilutions of VCSM13 helper phage in a 37° C. water bath for 30 minutes. 3 mL molten H-top agar (42° C.) was added and poured onto warm LB plates. Plates were allowed to set and were incubated overnight at 37° C. A small plaque was picked into 5 mL of fresh SB at an OD600 of 0.4 and grown for about two hours shaking at 37° C. The culture was added to 500 mL SB in a 2 liter flask and grown shaking at 37° C. for one hour. Kanamycin was added to a final concentration of 50 µg/mL and the flasks were grown overnight shaking at 37° C.

The overnight culture was spun at 10,800 g for 15 minutes. 100 mL PEG/NaCl (20% polyethylene glycol 6000, 2.5M NaCl) was added to 400 mL supernatant and left for one hour on ice. The culture was spun 10,800 g for 30 minutes and the PEG/NaCl was poured away. The pellet was resuspended in 8 mL PBS and spun at 11,600 g for 10 minutes to remove any remaining bacterial debris. The supernatants were transferred to fresh 50-mL bottle and stored at 4° C.

Construction of Mouse scFv Library

Primers for mouse scFv amplification were synthesized. Total RNA was extracted and reverse-transcribed into cDNA. Extraction and purification of anti-human prominin-1 hybridoma cell total RNA was done following the QIAGEN RNeasy Micro Handbook.

The following components were added to a nuclease-free microcentrifuge tube:

| | |
|---|---|
| Oligo(dT)$_{20}$ (500 µg/mL) | 1 µL |
| Total RNA | 10 µL |
| 1 µL dNTP mix (10 mM each) | 1 µL |
| | 12 µL |

The mixture was heated to 65° C. for five minutes and then quick chilled on ice. The contents of the tube were collected by brief spin. The following was then added to the tube:

| | |
|---|---|
| 5 × first strand buffer | 4 µL |
| 0.1M DTT | 2 µL |
| RNaseOUT (inhibitor) | 1 µL |
| Superscript II RT | 1 µL |
| | 20 µL |

The contents were mixed and incubated at 4° C. for 50 minutes. The reaction by was inactivated by heating at 70° C. for 15 minutes.

PCR was run to amplify mouse scFv encoding gene repertoire. Variable region of Light-chain (VL) and heavy-chain (VH) fragment-encoding DNA sequences were amplified independently, fused by overlap-extension PCR, and cloned directionally by using two asymmetric sites of the rare cutter SfiI. Primer sequences used are as shown in the Materials and Reagents section. scFv (VL-linker-VH) was transcribed as a single transcript under the control of one LacZ promoter. The amber stop codon between the antibody genes and bacteriophage gene III enables the production of soluble scFv fragments in a non-suppressor strain of E. coli.

PCR Reactions and Conditions

First Round PCR for Amplification of VL and VH:

| | |
|---|---|
| Takara Ex Taq (5 U/µL) | 0.25 µL |
| 10X PCR buffer (Mg$^{2+}$ free) | 5.0 µL |
| MgCl$_2$ (25 mM) | 4.0 µL |
| dNTPs (2.5 mM of each) | 4.0 µL |
| cDNA | 2.0 µL |
| Primer1 (5' of VH or VL, 10 µM) | 1.0 µL |
| Primer2 (3' of VH or VL, 10 µM) | 1.0 µL |
| Add H$_2$O to | 50.0 µL |

First round PCR conditions:
94° C. for 5 minutes
30 cycles of
94° C. for 30 seconds
56° C. for 30 seconds
72° C. for 1 minute
Followed by 72° C. for 10 minutes Isolation of First Round PCR Product.

The PCR product was run on a 1% agarose gel and the correct-sized bands were cut out (the size of VH and VL of mouse antibody is around 400 bp). The DNA was purified by resin binding kit (Takara Co., Shiga, Japan).

Second Round of PCR (Overlap Extension)

In the second round of PCR, the appropriate first-round products were mixed in equal molar ratios to generate scFv product.

| | |
|---|---|
| Takara Ex Taq (5 U/µL) | 0.25 µL |
| 10X PCR buffer (Mg$^{2+}$ free) | 5.0 µL |
| MgCl$_2$ (25 mM) | 4.0 µL |
| dNTPs (2.5 mM of each) | 4.0 µL |
| Fd (50 ng) | 2.0 µL |
| Light chain (50 ng) | 2.0 µL |
| RSC-F (10 µM) | 1.0 µL |
| RSC-B (10 µM) | 1.0 µL |
| Add H$_2$O to | 50.0 µL |

Perform the PCR for scFv under the following conditions:
94° C. for 5 minutes
20 cycles of
94° C. for 30 seconds
56° C. for 30 seconds
72° C. for 2 minutes
Followed by 72° C. for 10 minutes Isolation of Second Round PCR Product The PCR product was run on a 1% agarose gel and the correct-sized bands were cut out (the size of scFv of mouse antibody is about 800 bp). The DNA was purified by a resin binding kit.

Restriction Digestion of the scFv PCR Product and pCDisplay-4 Vector

The digestion reaction of the PCR products contains:
10 µg of purified scFv product
160 Units of SfiI (16 Units per µg of DNA)
20 µL of 10× buffer M
Add water to a volume of 200 µL The digestion reaction of the pCDisplay-4 vector should contain:
20 µg of pCDisplay-4 vector
120 Units of SfiI (6 Units per µg of DNA)
20 µl of 10× buffer M
Add water to a volume of 200 µL Both digests were incubated for five hours at 50° C. The digested scFv and vector were purified on a 1% agarose gel (the correct size of double-cut vector is about 3400 bp, whereas the linearized vector DNA is 5000 bp).

Ligation of the Digested scFv with the Digested Vector DNA

The following ligation mixture was incubated at 16° C. overnight:
  pCDisplay-4 vector 2 µg
  scFv 3 µg
  5× buffer 40 µL
  T4 ligase 15 µL
  Add water to 200 µL Transformation of the Ligation Product into Competent *E. coli* XLI-BLUE Cells The ligation product was precipitated by adding 1 µL of glycogen, 1 µL of yeast tRNA, and 20 µL of 3 M sodium acetate, and 400 µL of ethanol, and storing the mixture overnight at −20° C.

The ligation product mixture was spun at full speed in a micro-centrifuge for 15 minutes at 4° C. The supernatant was removed and discarded. The pellet was rinsed twice with 1 mL of 70% ethanol and was drained inverted on a paper towel. The pellet was dissolved in 30 µL of water followed by gentle vortexing.

300 µL of electro-competent *E. coli* was thawed on ice. The competent cells were added to ligated library sample and were mixed by pipetting up and down once, and were transferred to a cuvette. The cuvette was stored on ice for one minute and then electroporated at 2.5 KV. The cuvette was flushed immediately with 1 mL and then twice with 2 mL of pre-warmed SB. The 5 µL of SB used to flush the cuvette were combined in a 50-mL flask. The flask was shaken at 250 rpm for one hour at 37° C.

10 mL of pre-warmed SB was added to the flask, and 3 µL of 100 mg/mL amp$^R$. The 15-mL culture was shaken at 250 rpm for 1 hour at 37° C. To titer the transformed bacteria, 2 µL of the culture was diluted in 200 µL of SB medium, and 100 µL and 10 µL of this 1:100 dilution were plated on LB+amp$^R$ plates. The plates were incubated overnight at 37° C.

80 mL of pre-warmed SB, 5 mL of 20% glucose, and 97 µL of amp$^R$ were added to the culture. The 100-mL culture was shaken at 250 rpm overnight at 37° C.

The bacterial cells were harvested by centrifugation of overnight culture, and the phagemid was purified by using a QIAGEN kit. The phagemid was stored at −20° C.

Library Panning Against Human Prominin-1

Library Reamplication

10 µg of mouse ScFv library phagemid was electro-transformed into 300 µL electro-competent XLI-BLUE cells. The cuvette was flushed immediately with 1 mL and then twice with 2 mL of pre-warmed SB, and the 5 mL were combined in a 50-mL flask. The flask was shaken at 250 rpm for one hour at 37° C.

10 mL of pre-warmed SB, 3 µLt of amp$^R$, and 30 µL of tet$^R$ was added. The 15-mL culture was shaken at 250 rpm for 1 hour at 37° C. 4.54 of amp$^R$ was added, and the flask was shaken for an additional hour at 250 rpm and 37° C.

4 mL of VCSM13 helper phage was added and the culture was transferred to a 500-mL flask. 180 mL of pre-warmed SB medium, 92.5 µl of amp$^R$ and 370 µL of tet$^R$ was added. The 200-mL culture was shaken at 300 rpm for 1.5 hours at 37° C.

200 µL of 50 mg/mL Kan$^R$ was added and shaking was continued 4-5 hours at 250 rpm at 37° C. The culture was spun at 3,000 g for 15 minutes at 4° C. 50 mL 5*PEG/NaCl was added and the culture was stored on ice for 30 minutes.

It was spun at 15,000 g for 15 minutes at 4° C. The supernatant was discarded. The bottle was drained by inverting on a paper towel, and the remaining liquid was wiped off from the upper part of the centrifuge bottle with a paper towel.

The phage pellet was resuspended in 2 mL of 1% BSA in TBS by pipetting up and down along the side of the centrifuge bottle. The suspension was transferred to a 1.5 mL tube which was vortexed and spun at full speed in a microcentrifuge for five minutes at 4° C. The supernatant was stored at 4° C.

Library Panning Against Human Prominin-1

The wells of a 96-well ELISA plate were coated with 2 µg of human prominin-1 in 50 µL of 0.1M NaHCO$_3$, pH8.6, and incubated overnight at 4° C. The coating solution was shaken out of the wells and the wells were blocked by adding 300 µL of 1% BSA (w/v) in TBS. The plate was sealed and incubated overnight at 4° C.

The blocking buffer was shaken out of the wells and 50 µL of freshly prepared phage library was added to each well (4 wells). The plate was sealed and incubated for two hours at 37° C.

The phage solution was shaken out of the wells and the wells were washed five times by an ELISA plate washer machine (washed 10 times in the second round, and washed 15 times in the third round).

After shaking out the final washing solution, 50 µL of 0.1M glycine-HCl, pH 2.2, was added and the plate was incubates for 10 minutes at 37° C. The solution was pipetted 10 times vigorously up and down and the eluate was transferred to a microfuge tube containing 6 µL of neutralizing solution (1M Tris). The eluates were transferred to the 2-mL XLI-BLUE cells and incubated at 37° C. for 30 minutes.

6 mL of prewarmed SB medium and 1.6 µL of 100 mg/mL amp$^R$ and 12 µl of 5 mg/mL tet$^R$ were added to the cells. The 8-mL culture was shaken at 250 rpm for one hour at 37° C. 2.4 µL of amp$^R$ was added and the culture was shaken for an additional hour at 250 rpm and 37° C.

2 mL of VCSM13 helper phage was added to the 8-mL culture and the culture was transferred to a flask. 90 mL of SB medium and 46 µL amp$^R$ and 184 µL of tet$^R$ were added. The 100-mL culture was shaken at 250 rpm for 1.5 hours at 37° C.

100 µL of 50 mg/mL kan$^R$ was added and shaking was continued overnight at 250 rpm at 37° C.

The culture was spun at 3,000 g for 15 minutes at 4° C. 25 mL 5*PEG/NaCl was added, and the culture was stored on ice for 30 minutes.

The culture was spun at 15,000 g for 15 minutes at 4° C. The supernatant was discarded. The bottle was drained by inverting on a paper towel, and the remaining liquid was wiped off from the upper part of the centrifuge bottle with a paper towel.

The phage pellet was resuspended in 2 mL of 1% BSA in TBS by pipetting up and down along the side of the centrifuge bottle. The suspension was transferred to a 1.5 mL tube and was vortex and spun at full speed in a microcentrifuge for five minutes at 4° C. The supernatant was kept at 4° C. for next round panning.

Three rounds of panning have been done.

Phage ELISA 30 single colonies were randomly picked up from library panning the third elute titration plate, and inoculated in 2 mL LB medium with 100 µg/mL amp$^R$. The 2-mL tubes were shaken at 250 rpm for 5-8 hours at 37° C.

40 μL, helper phage was added VCSM13 to each culture, and shaken for another two hours at 37° C.

2 μL of kan$^R$ was added to each culture, and the cultures were shaken overnight at 250 rpm and 30° C.

The cultures were centrifuged at 12,000 rpm for 15 minutes, and the supernatant was taken. The supernatant containing phage was diluted with equal volume of 5% milk and was incubated for 10 minutes at room temperature.

100 μL of the dilute phage was added to each well, and incubated for two hours at 37° C.

The plate was washed five times.

50 μL per well of diluted secondary antibody conjugate at 1:3,000 (HOURP-conjugated anti-M13 antibodies, diluted in 5% milk) was added, and incubated for one hour at 37° C.

The plate was washed five times. 50 TMB substrate was added for detection, and incubated for 30 minutes at RT.

DNA Sequencing and Bioinformatics Analysis

Nine clones were found to react specifically with the human prominin-1 by phage ELISA, they are No. 4, 5, 6, 7, 8, 10, 11, 22, 23. The plasmids were extracted, and the primers for sequencing are: P1: 5'-AAGACAGCTATCGC-GATTGCAG-3' (SEQ ID NO:45), and P2: 5'-GCCCCCTT-ATTAGCGTTTGCCATC-3' (SEQ ID NO:46).

The returned sequences were translated with professional software (DNA Star) and the protein sequences were aligned.

scFv Prokaryotic Expression

According the sequencing results, No. 11 clone was transformed into *E. coli* host, Top10F' for expression. Single colonies were picked and grow overnight at 37° C. in LB media with 100 μg/mL Amp$^R$. IPTG was added to a final concentration of 1 mM, and induce at 30° C. overnight.

The overnight culture was collected and spun at 10,000 rpm for five minutes. The supernatant and pellet were collected for expression detection. The proteins were denatured with 2×SDS sample buffer by boiling at 100° C. for 10 minutes. The protein samples were separated by 10% SDS-PAGE and transferred onto nitrocellulose membrane (Bio-Rad Laboratories, Inc., Hercules, Calif.). The membrane was blocked with milk blocking buffer at RT for one hour, and was incubated with HOURP-conjugated anti-HA tag antibody at 1:200 dilution for 1.5 hour at RT, washed four times in wash buffer, the proteins were detected by a chemiluminescence assay as recommended by the manufacturer (Pierce, Rockford, Ill.).

Soluble scFv ELISA

A single colony was picked from No. 11 DNA transformed Top 10F' *E. coli* LB-Amp plate in and used to inoculate 25 mL LB medium with 100 μg/mL Amp. The culture was shaken at 37° C. at 250 rpm overnight.

The 25 mL overnight culture was diluted to 500 mL LB containing Amp and was shaken at 37° C. at 250 rpm for about two hours until the OD600 reached 0.5 to 0.7. IPTG was added to a final concentration of 1 mM. The culture was shaken at 30° C. overnight.

The culture was centrifuged at 5,000 g for 20 minutes at 4° C. The supernatant was kept for ELISA.

The cell pellet was completely suspended with 50 mL ice-cold PBS containing protease inhibitors (1 mM PMSF), and was sonicated on ice in short bursts. The power setting was 7 min, 40% power cycle 5 (HD2200 W/MS 73). Triton X-100 was added to the cell lysate to a final concentration of 1% and was mixed gently for 30 minutes at room temperature to aid in solubilization of the fusion protein.

The mixture was centrifuged at 15,000 rpm (Heraeus #3334 rotor) for 30 minutes at 4° C., and the supernatant was taken for ELISA.

The 2 supernatants were diluted (one is from overnight culture supernatant, and the other is from overnight culture pellet) containing soluble mouse scFv with equal volume of 5% milk and were incubated for 10 minutes at room temperature.

100 μL of the diluted scFv was added to each well (coated with human prominin-1), and incubated for one hour at 37° C.

The plate was washed five times.

50 μL per well of diluted secondary antibody conjugate at 1:2,000 (HOURP-conjugated anti-HA, diluted in 5% milk) was added, and incubated for one hour at 37° C.

The plate was washed five times.

50 μL/well TMB substrate was added for detection, and incubated for 30 minutes at room temperature.

Validation of Antigen-Antibody Reaction

Under the negative and blank control, the supernatant containing MAb can specifically react with human prominin-1, at 1:1, 1:10, 1:100, 1:500 dilution, demonstrating that the anti-human C-prominin-1 murine monoclonal antibody (No. 7) binds its antigen with high specificity and affinity, and cloning and expression of its variable region are feasible.

Construction of Mini Mouse Antibody Library with scFv Format

The mini mouse scFv library was constructed in two steps. The variable region gene pools of VL and VH were amplified with their corresponding backward and forward primers, to maintain maximal diversity. Of the 19 combinations (19×1) for VH, and 51 combinations (17×3) for VL, only 4 VH and 7 VL combinations have amplified positive bands (about 400 bp). After purification, the VH and VL genes were combined with each other to develop scFv genes by an overlap extension (about 800 bp). The overlap scFv PCR product and pCDisplay-4 vector were digested using SfiI. After ligation, the ligation product was transformed into XLI-BLUE, and the resulting recombinant phagemid was stored at −20° C. By a single electroporation, a phage antibody library containing $1.0 \times 10^7$ members was constructed.

Biopanning Against Human Prominin-1

The mouse scFv library was panned against human prominin-1. As seen in Table 8, after three rounds of panning, enrichment of specific scFv clones was efficient, achieving a 394-fold $(6.3 \times 10^{-5}/1.6 \times 10^{-7})$ increase in relative yield, from the first to the third round of panning.

TABLE 8

Panning of mouse scFv library against human prominin-1.

| Rounds of screening | Titer of input phage | Titer of output phage | output/input |
|---|---|---|---|
| 1 | $1.3 \times 10^{12}$ | $2.1 \times 10^5$ | $1.6 \times 10^{-7}$ |
| 2 | $1.7 \times 10^{12}$ | $6.5 \times 10^6$ | $3.8 \times 10^{-6}$ |
| 3 | $3.0 \times 10^{12}$ | $1.9 \times 10^8$ | $6.3 \times 10^{-5}$ |

Phage ELISA

After three rounds of panning, 30 randomly picked phage clones were screened, and nine were found to react specifically with human prominin-1 protein by phage ELISA (Table 9). The values of A450 with bond character were considered positive clones to prominin-1.

TABLE 9

The result of phage-ELISA of the third round elute.

| No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| A450 | 0.3 | 0.1 | 0.1 | 1.0 | 1.3 | 1.3 | 0.9 | 1.0 | 0.3 | 1.2 | 1.4 | 0.2 | 0.3 | 0.2 | 0.2 |

| No. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| A450 | 0.4 | 0.1 | 0.1 | 0.3 | 0.3 | 0.2 | 1.2 | 1.1 | 0.1 | 0.3 | 0.3 | 0.2 | 0.3 | 0.1 | 0.4 |

The Sequencing Results

The nine positive clones were sequenced successfully and their deduced amino acid sequences are listed below (Table 10). Analyzing their sequences with DNA Star software revealed that the heavy- and light-chain variable regions of No. 5, 8, 11, 22, 23 are identical. Also all the sequences are very close to each other, suggesting that they are all derived from the single hybridoma clone, hybridoma cell line that secretes anti-prominin-1 MAb. The variation could be due to PCR or sequencing.

TABLE 10

Deduced amino acid sequences of variable regions of heavy and light chains of the nine positive scFv clones against human prominin-1 selected by phage ELISA.

| Clone | Amino Acid Sequence | SEQ ID NO |
|---|---|---|
| No. 4 | AQAAELDIVLTQSPAIMSASPGEKVTISCSASSSVGYMYWYQQKPGSSPKPWIYRPSN LASGVPARFSGSGSGTSYSLTISSMEAEDAATYYCQQYHSYPPTFGAGTKLELKSSGG GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQ | 47 |
| No. 5 | AQAAELDIVLTQSPAIMSASPGEKVTISCSASSSVSYMYWYQQKPGSSPKPWIYRTSN LASGVPARFSGSGSGTSYSLTISSMEAEDAATYYCQQYHSYPPTFGAGTKLELKSSGG GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQAGQ | 48 |
| No. 6 | AQAAELDIVLTQSPAIMSASPGEKVTISCSASSSVSYMYWYQQKPGSSPKPWIYRPSN LASGVPARFSGSGSGTSYSLTISSMEAEDAATYYCQQYHSYPPTFGAGTKLELKSSGG GGSGGGGGGSSRSSPEVMLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQAGQ | 49 |
| No. 7 | AQAAELDIVLTQSPAIMSASPGEKVTISCSASSSVSYMYWYQQKPGQPPRLLIYLVSN LESGVPARFSGSGSGTDFTLNIHPVEEEDAATYYCQQYHSYPPTFGAGTKLEIKSSGG GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQAGQ | 50 |
| No. 8 | AQAAELDIVLTQSPAIMSASPGEKVTISCSASSSVSYMYWYQQKPGSSPKPWIYRPSN LASGVPARFSGSGSGTSYSLTISSMEAEDAATYYCQQYHSYPPTFGAGTKLELKSSGG GGSGGGGGGSSRSSLEVHLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQAGQ | 51 |
| No. 10 | AQAAELDIVLSQSPAIMSASPGEKVTISCSASSSVSYMYWYQQKPGSPPKPWIYRTSN LASGVPARFSGSGSGTSYSLTISSMEAEDAATYYCQQYHSYPPTFGAGTKLELKSSGG GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDCG DYFDYWGQGTTLTVSSAKTTPPSVTSGQAGQ | 52 |
| No. 11 | AQAAELDIVLSQSPAIMSASPGEKVTISCSASSSVSYMYWYQQKPGSSPKPWIYRTSN LASGVPARFSGSGSGTSYSLTISSMEAEDAATYYCQQYHSYPPTFGAGTKLELKSSGG GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTPPSVTSGQAGQ | 53 |
| No. 22 | AQAAELDIVLTQSPAIMSASPGEKVTISCSASSSVSYMYWYQQKPGSSPKPWIYRPSN LASGVPARFSGSGSGTSYSLTISSMEAEDAATYYCQQYHSYPPTFGAGTKLELKSSGD GGSGGGGGGSSRSSLEVKLVESGPELKKPGETVKISCKASGYTFTDYSMHWVNQAPGK GLKWMGWINTETGEPSYADDFKGRFAFSLETSASTAYLQINNLKNEDTATYFCATDYG DYFDYWGQGTTLTVSSAKTTAPSVTSGQAGQ | 54 |

TABLE 10-continued

Deduced amino acid sequences of variable regions of heavy and light chains of the nine positive scFv clones against human prominin-1 selected by phage ELISA.

| Clone | Amino Acid Sequence | SEQ ID NO |
|---|---|---|
| No. 23 | AQAAELDIVLTQSPAIMSASPGEKVTISCSASSSVSYMYWYQQKPGSSPKPWIYRPSN<br>LASGVPARFSGSGSGTSYSLTISSMEAEDAATYYCQQYHSYPPTFGAGTKLELKSSGG<br>GGSGGGGGSSRSS*LEVQLVESGPELKKPGETVKISCKASGYTFTDYSMHWVNQAPGK<br>GLKWMGWINTETGEPSYADDFKGRFAFSLETSASTAYLQINNLKNEDTATYFCATDYG<br>DYFDYWGQGTTLTVSSAKTTAPSVTSGQAGQ* | 55 |

Underline text = light chain (VL);
*italicized text* - heavy chain (VH);
plain text = linker No. 11 was transformed into *E. coli* Top 10F' for expression. Its DNA sequence is listed below.

TABLE 11 scFv No. 11 DNA sequence

| Nucleic Acid Sequence | SEQ ID NO |
|---|---|
| GGCCCAGGCGGCCGAGCTCGACATTGTTCTCTCCCAGTCTCCAGCAATCATGTCTGCATCTCC<br>AGGGGAGAAGGTCACCATATCCTGCAGTGCCAGCTCAAGTGTAAGTTATATGTACTGGTACCA<br>GCAGAACCAGGATCCTCCCCCAAACCCTGGATTTATCGCACATCCAACCTGGCTTCTGGAGTC<br>CCTGCTCGCTTCAGTGGCAGTGGGTCTGGGACCTCTTACTCTCTCACAATCAGCAGCATGGAG<br>GCTGAAGATGCTGCCACTTATTACTGCCAGCAGTATCATAGTTACCCACCCACGTTCGGTGCT<br>GGGACCAAGCTGGAGCTGAAA*TCCTCTGGTGGCGGTGGCTCGGGCGGTGGTGGGGGTGGTTCC<br>TCTAGATCTTCCCTCGAGGTGAAGCTGGTGGAGTCTGGACCTGAGCTGAAGAAGCCTGGAGAG*<br>ACAGTCAAGATCTCCTGCAAGGCTTCTGGTTATACCTTCACAGACTATTCAATGCACTGGGTG<br>AATCAGGCTCCAGGAAAGGGTTTAAAGTGGATGGGCTGGATAAACACTGAGACTGGTGAGCCA<br>TCATATGCAGATGACTTCAAGGGACGGTTTGCCTTCTCTTTGGAAACCTCTGCCAGCACTGCC<br>TATTTGCAGATCAACAACCTCAAAAATGAGGACACGGCTACATATTTCTGTGCTACCGATTAC<br>GGGGACTACTTTGACTACTGGGGCCAAGGCACCACTCTCACAGTCTCCTCAGCCAAAACGACA<br>CCCCCATCTGTCACTAGTGGCCAGGCCGGCCAGCACCATCACCATCACCATGGCGCATACCCG<br>TACGACGTTCCGGACTACGCTTCTTAG | 56 |

Underlined text = SfiI site;
*italicized text* = linker;
bold text = 6HIS tag;
highlighted text = HA tag; and
strikethrough text = Amber stop codon.

Detection of scFv Expressed in a Soluble Form

By transforming into *E. coli* Top10F', soluble recombinant No. 11 scFv antibody was produced. Since Top10F' is a non-suppressor strain, the amber stop codon was translated and the soluble scFv antibody was produced. Soluble expression of scFv was achieved by utilizing *E. coli* secretion machinery and induced at low temperature (30° C.).

The expressed scFv was found mainly in the culture medium and periplasmic space of *E. coli*. Western-blot detection of expressed soluble scFv in the culture supernatant and pellet. The detection antibody was HOURP-conjugated anti-HA tag antibody, since the scFv was expressed as a HA-fusion protein with a size of 34 kDa.

Soluble scFv Based ELISA

Soluble scFv ELISA was performed to confirm the binding specificity to the target protein. Here, the expressed scFv was captured by human prominin-1 pre-coated plate, and the binding of the soluble scFv fused with HA tag was detected with anti-HA Ab-HOURP conjugate. As shown in Table 12, No. 11 scFv, expressed both in culture medium and periplasmic space, was confirmed specific for human prominin-1 protein, although the binding signal is lower than positive control, the parent intact bivalent antibody. Supernatant and pellet are test samples, PC means positive control, hybridoma secreted antibody (diluted at 1:2000) was used, BLK means blank.

TABLE 12

Soluble ELISA against human prominin-1.

| No. | Supernatant | Pellet | Positive Control | Blank |
|---|---|---|---|---|
| A450 | 0.9 | 1.4 | 1.9 | 0.2 |

By using phage display technology, we have successfully cloned and selected VL and VH genes of murine MAb against human prominin-1, and expressed its scFv fragment in *E. coli* host.

After three rounds of panning against human prominin-1 by newly constructed mouse scFv library which derived from human prominin-1 specific MAb [clone 7], nine clones were detected with positive phage ELISA signals, namely, No. 4, 5, 6, 7, 8, 10, 11, 22, 23. DNA sequencing revealed that heavy- and light-chain variable regions of all of them are similar. In particular, No. 5, 8, 11, 22 and 23 are identical, suggesting that they are all derived from a single hybridoma cell line that secretes anti-prominin-1 MAb.

No. 11 clone was used to express soluble scFv protein in Top10F' *E. coli* host. After overnight inducing at 30° C., the expressed scFv was found mainly in the culture medium and periplasmic space of *E. coli*.

In the end, soluble scFv-based ELISA confirmed the specific binding of No. 11 scFv antibody against the target protein, demonstrating this scFv gene derive from its corresponding body, human prominin-1-specific MAb.

The DNA sequence of this No. 11 clone is the real cDNA sequence of the VH and VL fragments of the original hybridoma. The minor alteration in sequences of other scFv clones could derive from PCR and DNA sequencing.

Conventionally, MAbs are generated by fusing B cells from an immunized mouse with myeloma cell from the same species. Within this immortal hybridoma cell line, B cell secretes MAb against its epitope, the myeloma cell line makes them immortal, which means that they can grow and divide indefinitely. When the MAb-encoded scFv gene is to be cloned from hybridoma total RNA, conceivably, we refer to the antigen specific rearranged immunoglobulin heavy- and light-chain gene, but myeloma is B cell origin, and has all the cellular machinery necessary for the secretion of antibodies, and many even transcribe the genes and secrete these proteins. So, there is a possibility that hybridoma's two partner cells encoded antibody VH and VL genes may mismatch each other, and result in the failure of scFv cloning.

Based on several different analysis, it is estimated that there are more than 100 mice heavy-chain germ-line sequences organized into five or more families, and a similar number of k light-chain germ-line sequences. So, it is hard to amplify the antigen specific antibody VH and VL gene with one pair of primers. Though the degenerated primers may be used, this approach inevitably modifies the 5' and 3' ends of the rearranged genes segments, leading to low protein expression, or even to non-expression of recombinant scFv.

To circumvent these problems described above, phage display technique has been employed to clone human prominin-1 specific MAb scFv construct and to get prokaryotic expression. Two sets of mouse specific VH and VL primers were designed, and PCR used with all primer combinations theoretically permits the amplification of all rearranged variable regions. The amplified VH, VL pools were then linked through an overlap PCR to give the final scFv genes that are used for cloning. Thus, VH, VL genes repertoire with authentic residues at both ends were amplified, and the ScFv genes pool gave maximal combination between VH and VL, which surely contained prominin-1-specific MAb's scFv clone.

After three rounds of panning against prominin-1, nine clones were detected with positive phage ELISA signals. DNA sequencing revealed that five of them were identical, suggesting that they were all derived from a single hybridoma cell line that secretes anti-prominin-1 MAb and this cloning strategy worked well.

The length of the linker appears to influence the association state of the scFv molecule. Long linkers (about 20 amino acids) appear to favor monomeric molecules, whereas short linkers (e.g., five amino acids) favor dimers, in which the VH of the one scFv molecule is paired with the VL of the other and vice versa. In this study, a 18-amino-acid long linker (SSGGGSGGGGGGSSRSS; SEQ ID NO:74) is used to connect VH and VL fragment.

Example 11

Ult-Luc or CMV-CD133 pDNA constructs were transfected into HEK293-TLR2 cells using JetPEI transfection reagent according to the manufacturer's instructions (Polyplus Transfection). Briefly, $7.5 \times 10^5$ cells/well were seeded in a 6-well plate. Twelve hours later, 2.5 μg of each pDNA were diluted in 5 μl 5% dextrose and mixed with 0.35 μL, JetPEI also in 5 μl 5% dextrose. Following incubation for 15 minutes, the transfection mix was added to the cells. Forty-eight hours later, cells were harvested using non-enzymatic cell dissociation buffer (Sigma-Aldrich Corp., St. Louis, Mo.) for flow cytometry.

Figure 4:
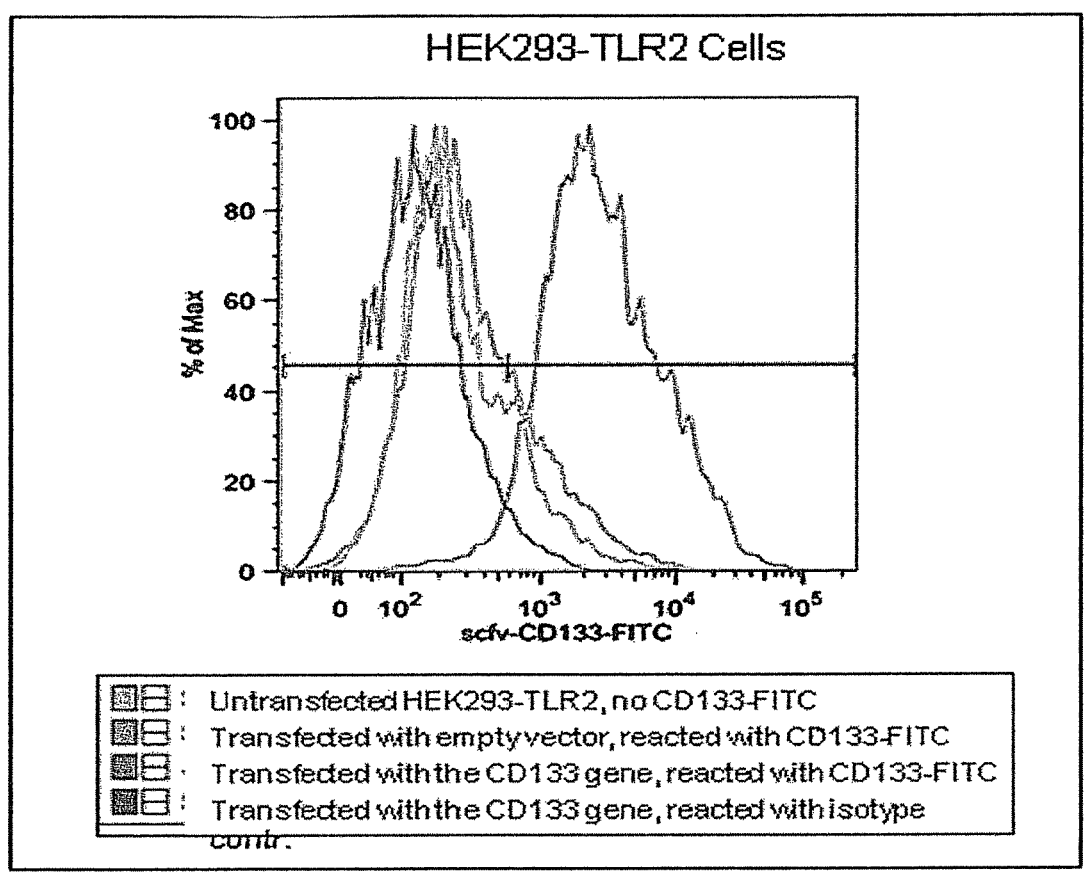
FIG. 4: CD133scFV recognizes the CD133 marker. The CD133scFv was labeled with FITC. An oligonucleotide was prepared from the known GenBank sequence of CD133 and then transfected into HEK293-TLR2 cells using a polyethylenimine (PEI)-DNA complex. The cells were incubated with anti-CD133scFv-FITC complex, washed, and then analyzed by flow cytometry. Data are represented in standard histogram format whereby % positive cells are plotted against fluorescence intensity. Only the CD133-transfected cells reacted with the FITC-labeled CD133scFv. Controls include transfected cells reacted with empty vector, transfected cells reacted with an isotype control, or untransfected cells that are not reacted with CD133-FITC.

CD133scFv was labeled with FITC at a FITC:scFv ratio of 24:1 (Invitrogen, Carlsbad, Calif.) and dialyzed to remove any free unbound FITC. An oligonucleotide was prepared from the known GeneBank sequence of CD133 and then transfected into HEK293-TLR2 cells using a polyethylenimine (PEI)-DNA complex. The cells were incubated with anti-CD133scFv-FITC complex, washed, and then studied on a BD FACScanto II flow cytometer. Data are represented in standard histogram format whereby % positive cells are plotted against fluorescence intensity. Only the CD133 transfected cells reacted with the FITC-labeled CD133scFv. Controls include transfected cells reacted with empty vector, transfected cells reacted with an isotype control, or untransfected cells that are not reacted with CD133-FITC. Results are shown in FIG. 4.

Example 12

Construction of dCD133KDEL

Synthesis and assembly of hybrid genes encoding the single-chain CD133KDEL was accomplished using DNA-shuffling and DNA cloning techniques. The fully assembled fusion gene (from 5' end to 3' end) consisted of an NcoI restriction site, an ATG initiation codon, the genes for 243 amino acid human dCD133, glycine serine (G4S)3 linker between heavy and light chain sFv, the 7 amino-acid EASGGPE linker, the first 362 amino acids of the pseudomonas exotoxin (PE) molecule with KDEL replacing the REDLK at the C-terminus, and a NotI restriction site at the 3' end of the construct. The resultant 1846 bp NcoI/NotI fragment gene was spliced into the pET28c bacteria expression vector under control of an isopropyl-b-D-thiogalactopyranoside inducible T7 promoter. DNA sequencing analysis (Biomedical Genomics Center, University of Minnesota) was used to verify that the gene was correct in sequence and had been cloned in frame. To create deimmunized CD133KDEL (dCD133KDEL) with decreased immunogenicity, eight amino acids representing the seven major epitopes on PE38 were mutated using the QuickChange Site-Directed Mutagenesis Kit (Stratagene, La Jolla, Calif.). The following amino acids were altered: R490A, R513A, R467A, E548S, K590S, R432G, Q332S, R313A and confirmed by DNA sequencing.

Example 13 dCD133KDEL Fusion Protein Kills Squamous Carcinoma Cells In Vitro

The head and neck cancer cell line UMSCC-11B was cultured in 24-well tissue culture plates. Briefly, 10,000 cells were plated per well. Media containing the fusion protein was replaced daily. Wells were harvested every other day using a trypsin/saline solution, stained with trypan blue vital dye, and counted microscopically with a hemoctyometer. Untreated wells were typically confluent by day 8. In wells containing 0.5 nM dCD133KDEL, cell growth was inhibited compared to the cells in the untreated wells. In wells containing a similar concentration of a control anti-B cell targeted toxin CD22KDEL, growth was not inhibited. Results are shown in FIG. 6.

Example 14

For tumor initiation studies, UMSCC-11B squamous carcinoma cells were injected into the right flank of nude mice at a concentration of 300,000 cells/mouse. Tumor size was measured twice each week using digital calipers and tumor volume was calculated. Three experimental cell groups were studied. Animals given UMSCC-11B cells enriched for CD133 expression (using Stem Cell Technologies FITC selection magnetic bead kit at a purity of greater than 80%) showed the highest incidence of growth (75%) and grew at the fastest rate, consistent with an enriched cancer stem cell population. The unsorted cells (controls) had a tumor incidence of 38% and grew significantly slower (p<0.04). A third group of mice were given cells cultured with dCD133KDEL for six days. These mice had the lowest level of tumor takes, only one out of four and this tumor grew at the slowest rate. The data indicates that dCD133KDEL inhibits tumor initiation. Results are shown in FIG. 7.

Example 15

MDA-MB-231 cells were cultured in 24-well tissue culture plates. Briefly, 10,000 cells were plated/well. Media containing the fusion protein was replaced daily. Wells were harvested every other day using a trypsin/saline solution, stained with trypan blue vital dye, and counted microscopically with a hemoctyometer. In wells containing 1 nM or 10 nM dCD133KDEL, cell growth was inhibited compared to the cells in the untreated wells. In wells containing a similar concentration of a control anti-T cell targeted toxin CD3CD3KDEL, growth was slowed, but not entirely inhibited. NTR—No treatment. Results are shown in FIG. 8.

Example 16

To determine the effect of deimmunized toxin linked to CD22CD19 targeting ligands on $CD22^+CD19^+$ Daudi cells, increasing concentrations of 2219KDEL7mut made with deimmunized toxin were compared to non-mutated 2219KDEL made with non-deimmunized toxin in a proliferation assay. Data are presented in FIG. 11 as % control response.

To detect anti-toxin antibodies, immunocompetent C57BL/6 mice were immunized with either deimmunized drug or non-deimmunized drug. Mice were immunized weekly for several weeks. Serums from individual mice were analyzed in a modified ELISA measuring μg/ml anti-toxin IgG. Data were represented as the average μg IgG/ml. The two groups significantly differed (p<0.05) and the deimmunized drug showed about an 80% reduction in anti-toxin after several immunizations. Results are shown in FIG. 12.

To determine whether neutralizing antibodies were present, serum from the immunized mice were tested for their ability to neutralize a constant inhibitory concentration of 2219KDEL. Data are depicted as percent control response. SAL=Serum anti-toxin levels. High serum anti-toxin levels with serum from mice immunized with non-deimmunized drugs neutralized, but not the sera from the mice immunized with deimmunized drug. Results are shown in FIG. 13.

To determine whether deimmunized 2219KDEL7mut was efficacious, SCID mice given a lethal injection of Raji-luc cells were treated with three courses of drug or control CD3CD3KDEL beginning on day 3. Pooled data (experiments 1 and 2) are shown as a Kaplan-Meier plot. The drug was highly active and able to prevent the onset of cancer. Results are shown in FIG. 14.

Example 17

Mouse Model

Our mouse models involve the following features. 1) The cells in the breast cancer and pancreatic models may be given systemically and the cancer metastasizes to several key organs including the liver. 2) We treat systemically intraperitoneally with drug. 3) We can follow the development of tumor in real time. We accomplished this by genetically engineering all of our carcinoma lines with firefly luciferase and green fluorescent protein (GFP) reporter genes so that we could follow the effect of drug treatment over time by bioluminescent imaging and visualize what is going on internally without killing the mice at each time point. All tumor lines were selected for stable transfectants and no change in tumorogenicity or antigen expression. Histological studies were performed to confirm the bioluminescent data. The gene used for the original transfection encodes dual reporters luciferase and GFP, which adds additional information. For example, in a recent study we used the luciferase reporter to monitor tumor progression and the GFP reporter to locate specific organs targeted by tumor in the same animals. The advantage is that we can visualize metastasis in vivo in real time and learn more about the nature of metastatic progression. For breast cancer and head and neck cancer, the cells are surgically implanted in the spleen. Pancreatic cancer cells are given orthotopically. The cells are lethal in our models and tumors most commonly metastasize to the liver. 4) Long-term survivors are verified as tumor-free by histology studies. Histology findings always correlate with our bioluminescent imaging results. The value of these models has been proven in several recent publications.

The Effect of dCD133KDEL on Tumor Progression in Mice with Systemic MDA-MB-231 Tumors Systemic tumors were induced in nude mice by injecting tumor cells via intrasplenic injection. For intrasplenic injection, a small incision was made and forceps used to immobilize the spleen. One half to two million cells were slowly injected into the spleen using a 27 gauge needle to avoid backflow. Intraperitoneal treatment of the mice was begun on Day-6 post-tumor inoculation with dCD133KDEL. A single course of treatment consisted of an injection of 20 μg of drug given every other day (MWF) and mice were given 6 courses of treatment. Animals were imaged weekly. Bioluminescence intensity was measured as a function of photons/sec/sr/cm². Controls were untreated. Mice were imaged in real time and images were captured using Xenogen Ivis imaging system (Xenogen Corporation, Hopkington, Mass.) and analyzed IGOR Pro 4.09a software (WaveMetrics, Inc., Portland, Oreg.). Prior to imaging, mice were anesthetized using isoflorane gas. All mice received 100 μl of a 30 mg/ml D-luciferin aqueous solution (Gold Biotechnology, St. Louis Mo.) as a substrate for luciferase 10 minutes before imaging. All images represent a five minute exposure time and all regions of interest (ROI) are expressed in units of photons/sec/sr/cm². Results are shown in FIG. 9.

Combination Treatment

Systemic MDA-MB-231 tumors were induced in nude mice by giving cells via intrasplenic injection. Treatment of mice was begun on Day-6 post-tumor inoculation with a suboptimal dose of dCD133KDEL, a suboptimal dose of dEGF4KDEL, or a mixture of both suboptimal doses. A single course of treatment consisted of an injection of 4 µg of dCD133KDEL or 3 µg EGF4KDEL given every other day (MWF) and mice were given 4 courses of treatment. The last group was treated with both drugs combined. Animals were imaged weekly. Bioluminescence intensity was measured as a function of photons/sec/sr/cm$^2$. Controls were untreated. Results are shown in FIG. 10.

Example 18 dCD133KDEL Inhibits the Human Pancreatic Adenocarcinoma MiaPaCa-2 In Vitro

Figure 16:
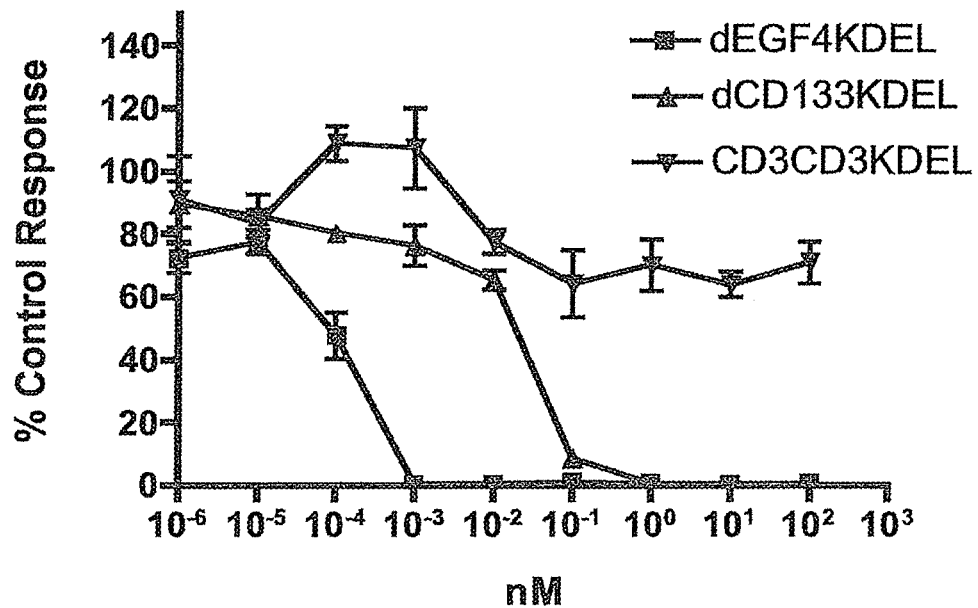
FIG. 16: The effect of dCD133KDEL on MiaPaCa-2 pancreatic cancer cells. dCD133KDEL was tested on the cell line using a $^3$H-leucine incorporation protein synthesis assay. CD3CD3KDEL was included as negative control. dEGF4KDEL was included as a positive control because of the high EGFR expression on this cell line. Data is expressed as percentage of $^3$H-leucine incorporation relative to control cells incubated in media alone.

Protein synthesis inhibition is used as a measure of anti-cancer activity. To measure protein synthesis, we used a standard assay measuring $^3$H-Leucine incorporation. Cells (10$^4$/well) were plated in 96-well flat-bottomed plates and incubated overnight at 37° C. at 5% CO$_2$. dCD133KDEL in varying concentrations were added to wells in triplicate. Incubation continued for 72 hours and [Methyl-$^3$H]-Leucine (GE Healthcare, UK) was added (1 µCi per well) for the final 24 hours of incubation. Plates were frozen to detach cells and then harvested onto a glass fiber filter, washed, dried, and counted using standard scintillation methods. Results are shown in FIG. 16.

Example 19

CD133 Expression on UMSCC-11B Cells

CD133 expression on UMSCC-11B cells on head and neck cancer cells. CD133 expression was measured on the UMSCC-11B cell line using flow cytometery. Cells were reacted with anti-CD133scFV-FITC for 30 minutes in the dark on ice. Cells were then washed 3x using saline and studied using a flow cytometer (FACScanto™ II, BD Biosciences, Franklin Lakes, N.J.). The blank (untreated cells) was used to establish the gate of non-positive cell activity. CD133 was expressed on both head and neck cancer cell lines, NA and UMSC-11B, at 5.9% and 6% respectively (Table 13). The Caco-2 colorectal carcinoma was included as a positive control cell line since it known to overexpress CD133. Controls included cells reacted with anti-EpCam-FITC, anti-CD45-FITC, and anti-CD19-FITC. Expression of CD45 and CD19 is mostly restricted to normal malignant hematopoietic cells.

TABLE 13

| Cell Line | CD133$^+$ | EpCam$^+$ | CD45$^+$ | CD119$^+$ |
|---|---|---|---|---|
| NA | 5.9 | — | — | 1.1 |
| UMSCC-11B | 6.0 | 98.0 | 0.5 | 0.3 |
| Caco-2 | 80.0 | — | — | 0.8 |

Example 20 dCD133KDEL Inhibits the Human Head and Neck Cancer Cell Line NA In Vitro

Figure 17:
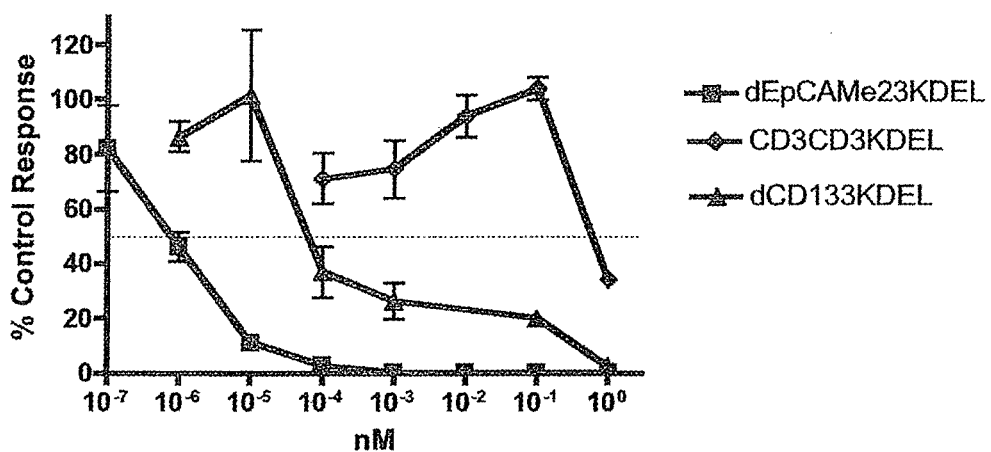
FIG. 17: The effect of dCD133KDEL on NA head and neck cancer cells. dCD133KDEL was tested on the NA cell line using a $^3$H-leucine incorporation protein synthesis assay. CD3CD3KDEL was included as negative control. dEpCAM23 was included as a positive control because of the high EpCAM expression on this cell line. Data is expressed as percentage of $^3$H-leucine incorporation relative to control cells incubated in media alone.

NA cells (10$^4$/well) were plated in 96-well flat-bottomed plates and incubated overnight at 37° C. at 5% CO$_2$. dCD133KDEL in varying concentrations was added to wells in triplicate. Incubation continued for 72 hours and [Methyl-$^3$H]-Leucine (GE Healthcare, UK) was added (1 µCi per well) for the final 24 hours of incubation. Plates were frozen to detach cells and then harvested. Data is expressed as percentage of $^3$H-leucine incorporation relative to control cells incubated in media alone. dCD133KDEL inhibited protein synthesis activity. Control anti-T cell does not react with NA cells and did not inhibit activity. dEpCAM23KDEL was included as a positive control because of the high EpCAM expression on this cell line. Results are shown in FIG. 17.

Example 21

CD133-Immunoparticles

Cell Culture

Caco-2 cells were obtained from ATCC and were cultured in Minimum Essential Medium (MEM) containing 20% FBS (Invitrogen, Carlsbad, Calif.), 1% non-essential amino acids (Sigma-Aldrich Corp., St. Louis, Mo.), 1% sodium pyruvate (Sigma-Aldrich Corp., St. Louis, Mo.) and 1% penicillin-streptomycin (Sigma-Aldrich Corp., St. Louis, Mo.) at 37° C./5% CO$_2$ in a humidified incubator.

Preparation of Maleimide Functionalized PLGA Nanoparticles Loaded with 6-Coumarin PLGA (30 mg) and 6-coumarin (250 µg) were dissolved in 1 ml of chloroform. An oil-in-water emulsion was formed by emulsifying the polymer solution in 8 ml of 2.5% w/v aqueous PVA solution by probe sonication (18-24 W, Sonicator XL, Misonix, Inc., Farmingdale, N.Y.) for five minutes over an ice bath. The diblock copolymer PLA-PEG-MAL (8 mg) was dissolved in chloroform (200 µl) and added dropwise to the above emulsion with stirring. The emulsion was stirred for 18 hours at ambient conditions followed by two hours under vacuum to remove the residual chloroform. Nanoparticles were recovered by ultracentrifugation (35,000 rpm for 35 minutes at 4° C., Optima LE-80K, Beckman Coulter, Inc., Brea, Calif.) and washed three times with deionized water. Nanoparticle suspension was then lyophilized (FreeZone 4.5, Labconco Corp., Kansas City, Mo.) to obtain a dry powder.

Conjugation of CD133 Antibody to Maleimide Functionalized Poly(Lactic-Co-Glycolic Acid (PLGA) Nanoparticles Loaded with 6-Coumarin Iminothiolation of CD133 Antibody:

20 µg of CD133 antibody (AC 141, Miltenyi Biotec, Auburn, Calif.) was diluted to a final volume of 1 ml with sodium phosphate buffer (pH 8) containing 150 mM sodium chloride. To this, 4 µl of 1 mM solution of 2-Iminothiolane freshly prepared in sodium phosphate/sodium chloride buffer was added and incubated for two hours at 4° C. in a rotator. The iminothiolated antibody solution was de-salted and buffer exchanged with Hepes buffer mixture (50 mM Hepes, pH 7.4, 150 mM sodium chloride, 2 mM EDTA) using Zeba desalting column (Pierce, Rockford, Ill.) by following the manufacturer's protocol. The desalted antibody solution was further concentrated using ultra-4 centrifugal filter unit (AMICON, Millipore Corp., Billerica, Mass.) by centrifugation at 4000 rpm, 4° C. for 30 minutes.

Conjugation of Antibody with Malemide Functionalized PLGA Nanoparticles:

The concentrated antibody solution (approximately 200 µl) obtained in the previous step was added to 15 mg of malemide functionalized PLGA nanoparticles, loaded with fluorescent 6-coumarin dye, dispersed in 750 µl Hepes buffer mixture and incubated at room temperature for about 4.5 hours in a rotator. The particles were pelleted by centrifugation (either at 14000 rpm for 30 minutes in a bench-top centrifuge or 30000 rpm for 30 minutes in an ultracentrifuge) and washed twice with autoclaved de-ionised water. Nanoparticle suspension was then lyophilized (FreeZone 4.5, Labconco Corp., Kansas City, Mo.) to obtain a dry powder.

Figure 18:
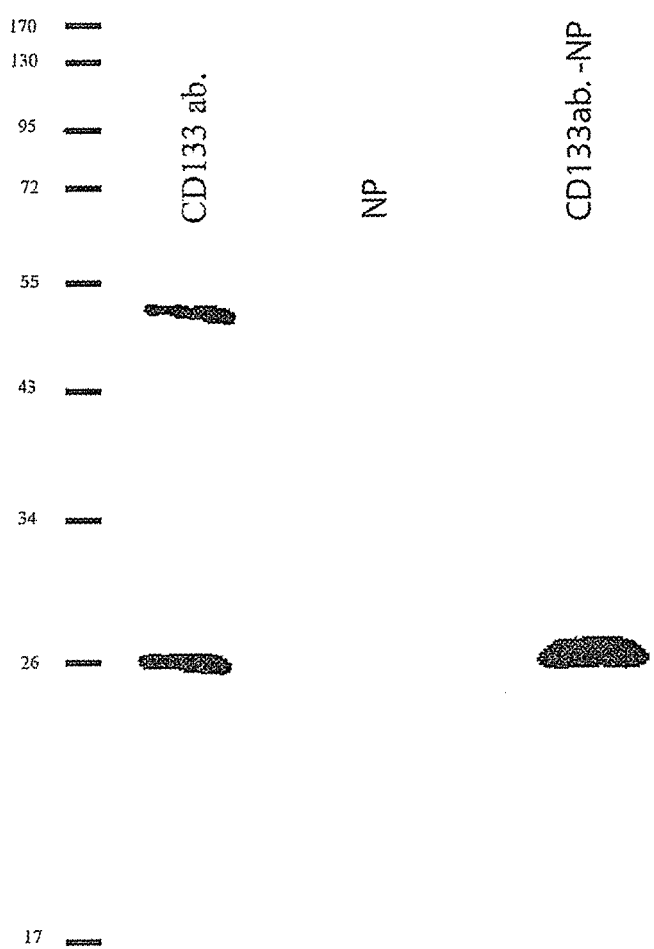
FIG. 18: Western blot showing binding of anti-mouse IgG to CD133 antibody-conjugated nanoparticles (lane 3) but not to unconjugated nanoparticles (lane 2).

Western Blot of CD133-Nanoparticles 1 mg of PLGA particles (plain or conjugated with CD133 antibody) was dispersed in 25 µl of 2× gel loading buffer (Bio-Rad Laboratories, Inc., Hercules, Calif.) supplemented with 2-mercaptoethanol and incubated at room temperature for 30 minutes in a rotating shaker. The tubes were placed in a water bath heated to 82° C. for five minutes and then centrifuged to pellet the nanoparticles. About 20 µl of the supernatant is resolved by a 12.5% SDS-PAGE gel and transferred onto a nitrocellulose membrane (Whatman Inc., Piscataway, N.J.) using a criterion blotter (Bio-Rad Laboratories, Inc., Hercules, Calif.). The membrane was blocked with 5% non-fat dry milk in TBST overnight at 4° C. and then incubated with anti-mouse IgG conjugated to horseradish peroxidase (HRP, EMD Chemicals, Gibbstown, N.J.) in 5% non-fat dry milk/TBST for 1.5 hours at room temperature. The membrane was then washed three times with TBST and visualized using SUPERSIGNAL WEST PICO chemiluminescent substrate (Pierce, Rockford, Ill.). Results are shown in FIG. 18.

Immunostaining of Caco-2 Cells Using CD133-Immunnoparticles

Figure 20:
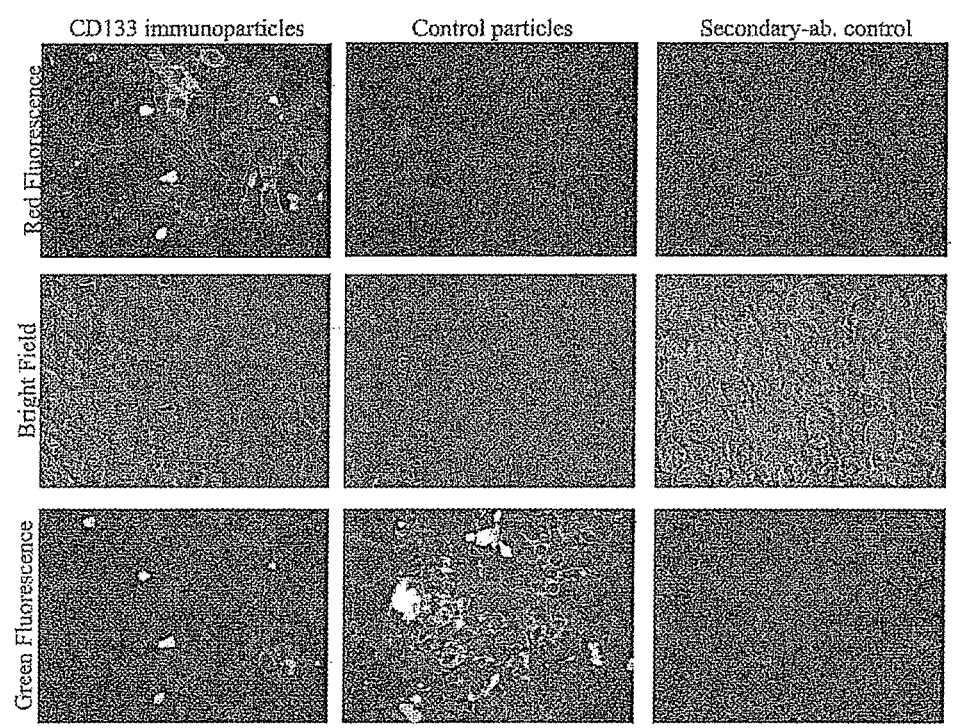
FIG. 20: Fluorescent immunostaining of Caco-2 cells using CD133-immunoparticles.

Caco-2 cells were plated in 16-well chamber slides. After 4 days of growth, the cells were fixed with 4% paraformaldehyde, washed in DPBS and then incubated in 200 mM glycine for 10 minutes. The cells were then blocked with a solution of 0.5% BSA and 0.2% gelatin in PBS for 10 minutes. This was followed by incubation with a suspension of CD133 antibody conjugated PLGA particles loaded with 6-coumarin prepared in blocking solution or relevant controls (negative control: unconjugated PLGA particles loaded with 6-coumarin and secondary antibody control; positive control: anti-CD133 antibody AC141, Miltenyi Biotec, Auburn, Calif.) at 4° C. for two hours. The cells were washed three times with PBS and stained with ALEXA 594 coupled anti-mouse IgG (Invitrogen, Carlsbad, Calif.) in for one hour at room temperature. The cells were further washed with PBS and visualized under a fluorescence microscope. Images were taken using ProgRes C3® software (Jenoptik AG, Jena, Germany) and processed using Photoshop (Adobe Systems, Inc., San Jose, Calif.). Results are shown in FIG. 20.

Flow Cytometry

Figure 19:
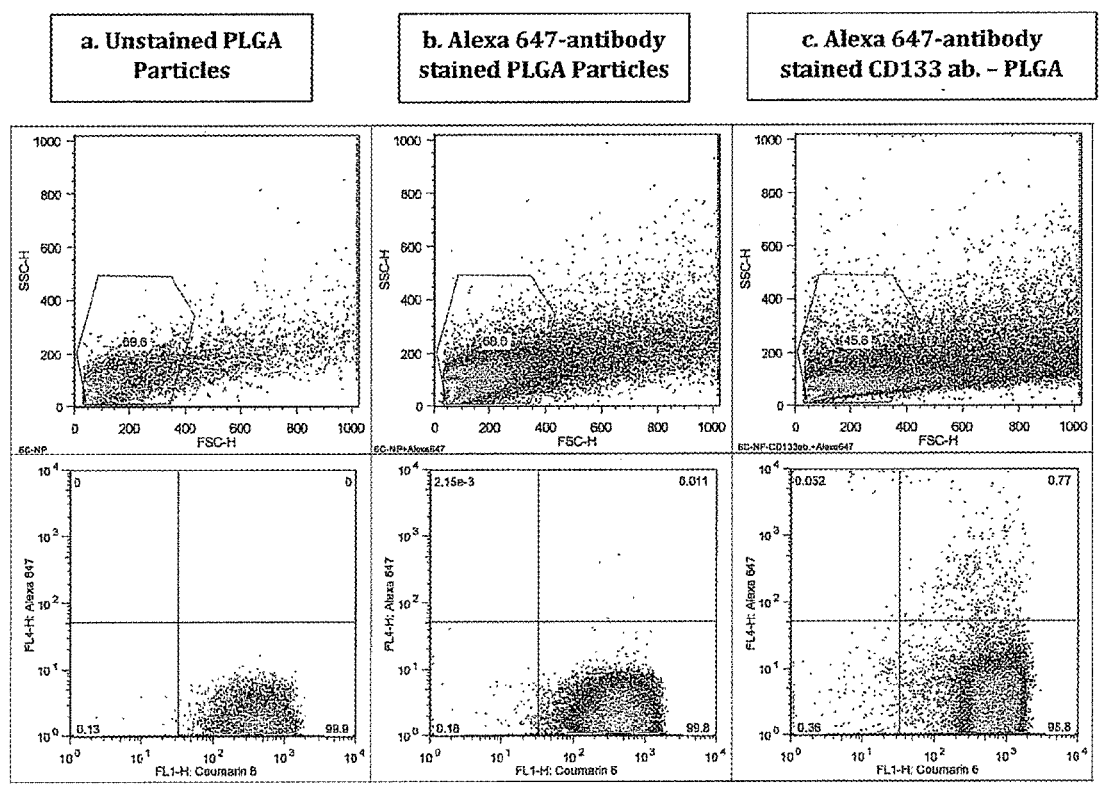
FIG. 19: Flow cytometry data of PLGA particles loaded with 6-coumarin and either conjugated to CD133 antibody (c) or unconjugated (b).

PLGA particles (plain or conjugated with CD133 antibody) loaded with 6-coumarin were dispersed in PBS, to a final concentration of 1 mg/ml, and incubated with ALEXA 647 coupled anti-mouse IgG (Invitrogen, Carlsbad, Calif.) for two hours at room temperature in a rotator. The particles were pelleted down by centrifugation at 12000 rpm for five minutes, washed once with PBS and then analyzed by flow cytometry. Results are shown in FIG. 19.

Uptake of CD133 Antibody Conjugated PLGA Particles in Caco-2 Cells

Figure 21:
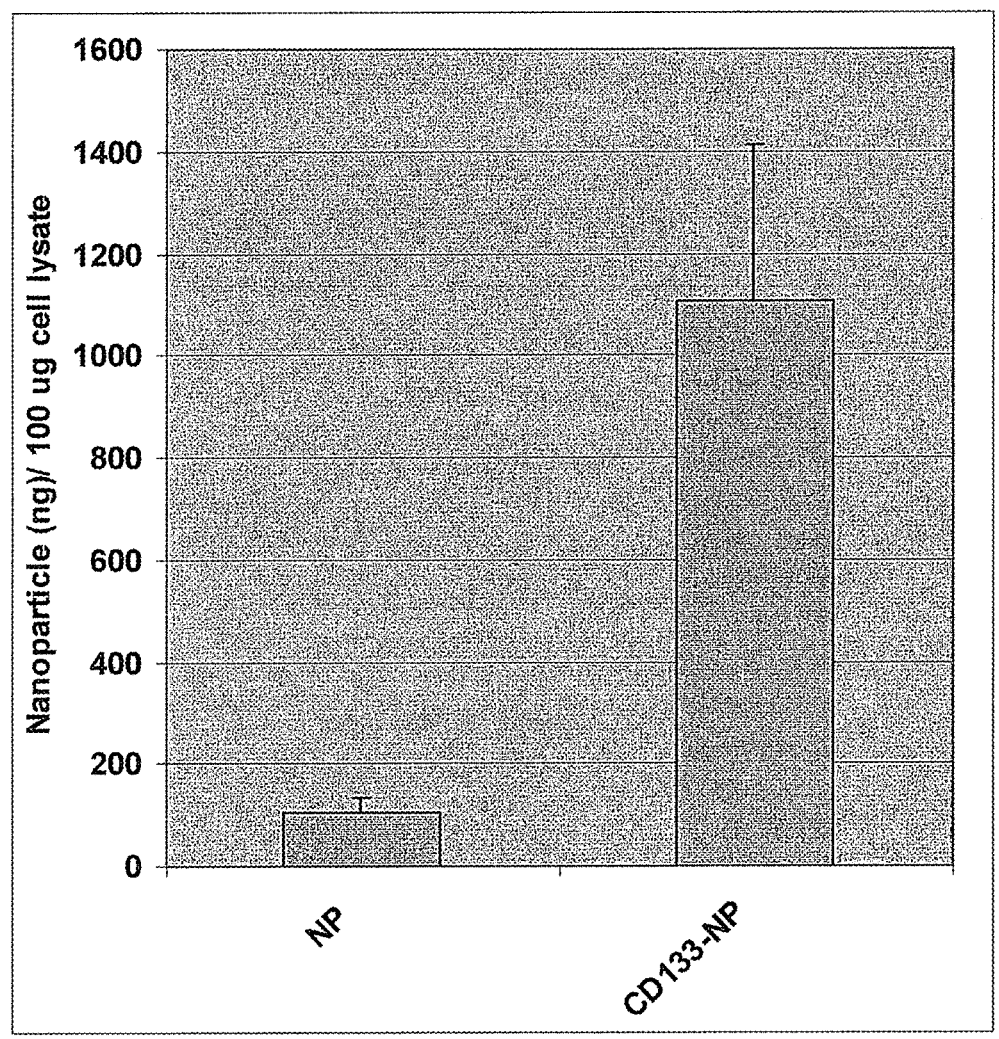
FIG. 21: CD133-conjugated nanoparticle (CD133-NP) and unconjugated nanoparticle (NP) content of Caco-2 cell lysates. Caco-2 cells exhibited greater uptake of CD133-conjugated nanoparticles.

Caco-2 cells were seeded in 24-well plates and cultured in 5% $CO_2$ incubator. When confluent, cells were subjected to the following series of steps: First, the complete growth media was replaced with a reduced serum media (containing 2% FCS) and incubated for 45 minutes. This was followed by incubation with either CD133 antibody conjugated PLGA particles or PLGA particles (40 µg/well) dispersed in reduced serum media at 4° C. for one hour. Next, the nanoparticle treatments were removed, washed once with PBS, and then cells were fed with complete growth medium and incubated at 37° C. for one hour. Cells were then washed with PBS and lysed using 1% w/v Triton X-100 in 8 mM potassium phosphate buffer. A part of the cell lysate was lyophilized and extracted with methanol. The 6-coumarin concentration in the methanol extracts was determined by HPLC analysis. Nanoparticle concentration in the cell lysate was normalized to the total cell protein determined using BCA protein assay kit (Pierce, Rockford, Ill.). Results are shown in FIG. 21.

Example 22

Mice tolerate systemic treatment with dCD133KDEL very well. Mice were given an intraperitoneal injection of either 20 µg, 50 µg, or 100 µg dCD133KDEL, a day of rest, and then a second intraperitoneal injection. Survival is shown in Table 14. All animals survived with minimal weight loss indicating that that the drug is well tolerated and minimally toxic in vivo.

TABLE 14

| Dose Level | Survivors/Total mice | % Surviving |
|---|---|---|
| 20 µg | 3/3 | 100 |
| 50 µg | 3/3 | 100 |
| 100 µg | 1/1 | 100 |

Example 23

Figure 22:
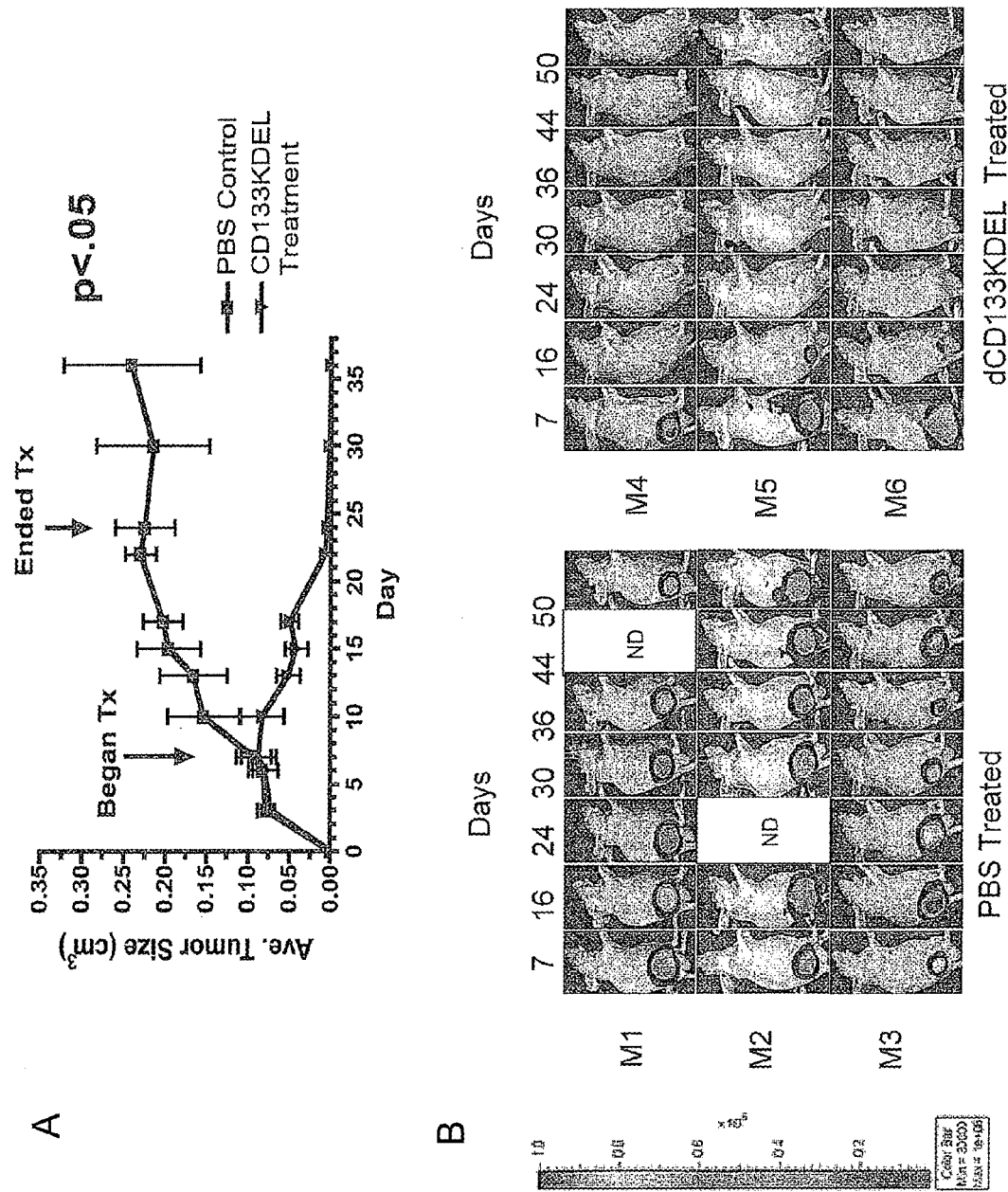
FIG. 22: The effect of dCD133KDEL on in vivo tumor progression in nude mice with human head and neck flank tumors. A) Tumor volume was measured with calipers. B) Bioluminescence images of treated (dCD133KDEL Treated) and untreated (PBS Treated) mice over time.

The effect of dCD133KDEL on in vivo tumor progression in nude mice with human head and neck flank tumors. Flank tumor progression is an accepted in vivo model for studying head and neck cancer so mice (n=5/group) were given flank injections of 3 million UMSCC-11B cells. Intratumoral treatment of the mice was begun on Day-6 post-tumor inoculation with dCD133KDEL. A single course of treatment consisted of an injection of 20 µg of drug given every other day (MWF) and mice were given 8 injections. In A, tumor volume was measured with calipers over time. The arrows indicate where treatment (Tx) began and ended. In B, animals were imaged weekly. Bioluminescence intensity was measured as a function of photons/sec/sr/$cm^2$. Controls were treated with PBS. Mice were imaged in real time and images were captured using Xenogen Ivis imaging system (Xenogen Corporation, Hopkington Mass.) and analyzed IGOR Pro 4.09a software (WaveMetrics, Inc., Portland, Oreg.). Prior to imaging, mice were anesthetized using isoflurane gas. All mice received 100 µl of a 30 mg/ml D-luciferin aqueous solution (Gold Biotechnology, St. Louis, Mo.) as a substrate for luciferase 10 minutes before imaging. All images represent a five minute exposure time and all regions of interest (ROI) are expressed in units of photons/sec/sr/$cm^2$. Representative animals from both groups are shown. M4-M6 treated with dCD133KDEL were completely responded and were tumor free after 50 days, while controls did not respond. Results are shown in FIG. 22. (ND—No data)

Example 24

Figure 23:
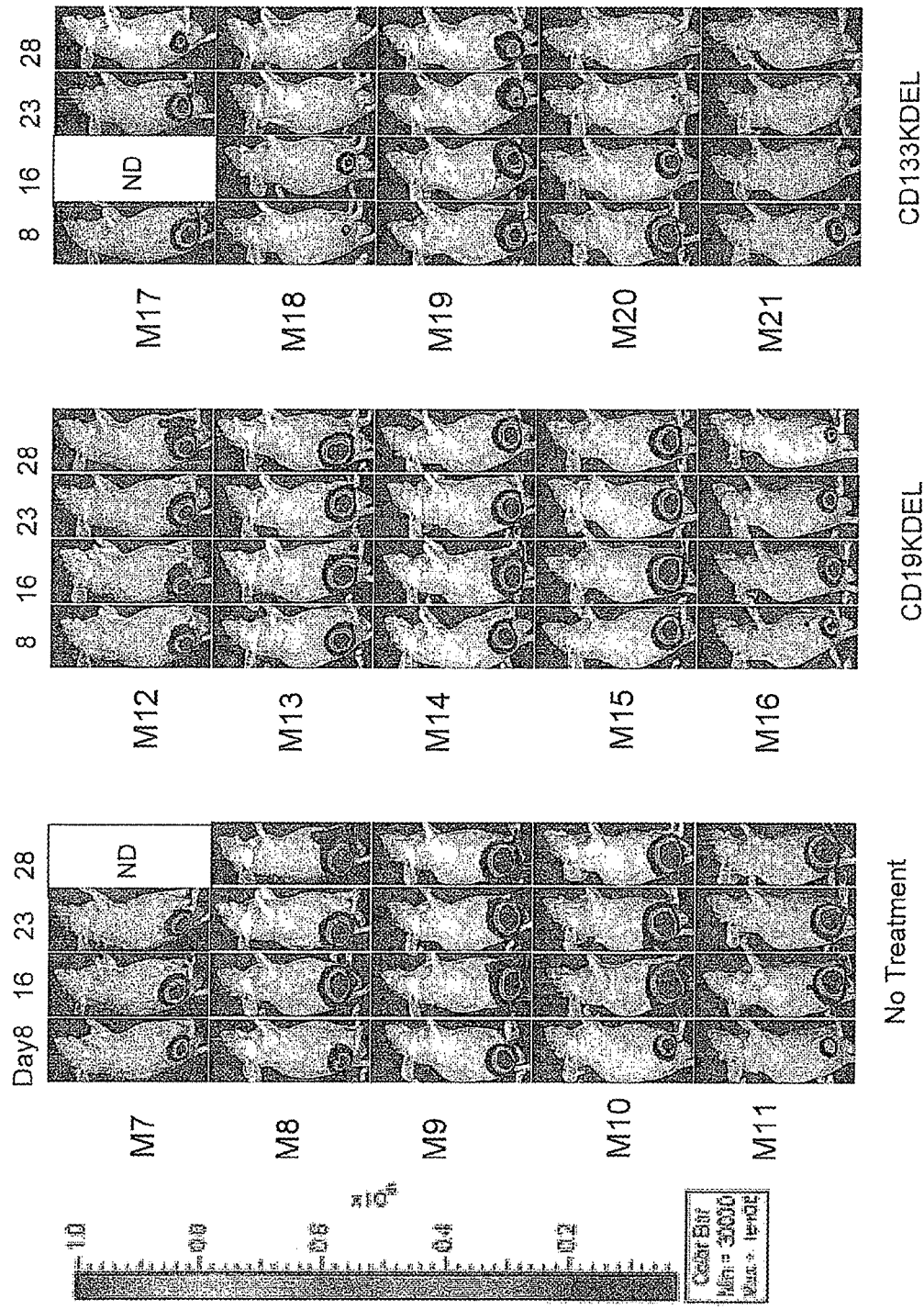
FIG. 23: The effect of dCD133KDEL on in vivo tumor progression in nude mice with human head and neck flank tumors. Bioluminescence images of treated (CD133KDEL), untreated (No Treatment), and control (CD19KDEL) mice over time.

The effect of dCD133KDEL on in vivo tumor progression in nude mice with human head and neck flank tumors. This Example was performed nearly identically to Example 23, except tumors were induced in nude by intratumoral injection of more cells (6 million) and treatment of mice was begun on Day 10 post-tumor inoculation with dCD133KDEL. Nude mice (n=5/group) were given flank injections of UMSCC-11B cells. Intratumoral treatment of the mice was begun on Day 10 post-tumor inoculation with dCD133KDEL. A single course of treatment consisted of an injection of 20 μg of drug given every other day (MWF) and mice were given 8 injections. Controls were treated with negative control anti-B cell CD19KDEL or not treated at all. Bioluminescence intensity was measured as a function of photons/sec/sr/cm$^2$. Controls were treated with PBS. Mice were imaged in real time and images were captured using Xenogen Ivis imaging system All regions of interest (ROI) are expressed in units of photons/sec/cm2/sr. Sixty percent of the animals (3 of 5) responded completely to dCD133KDEL treatment with no detectable tumor growth, while none of the controls responded. Results are shown in FIG. 23. (ND—no data.)

Example 25

Cell Culture

Patient 9 (P9-F) cell line has been recently established from a human patient diagnosed with GBM and made to express a luciferase reporter gene under 2 μg/ml puromycin selection. Cells were maintained as suspended neurospheres in serum-free DMEM/F12 media supplemented with 1% non-essential amino acids (Sigma-Aldrich Corp., St. Louis, Mo.), 1% penicillin-streptomycin (Sigma-Aldrich Corp., St. Louis, Mo.), B27, N2, Blasticidin (Invivogen, Carlsbad, Calif.) and 20 ng/ml EGF and FGF. Cells were incubated in a humidified 37° C. atmosphere containing 5% $CO_2$. Prior to intracranial injection, P9-F neurospheres were centrifuged and dissociated in Non-Enzymatic Cell Dissociation Buffer (Sigma-Aldrich Corp., St. Louis, Mo.) to form a single-cell suspension. Cell number and viability were determined via trypan blue exclusion on a Countess automated cell counter (Invitrogen, Carlsbad, Calif.).

P9-F Intracranial (IC) Injection

Athymic nu/nu mice were anesthetized with intraperitoneal injection of a cocktail of 54 mg/ml Ketamine and 9.2 mg/ml Xylazine and place in a Kopf stereotactic head frame. The scalp was swabbed with betadine and a midline incision was made with a scalpel. A burr hole was placed 2.5 mm lateral and 0.5 mm anterior from sagittal midline located bregma. A Hamilton syringe (26 gauge) was used to deliver P9-F cells to a 3.3 mm depth from skull surface to about the middle of caudate-putamen. Tumor growth was evaluated by bioluminescent imaging.

scFvCD133-KDEL Intraperitoneal (IP) Injection

One week after IC injection of P9-F cells, mice (n=6) were injected IP with 10 scFvCD133-KDEL. Twenty minutes prior to injection of scFvCD133-KDEL, one group (n=7) was given 2 mg/kg 25% mannitol IP to facilitate osmotic blood-brain barrier (BBB) disruption. Dosing regimen consisted of five days continuous treatment, two days rest, followed by five days continuous treatment with 20 μg scFvCD133-KDEL.

Figure 24:
FIG. 24: Photographs showing tumor regression in nu/nu mice with human glioblastoma xenografts treated with scFvCD133-KDEL. A) Tumor signal pre-treatment, seven days after intraperitoneal injection of human glioblastoma cells; B) Tumor signal following 14 days of treatment with scFvCD133-KDEL.
Figure 24:
Figure 24:
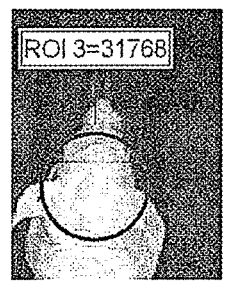

Mice were injected intraperitoneally with D-luciferin and anesthetized with isoflurane. 15 minutes later, mice were placed in a Xenogen IVIS Imaging System and imaged for five minutes. Results are shown in FIG. 24. Red circles represent regions of interest (ROI) which quantify photon flux.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

SEQ ID NO: 1

MALVLGSLLLLGLCGNSFSGGQPSSTDAPKAWNYELPATNYETQDSHKAG

PIGILFELVHIFLYVVQPRDFPEDTLRKFLQKAYESKIDYDKPETVILGL

KIVYYEAGIILCCVLGLLFIILMPLVGYFFCMCRCCNKCGGEMHQRQKEN

GPFLRKCFAISLLVICIIISIGIFYGFVANHQVRTRIKRSRKLADSNFKD

LRTLLNETPEQIKYILAQYNTTKDKAFTDLNSINSVLGGGILDRLRPNII

PVLDEIKSMATAIKETKEALENMNSTLKSLHQQSTQLSSSLTSVKTSLRS

SLNDPLCLVHPSSETCNSIRLSLSQLNSNPELRQLPPVDAELDNVNNVLR

TDLDGLVQQGYQSLNDIPDRVQRQTTTVVAGIKRVLNSIGSDIDNVTQRL

PIQDILSAFSVYVNNTESYIHRNLPTLEEYDSYWWLGGLVICSLLTLIVI

FYYLGLLCGVCGYDRHATPTTRGCVSNTGGVFLMVGVGLSFLFCWILMII

VVLTFVFGANVEKLICEPYTSKELFRVLDTPYLLNEDWEYYLSGKLFNKS

KMKLTFEQVYSDCKKNRGTYGTLHLQNSFNISEHLNINEHTGSISSELES

LKVNLNIFLLGAAGRKNLQDFAACGIDRMNYDSYLAQTGKSPAGVNLLSF

AYDLEAKANSLPPGNLRNSLKRDAQTIKTIHQQRVLPIEQSLSTLYQSVK

ILQRTGNGLLERVTRILASLDFAQNFITNNTSSVIIEETKKYGRTIIGYF
EHYLQWIEFSISEKVASCKPVATALDTAVDVFLCSYIIDPLNLFWFGIGK
ATVFLLPALIFAVKLAKYYRRMDSEDVYDDVETIPMKNMENGNNGYHKDH
VYGIHNPVMTSPSQH

SEQ ID NO: 2
NHQVRTRIKRSRKLADSNFKDLRTLLNETPEQIKYILAQYNTTKDKAFTD
LNSINSVLGGGILDRLRPNIIPVLDEIKSMATAIKETKEALENMNSTLKS
LHQQSTQLSSSLTSVKTSLRSSLNDPLCLVHPSSETCNSIRLSLSQLNSN
PELRQLPPVDAELDNVNNVLRTDLDGLVQQGYQSLNDIPDRVQRQTTTVV
AAAGRKNLQDFAACGIDRMNYDSYLAQTGKSPAGVNLLSFAYDLEAKANS
LPPGNLRNSLKRDAQTIKTIHQQRVLPIEQSLSTLYQSVKILQRTGNGLL
ERVTRILASLDFAQNFITNNTSSVIIEETKKYGRTIIGYFEHYLQWIEFS
ISEKV

SEQ ID NO: 47
<u>AQAAELDIVLTQSPAIMSASPGEKVTISCSASSSVGYMYWYQQKPGSSPK</u>
<u>PWIYRPSNLASGVPARFSGSGSGTSYSLTISSMEAEDAATYYCQQYHSYP</u>
<u>PTFGAGTKLELKS</u>SGGGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQ*
Key:
Underlined: VL
Plain text: linker
Italics: VH SEQ ID NO: 48
<u>AQAAELDIVLTQSPAIMSASPGEKVTISCSASSSVSYMYWYQQKPGSSPK</u>
<u>PWIYRTSNLASGVPARFSGSGSGTSYSLTISSMEAEDAATYYCQQYHSYP</u>
<u>PTFGAGTKLELKS</u>SGGGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQAGQ*
Key:
Underlined: VL
Plain text: linker
Italics: VH SEQ ID NO: 49
<u>AQAAELDIVLTQSPAIMSASPGEKVTISCSASSSVSYMYWYQQKPGSSPK</u>
<u>PWIYRPSNLASGVPARFSGSGSGTSYSLTISSMEAEDAATYYCQQYHSYP</u>
<u>PTFGAGTKLELKS</u>SGGGGSGGGGGSSRSS*PEVMLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQAGQ*
Key:
Underlined: VL
Plain text: linker
Italics: VH SEQ ID NO: 50
<u>AQAAELDIVLTQSPAIMSASPGEKVTISCSASSSVSYMYWYQQKPGQPPR</u>
<u>LLIYLVSNLESGVPARFSGSGSGTDFTLNIHPVEEEDAATYYCQQYHSYP</u>
<u>PTFGAGTKLEIKS</u>SGGGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQAGQ*
Key:
Underlined: VL
Plain text: linker
Italics: VH SEQ ID NO: 51
<u>AQAAELDIVLTQSPAIMSASPGEKVTISCSASSSVSYMYWYQQKPGSSPK</u>
<u>PWIYRPSNLASGVPARFSGSGSGTSYSLTISSMEAEDAATYYCQQYHSYP</u>
<u>PTFGAGTKLELKS</u>SGGGGSGGGGGSSRSS*LEVHLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQAGQ*
Key:
Underlined: VL
Plain text: linker
Italics: VH SEQ ID NO: 52
<u>AQAAELDIVLSQSPAIMSASPGEKVTISCSASSSVSYMYWYQQKPGSPPK</u>
<u>PWIYRTSNLASGVPARFSGSGSGTSYSLTISSMEAEDAATYYCQQYHSYP</u>
<u>PTFGAGTKLELKS</u>SGGGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDCGDYFDYWGQGTTLTVSSAK*
*TTPPSVTSGQAGQ*
Key:
Underlined: VL
Plain text: linker
Italics: VH SEQ ID NO: 53
<u>AQAAELDIVLSQSPAIMSASPGEKVTISCSASSSVSYMYWYQQKPGSSPK</u>
<u>PWIYRTSNLASGVPARFSGSGSGTSYSLTISSMEAEDAATYYCQQYHSYP</u>
<u>PTFGAGTKLELKS</u>SGGGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTPPSVTSGQAGQ*
Key:
Underlined: VL
Plain text: linker
Italics: VH SEQ ID NO: 54
<u>AQAAELDIVLTQSPAIMSASPGEKVTISCSASSSVSYMYWYQQKPGSSPK</u>
<u>PWIYRPSNLASGVPARFSGSGSGTSYSLTISSMEAEDAATYYCQQYHSYP</u>
<u>PTFGAGTKLELKS</u>SGDGGSGGGGGSSRSS*LEVKLVESGPELKKPGETVK*
*ISCKASGYTFTDYSMHWVNQAPGKGLKWMGWINTETGEPSYADDFKGRFA*
*FSLETSASTAYLQINNLKNEDTATYFCATDYGDYFDYWGQGTTLTVSSAK*
*TTAPSVTSGQAGQ*
Key:
Underlined: VL
Plain text: linker
Italics: VH SEQ ID NO: 55
AQAAELDIVLTQSPAIMSASPGEKVTISCSASSSVSYMYWYQQKPGSSPK
PWIYRPSNLASGVPARFSGSGSGTSYSLTISSMEAEDAATYYCQQYHSYP
PTFGAGTKLELKSSGGGGSGGGGGGSSRSSLEVQLVESGPELKKPGETVK
ISCKASGYTFTDYSMHWVNQAPGKGLKWMGWINTETGEPSYADDFKGRFA
FSLETSASTAYLQINNLKNEDTATYFCATDYGDYFDYWGQGTTLTVSSAK
TTAPSVTSGQAGQ Key:
Underlined: VL
Plain text: linker
Italics: VH SEQ ID NO: 56
GGCCCAGGCGGCCGAGCTCGACATTGTTCTCTCCCAGTCTCCAGCAATCA
TGTCTGCATCTCCAGGGGAGAAGGTCACCATATCCTGCAGTGCCAGCTCA
AGTGTAAGTTATATGTACTGGTACCAGCAGAAGCCAGGATCCTCCCCCAAA
CCCTGGATTTATCGCACATCCAACCTGGCTTCTGGAGTCCCTGCTCGCTT
CAGTGGCAGTGGGTCTGGGACCTCTTACTCTCTCACAATCAGCAGCATGG
AGGCTGAAGATGCTGCCACTTATTACTGCCAGCAGTATCATAGTTACCCA
CCCACGTTCGGTGCTGGGACCAAGCTGGAGCTGAAATCCTCTGGTGGCGG
TGGCTCGGGCGGTGGTGGGGGTGGTTCCTCTAGATCTTCCCTCGAGGTGA
AGCTGGTGGAGTCTGGACCTGAGCTGAAGAAGCCTGGAGAGACAGTCAAG
ATCTCCTGCAAGGCTTCTGGTTATACCTTCACAGACTATTCAATGCACTG
GGTGAATCAGGCTCCAGGAAAGGGTTTAAAGTGGATGGGCTGGATAAACA
CTGAGACTGGTGAGCCATCATATGCAGATGACTTCAAGGGACGGTTTGCC
TTCTCTTTGGAAACCTCTGCCAGCACTGCCTATTTGCAGATCAACAACCT
CAAAAATGAGGACACGGCTACATATTTCTGTGCTACCGATTACGGGGACT
ACTTTGACTACTGGGGCCAAGGCACCACTCTCACAGTCTCCTCAGCCAAA
ACGACACCCCCATCTGTCACTAGTGGCCAGGCCGGCCAGCACCATCACCA
TCACCATGGCGCATACCCGTACGACGTTCCGGACTACGCTTCTTAG Key:
Underlined: SfiI site
Italics: linker
Bold: 6HIS tag
Underlined italics: HA tag
Bold underlined: amber stop codon SEQ ID NO: 57
ATGGACATTGTTCTCTCCCAGTCTCCAGCAATCATGTCTGCATCTCCAGG
GGAGAAGGTCACCATATCCTGCAGTGCCAGCTCAAGTGTAAGTTATATGT
ACTGGTACCAGCAGAAGCCAGGATCCTCCCCCAAACCCTGGATTTATCGC
ACATCCAACCTGGCTTCTGGAGTCCCTGCTCGCTTCAGTGGCAGTGGGTC
TGGGACCTCTTACTCTCTCACAATCAGCAGCATGGAGGCTGAAGATGCTG
CCACTTATTACTGCCAGCAGTATCATAGTTACCCACCCACGTTCGGTGCT
GGGACCAAGCTGGAGCTGAAATCCTCTGGTGGCGGTGGCTCGGGCGGTGG
TGGGGGTGGTTCCTCTAGATCTTCCCTCGAGGTGAAGCTGGTGGAGTCTG
GACCTGAGCTGAAGAAGCCTGGAGAGACAGTCAAGATCTCCTGCAAGGCT
TCTGGTTATACCTTCACAGACTATTCAATGCACTGGGTGAATCAGGCTCC
AGGAAAGGGTTTAAAGTGGATGGGCTGGATAAACACTGAGACTGGTGAGC CATCATATGCAGATGACTTCAAGGGACGGTTTGCCTTCTCTTTGGAAACC
TCTGCCAGCACTGCCTATTTGCAGATCAACAACCTCAAAAATGAGGACAC
GGCTACATATTTCTGTGCTACCGATTACGGGGACTACTTTGACTACTGGG
GCCAAGGCACCACTCTCACAGTCTCCTCA SEQ ID NO: 58
MDIVLSQSPAIMSASPGEKVTISCSASSSVSYMYWYQQKPGSSPKPWIYR
TSNLASGVPARFSGSGSGTSYSLTISSMEAEDAATYYCQQYHSYPPTFGA
GTKLELKSSGGGGSGGGGGGSSRSSLEVKLVESGPELKKPGETVKISCKA
SGYTFTDYSMHWVNQAPGKGLKWMGWINTETGEPSYADDFKGRFAFSLET
SASTAYLQINNLKNEDTATYFCATDYGDYFDYWGQGTTLTVSS EGF nucleotide:
SEQ ID NO: 59
AACAGCGACAGCGAATGTCCGCTGAGCCACGACGGTTACTGTCTGCACGA
CGGTGTTTGTATGTACATCGAAGCTCTAGACAAATACGCTTGTAACTGTG
TTGTTGGTTACATCGGTGAACGCTGTCAGTACCGCGACCTGAAATGGTGG
GAACTGCGC EGF amino acid:
SEQ ID NO: 60
NSDSECPLSHDGYCLHDGVCMYIEALDKYACNCVVGYIGERCQYRDLKWW
ELR DT nucleotide:
SEQ ID NO: 61
ATGGGCGCTGATGATGTTGTTGATTCTTCTAAATCTTTTGTGATGGAAAA
CTTTTCTTCGTACCACGGGACTAAACCTGGTTATGTAGATTCCATTCAAA
AAGGTATACAAAAGCCAAAATCTGGTACACAAGGAAATTATGACGATGAT
TGGAAAGGGTTTTATAGTACCGACAATAAATACGACGCTGCGGGATACTC
TGTAGATAATGAAAACCCGCTCTCTGGAAAAGCTGGAGGCGTGGTCAAAG
TGACGTATCCAGGACTGACGAAGGTTCTCGCACTAAAAGTGGATAATGCC
GAAACTATTAAGAAAGAGTTAGGTTTAAGTCTCACTGAACCGTTGATGGA
GCAAGTCGGAACGGAAGAGTTTATCAAAAGGTTCGGTGATGGTGCTTCGC
GTGTAGTGCTCAGCCTTCCCTTCGCTGAGGGGAGTTCTAGCGTTGAATAT
ATTAATAACTGGGAACAGGCGAAAGCGTTAAGCGTAGAACTTGAGATTAA
TTTTGAAACCCGTGGAAAACGTGGCCAAGATGCGATGTATGAGTATATGG
CTCAAGCCTGTGCAGGAAATCGTGTCAGGCGATCAGTAGGTAGCTCATTG
TCATGCATAAATCTTGATTGGGATGTCATAAGGGATAAAACTAAGACAAA
GATAGAGTCTTTGAAAGAGCATGGCCCTATCAAAAATAAAATGAGCGAAA
GTCCCAATAAAACAGTATCTGAGGAAAAAGCTAAACAATACCTAGAAGAA
TTTCATCAAACGGCATTAGAGCATCCTGAATTGTCAGAACTTAAAACCGT
TACTGGGACCAATCCTGTATTCGCTGGGGCTAACTATGCGGCGTGGGCAG
TAAACGTTGCGCAAGTTATCGATAGCGAAACAGCTGATAATTTGGAAAAG
ACAACTGCTGCTCTTTCGATACTTCCTGGTATCGGTAGCGTAATGGGCAT
TGCAGACGGTGCCGTTCACCACAATACAGAAGAGATAGTGGCACAATCAA
TAGCTTTATCGTCTTTAATGGTTGCTCAAGCTATTCCATTGGTAGGAGAG
CTAGTTGATATTGGTTTCGCTGCATATAATTTTGTAGAGAGTATTATCAA DT amino acid:
SEQ ID NO: 62

MGADDVVDSSKSFVMENFSSYHGTKPGYVDSIQKGIQKPKSGTQGNYDDD
WKGFYSTDNKYDAAGYSVDNENPLSGKAGGVVKVTYPGLTKVLALKVDNA
ETIKKELGLSLTEPLMEQVGTEEFIKRFGDGASRVVLSLPFAEGSSSVEY
INNWEQAKALSVELEINFETRGKRGQDAMYEYMAQACAGNRVRRSVGSSL
SCINLDWDVIRDKTKTKIESLKEHGPIKNKMSESPNKTVSEEKAKQYLEE
FHQTALEHPELSELKTVTGTNPVFAGANYAAWAVNVAQVIDSETADNLEK
TTAALSILPGIGSVMGIADGAVHHNTEEIVAQSIALSSLMVAQAIPLVGE
LVDIGFAAYNFVESIINLFQVVHNSYNRPAYSPGHKTQPF

IL-13 nucleotide:
SEQ ID NO: 63

GGCCCTGTGCCTCCCTCTACAGCCCTCAGGGAGCTCATTGAGGAGCTGGT
CAACATCACCCAGAACCAGAAGGCTCCGCTCTGCAATGGCAGCATGGTAT
GGAGCATCAACCTGACAGCTGGCATGTACTGTGCAGCCCTGGAATCCCTG
ATCAACGTGTCAGGCTGCAGTGCCATCGAGAAGACCCAGAGGATGCTGAG
CGGATTCTGCCCGCACAAGGTCTCAGCTGGGCAGTTTTCCAGCTTGCATG
TCCGAGACACCAAAATCGAGGTGGCCCAGTTTGTAAAGGACCTGCTCTTA
CATTTAAAGAAACTTTTTCGCGAGGGACGGTTCAAC

IL-13 amino acid:
SEQ ID NO: 64

GPVPPSTALRELIEELVNITQNQKAPLCNGSMVWSINLTAGMYCAALESL
INVSGCSAIEKTQRMLSGFCPHKVSAGQFSSLHVRDTKIEVAQFVKDLLL
HLKKLFREGRFN

PEKDEL nucleotide:
SEQ ID NO: 65

CCCGAGGGCGGCAGCCTGGCCGCGCTGACCGCGCACCAGGCTTGCCACCT
GCCGCTGGAGACTTTCACCCGTCATCGCCAGCCGCGCGGCTGGGAACAAC
TGGAGCAGTGCGGCTATCCGGTGCAGCGGCTGGTCGCCCTCTACCTGGCG
GCGCGGCTGTCGTGGAACCAGGTCGACCAGGTGATCCGCAACGCCCTGGC
CAGCCCCGGCAGCGGCGGCGACCTGGGCGAAGCGATCCGCGAGCAGCCGG
AGCAGGCCCGTCTGGCCCTGACCCTGGCCGCCGCCGAGAGCGAGCGCTTC
GTCCGGCAGGGCACCGGCAACGACGAGGCCGGCGCGGCCAACGCCGACGT
GGTGAGCCTGACCTGCCCGGTCGCCGCCGGTGAATGCGCGGGCCCGGCGG
ACAGCGGCGACGCCCTGCTGGAGCGCAACTATCCCACTGGCGCGGAGTTC
CTCGGCGACGGCGGCGACGTCAGCTTCAGCACCCGCGGCACGCAGAACTG
GACGGTGGAGCGGCTGCTCCAGGCGCACCGCCAACTGGAGGAGGGAGGCT
ATGTGTTCGTCGGCTACCACGGCACCTTCCTCGAAGCGGCGCAAAGCATC
GTCTTCGGCGGGGTGCGCGCGCGCAGCCAGGACCTCGACGCGATCTGGCG
CGGTTTCTATATCGCCGGCGATCCGGCGCTGGCCTACGGCTACGCCCAGG
ACCAGGAACCCGACGCACGCGGCCGGATCCGCAACGGTGCCCTGCTGCGG
GTCTATGTGCCGCGCTCGAGCCTGCCGGGCTTCTACCGCACCAGCCTGAC
CCTGGCCGCGCCGGAGGCGGCGGGCGAGGTCGAACGGCTGATCGGCCATC
CGCTGCCGCTGCGCCTGGACGCCATCACCGGCCCCGAGGAGGAAGGCGGG
CGCCTGGAGACCATTCTCGGCTGGCCGCTGGCCGAGCGCACCGTGGTGAT
TCCCTCGGCGATCCCCACCGACCCGCGCAACGTCGGCGGCGACCTCGACC
CGTCCAGCATCCCCGACAAGGAACAGGCGATCAGCGCCCTGCCGGACTAC
GCCAGCCAGCCCGGCAAACCGCCGAAGGACGAGCTA

PE KDEL amino acid:
SEQ ID NO: 66

PEGGSLAALTAHQACHLPLETFTRHRQPRGWEQLEQCGYPVQRLVALYLA
ARLSWNQVDQVIRNALASPGSGGDLGEAIREQPEQARLALTLAAAESERF
VRQGTGNDEAGAANADVVSLTCPVAAGECAGPADSGDALLERNYPTGAEF
LGDGGDVSFSTRGTQNWTVERLLQAHRQLEERGYVFVGYHGTFLEAAQSI
VFGGVRARSQDLDAIWRGFYIAGDPALAYGYAQDQEPDARGRIRNGALLR
VYVPRSSLPGFYRTSLTLAAPEAAGEVERLIGHPLPLRLDAITGPEEEGG
RLETILGWPLAERTVVIPSAIPTDPRNVGGDLDPSSIPDKEQAISALPDY
ASQPGKPPKDEL

Deimmunized PEKDEL nucleotide:
SEQ ID NO: 67

CCCGAGGGCGGCAGCCTGGCCGCGCTGACCGCGCACCAGGCTTGCCACCT
GCCGCTGGAGACTTTCACCCGTCATCGCCAGCCGCGCGGCTGGGAACAAC
TGGAGCAGTGCGGCTATCCGGTGCAGCGGCTGGTCGCCCTCTACCTGGCG
GCGCGGCTGTCGTGGAACCAGGTCGACCAGGTGATCGCCAACGCCCTGGC
CAGCCCCGGCAGCGGCGGCGACCTGGGCGAAGCGATCCGCGAGTCGCCGG
AGCAGGCCCGTCTGGCCCTGACCCTGGCCGCCGCCGAGAGCGAGCGCTTC
GTCCGGCAGGGCACCGGCAACGACGAGGCCGGCGCGGCCAACGCCGACGT
GGTGAGCCTGACCTGCCCGGTCGCCGCCGGTGAATGCGCGGGCCCGGCGG
ACAGCGGCGACGCCCTGCTGGAGCGCAACTATCCCACTGGCGCGGAGTTC
CTCGGCGACGGCGGCGACGTCAGCTTCAGCACCCGCGGCACGCAGAACTG
GACGGTGGAGCGGCTGCTCCAGGCGCACCGCCAACTGGAGGAGGGAGGCT
ATGTGTTCGTCGGCTACCACGGCACCTTCCTCGAAGCGGCGCAAAGCATC
GTCTTCGGCGGGGTGCGCGCGCGCAGCCAGGACCTCGACGCGATCTGGGC
CGGTTTCTATATCGCCGGCGATCCGGCGCTGGCCTACGGCTACGCCCAGG
ACCAGGAACCCGACGCAGCCGGCCGGATCCGCAACGGTGCCCTGCTGCGG
GTCTATGTGCCGCGCTCGAGCCTGCCGGGCTTCTACGCCACCAGCCTGAC
CCTGGCCGCGCCGGAGGCGGCGGGCGAGGTCGAACGGCTGATCGGCCATC
CGCTGCCGCTGCGCCTGGACGCCATCACCGGCCCCGAGGAGTCAGGCGGG
CGCCTGGAGACCATTCTCGGCTGGCCGCTGGCCGAGCGCACCGTGGTGAT
TCCCTCGGCGATCCCCACCGACCCGCGCAACGTCGGCGGCGACCTCGACC
CGTCCAGCATCCCCGACTCGGAACAGGCGATCAGCGCCCTGCCGGACTAC
GCCAGCCAGCCCGGCAAACCGCCGAAGGACGAGCTAGAAGCTTCCGGAGG
TCCCGAG

-continued

Deimmunized PEKDEL amino acid:
SEQ ID NO: 68
PEGGSLAALTAHQACHLPLETFTRHRQPRGWEQLEQCGYPVQRLVALYLA

ARLSWNQVDQVIANALASPGSGGDLGEAIRESPEQARLALTLAAAESERF

VRQGTGNDEAGAANADVVSLTCPVAAGECAGPADSGDALLERNYPTGAEF

LGDGGDVSFSTRGTQNWTVERLLQAHRQLEEGGYVFVGYHGTFLEAAQSI

VFGGVRARSQDLDAIWAGFYIAGDPALAYGYAQDQEPDAAGRIRNGALLR

VYVPRSSLPGFYATSLTLAAPEAAGEVERLIGHPLPLRLDAITGPEESGG

RLETILGWPLAERTVVIPSAIPTDPRNVGGDLDPSSIPDSEQAISALPDY

ASQPGKPPKDELEASGGPE

ARL linker:
SEQ ID NO: 69
GSTSGSGKPGSGEGSTKG

REFERENCES

Bidlingmaier, S., Zhu, X. and Liu, B. (2008) The utility and limitations of glycosylated human CD133 epitopes in defining cancer stem cells. J Mol Med 86, 1025-32.

Kemper, K., Sprick, M. R., de Bree, M., Scopelliti, A., Vermeulen, L., Hoek, M., Zeilstra, J., Pals, S. T., Mehmet, H., Stassi, G. and Medema, J. P. The AC133 epitope, but not the CD133 protein, is lost upon cancer stem cell differentiation. Cancer Res 70, 719-29.

Lehle, L. and Tanner, W. (1976) The specific site of tunicamycin inhibition in the formation of dolichol-bound N-acetylglucosamine derivatives. FEBS Lett 72, 167-70.

Shmelkov, S. V., St Clair, R., Lyden, D. and Rafii, S. (2005) AC133/CD133/Prominin-1. Int J Biochem Cell Biol 37, 715-9.

Tkacz, J. S. and Lampen, O. (1975) Tunicamycin inhibition of polyisoprenyl N-acetylglucosaminyl pyrophosphate formation in calf-liver microsomes. Biochem Biophys Res Commun 65, 248-57.

Weigmann, A., Corbeil, D., Hellwig, A. and Huttner, W. B. (1997) Prominin, a novel microvilli-specific polytopic membrane protein of the apical surface of epithelial cells, is targeted to plasmalemmal protrusions of non-epithelial cells. Proc Natl Acad Sci USA 94, 12425-30.

Yin, A. H., Miraglia, S., Zanjani, E. D., Almeida-Porada, G., Ogawa, M., Leary, A. G., Olweus, J., Kearney, J. and Buck, D. W. (1997) AC133, a novel marker for human hematopoietic stem and progenitor cells. Blood 90, 5002-12.

---

What is claimed is:

1. An isolated polynucleotide comprising a nucleotide sequence that encodes the amino acid sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, or SEQ ID NO:58.

2. The isolated polynucleotide of claim 1 wherein the isolated polynucleotide comprises a nucleotide sequence that encodes the amino acid sequence of SEQ ID NO:58.

3. The isolated polynucleotide of claim 2 wherein the isolated polynucleotide comprises the nucleic acid sequence of SEQ ID NO:57.

* * * * *

SEQUENCE LISTING

```
<160> NUMBER OF SEQ ID NOS: 74

<210> SEQ ID NO 1
<211> LENGTH: 865
<212> TYPE: PRT
<213> ORGANISM: Homo sapiens

<400> SEQUENCE: 1

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Lys
            35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
```

```
            195                 200                 205
Pro Glu Gln Ile Lys Tyr Ile Leu Ala Gln Tyr Asn Thr Thr Lys Asp
210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
            275                 280                 285

Ser Ser Leu Thr Ser Val Lys Thr Ser Leu Arg Ser Ser Leu Asn Asp
290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
610                 615                 620
```

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
            645                 650                 655

Lys Ala Asn Ser Leu Pro Pro Gly Asn Leu Arg Asn Ser Leu Lys Arg
        660                 665                 670

Asp Ala Gln Thr Ile Lys Thr Ile His Gln Gln Arg Val Leu Pro Ile
    675                 680                 685

Glu Gln Ser Leu Ser Thr Leu Tyr Gln Ser Val Lys Ile Leu Gln Arg
690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
            725                 730                 735

Glu Glu Thr Lys Lys Tyr Gly Arg Thr Ile Ile Gly Tyr Phe Glu His
        740                 745                 750

Tyr Leu Gln Trp Ile Glu Phe Ser Ile Ser Glu Lys Val Ala Ser Cys
    755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
            805                 810                 815

Lys Tyr Tyr Arg Arg Met Asp Ser Glu Asp Val Tyr Asp Asp Val Glu
        820                 825                 830

Thr Ile Pro Met Lys Asn Met Glu Asn Gly Asn Asn Gly Tyr His Lys
    835                 840                 845

Asp His Val Tyr Gly Ile His Asn Pro Val Met Thr Ser Pro Ser Gln
    850                 855                 860

His
865

<210> SEQ ID NO 2
<211> LENGTH: 355
<212> TYPE: PRT
<213> ORGANISM: Homo sapiens

<400> SEQUENCE: 2

Asn His Gln Val Arg Thr Arg Ile Lys Arg Ser Arg Lys Leu Ala Asp
1               5                   10                  15

Ser Asn Phe Lys Asp Leu Arg Thr Leu Leu Asn Glu Thr Pro Glu Gln
            20                  25                  30

Ile Lys Tyr Ile Leu Ala Gln Tyr Asn Thr Thr Lys Asp Lys Ala Phe
        35                  40                  45

Thr Asp Leu Asn Ser Ile Asn Ser Val Leu Gly Gly Gly Ile Leu Asp
    50                  55                  60

Arg Leu Arg Pro Asn Ile Ile Pro Val Leu Asp Glu Ile Lys Ser Met
65                  70                  75                  80

Ala Thr Ala Ile Lys Glu Thr Lys Glu Ala Leu Glu Asn Met Asn Ser
                85                  90                  95

Thr Leu Lys Ser Leu His Gln Gln Ser Thr Gln Leu Ser Ser Ser Leu
            100                 105                 110

Thr Ser Val Lys Thr Ser Leu Arg Ser Ser Leu Asn Asp Pro Leu Cys

```
            115                 120                 125
Leu Val His Pro Ser Ser Glu Thr Cys Asn Ser Ile Arg Leu Ser Leu
        130                 135                 140

Ser Gln Leu Asn Ser Asn Pro Glu Leu Arg Gln Leu Pro Pro Val Asp
145                 150                 155                 160

Ala Glu Leu Asp Asn Val Asn Val Leu Arg Thr Asp Leu Asp Gly
                165                 170                 175

Leu Val Gln Gln Gly Tyr Gln Ser Leu Asn Asp Ile Pro Asp Arg Val
            180                 185                 190

Gln Arg Gln Thr Thr Thr Val Val Ala Ala Ala Gly Arg Lys Asn Leu
        195                 200                 205

Gln Asp Phe Ala Ala Cys Gly Ile Asp Arg Met Asn Tyr Asp Ser Tyr
        210                 215                 220

Leu Ala Gln Thr Gly Lys Ser Pro Ala Gly Val Asn Leu Leu Ser Phe
225                 230                 235                 240

Ala Tyr Asp Leu Glu Ala Lys Ala Asn Ser Leu Pro Pro Gly Asn Leu
                245                 250                 255

Arg Asn Ser Leu Lys Arg Asp Ala Gln Thr Ile Lys Thr Ile His Gln
            260                 265                 270

Gln Arg Val Leu Pro Ile Glu Gln Ser Leu Ser Thr Leu Tyr Gln Ser
        275                 280                 285

Val Lys Ile Leu Gln Arg Thr Gly Asn Gly Leu Leu Glu Arg Val Thr
290                 295                 300

Arg Ile Leu Ala Ser Leu Asp Phe Ala Gln Asn Phe Ile Thr Asn Asn
305                 310                 315                 320

Thr Ser Ser Val Ile Ile Glu Glu Thr Lys Lys Tyr Gly Arg Thr Ile
                325                 330                 335

Ile Gly Tyr Phe Glu His Tyr Leu Gln Trp Ile Glu Phe Ser Ile Ser
            340                 345                 350

Glu Lys Val
        355

<210> SEQ ID NO 3
<211> LENGTH: 40
<212> TYPE: DNA
<213> ORGANISM: artificial
<220> FEATURE:
<223> OTHER INFORMATION: synthetic oligonucleotide primer

<400> SEQUENCE: 3
gggcccaggc ggccgagctc gayatccagc tgactcagcc                40

<210> SEQ ID NO 4
<211> LENGTH: 40
<212> TYPE: DNA
<213> ORGANISM: artificial
<220> FEATURE:
<223> OTHER INFORMATION: synthetic oligonucleotide primer

<400> SEQUENCE: 4
gggcccaggc ggccgagctc gayattgttc tcwcccagtc                40

<210> SEQ ID NO 5
<211> LENGTH: 40
<212> TYPE: DNA
<213> ORGANISM: artificial
<220> FEATURE:
<223> OTHER INFORMATION: synthetic oligonucleotide primer
```

```
<400> SEQUENCE: 5
gggcccaggc ggccgagctc gayattgtgm tmactcagtc                              40

<210> SEQ ID NO 6
<211> LENGTH: 40
<212> TYPE: DNA
<213> ORGANISM: artificial
<220> FEATURE:
<223> OTHER INFORMATION: synthetic oligonucleotide primer

<400> SEQUENCE: 6
gggcccaggc ggccgagctc gayattgtgy tracacagtc                              40

<210> SEQ ID NO 7
<211> LENGTH: 40
<212> TYPE: DNA
<213> ORGANISM: artificial
<220> FEATURE:
<223> OTHER INFORMATION: synthetic oligonucleotide primer

<400> SEQUENCE: 7
gggcccaggc ggccgagctc gayattgtra tgacmcagtc                              40

<210> SEQ ID NO 8
<211> LENGTH: 40
<212> TYPE: DNA
<213> ORGANISM: artificial
<220> FEATURE:
<223> OTHER INFORMATION: synthetic oligonucleotide primer

<400> SEQUENCE: 8
gggcccaggc ggccgagctc gayattmaga tramccagtc                              40

<210> SEQ ID NO 9
<211> LENGTH: 40
<212> TYPE: DNA
<213> ORGANISM: artificial
<220> FEATURE:
<223> OTHER INFORMATION: synthetic oligonucleotide primer

<400> SEQUENCE: 9
gggcccaggc ggccgagctc gayattcaga tgaydcagtc                              40

<210> SEQ ID NO 10
<211> LENGTH: 40
<212> TYPE: DNA
<213> ORGANISM: artificial
<220> FEATURE:
<223> OTHER INFORMATION: synthetic oligonucleotide primer

<400> SEQUENCE: 10
gggcccaggc ggccgagctc gayatycaga tgacacagac                              40

<210> SEQ ID NO 11
<211> LENGTH: 40
<212> TYPE: DNA
<213> ORGANISM: artificial
<220> FEATURE:
<223> OTHER INFORMATION: synthetic oligonucleotide primer

<400> SEQUENCE: 11
gggcccaggc ggccgagctc gayattgttc tcawccagtc                              40

<210> SEQ ID NO 12
<211> LENGTH: 40
```

```
<212> TYPE: DNA
<213> ORGANISM: artificial
<220> FEATURE:
<223> OTHER INFORMATION: synthetic oligonucleotide primer

<400> SEQUENCE: 12
gggcccaggc ggccgagctc gayattgwgc tsacccaatc                              40

<210> SEQ ID NO 13
<211> LENGTH: 40
<212> TYPE: DNA
<213> ORGANISM: artificial
<220> FEATURE:
<223> OTHER INFORMATION: synthetic oligonucleotide primer

<400> SEQUENCE: 13
gggcccaggc ggccgagctc gayattstra tgacccartc                              40

<210> SEQ ID NO 14
<211> LENGTH: 40
<212> TYPE: DNA
<213> ORGANISM: artificial
<220> FEATURE:
<223> OTHER INFORMATION: synthetic oligonucleotide primer

<400> SEQUENCE: 14
gggcccaggc ggccgagctc gayrttktga tgacccarac                              40

<210> SEQ ID NO 15
<211> LENGTH: 40
<212> TYPE: DNA
<213> ORGANISM: artificial
<220> FEATURE:
<223> OTHER INFORMATION: synthetic oligonucleotide primer

<400> SEQUENCE: 15
gggcccaggc ggccgagctc gayattgtga tgacbcagkc                              40

<210> SEQ ID NO 16
<211> LENGTH: 40
<212> TYPE: DNA
<213> ORGANISM: artificial
<220> FEATURE:
<223> OTHER INFORMATION: synthetic oligonucleotide primer

<400> SEQUENCE: 16
gggcccaggc ggccgagctc gayattgtga taacycagga                              40

<210> SEQ ID NO 17
<211> LENGTH: 40
<212> TYPE: DNA
<213> ORGANISM: artificial
<220> FEATURE:
<223> OTHER INFORMATION: synthetic oligonucleotide primer

<400> SEQUENCE: 17
gggcccaggc ggccgagctc gayattgtga tgacccagwt                              40

<210> SEQ ID NO 18
<211> LENGTH: 40
<212> TYPE: DNA
<213> ORGANISM: artificial
<220> FEATURE:
<223> OTHER INFORMATION: synthetic oligonucleotide primer

<400> SEQUENCE: 18
```

```
gggcccaggc ggccgagctc gayattgtga tgacacaacc                     40
```

<210> SEQ ID NO 19
<211> LENGTH: 40
<212> TYPE: DNA
<213> ORGANISM: artificial
<220> FEATURE:
<223> OTHER INFORMATION: synthetic oligonucleotide primer

<400> SEQUENCE: 19

```
gggcccaggc ggccgagctc gayattttgc tgactcagtc                     40
```

<210> SEQ ID NO 20
<211> LENGTH: 75
<212> TYPE: DNA
<213> ORGANISM: artificial
<220> FEATURE:
<223> OTHER INFORMATION: synthetic oligonucleotide primer

<400> SEQUENCE: 20

```
ggaagatcta gaggaaccac ccccaccacc gcccgagcca ccgccaccag aggatttkat    60
ttccagyttg gtccc                                                    75
```

<210> SEQ ID NO 21
<211> LENGTH: 75
<212> TYPE: DNA
<213> ORGANISM: artificial
<220> FEATURE:
<223> OTHER INFORMATION: synthetic oligonucleotide primer

<400> SEQUENCE: 21

```
ggaagatcta gaggaaccac ccccaccacc gcccgagcca ccgccaccag aggattttat    60
ttccaacttt gtccc                                                    75
```

<210> SEQ ID NO 22
<211> LENGTH: 75
<212> TYPE: DNA
<213> ORGANISM: artificial
<220> FEATURE:
<223> OTHER INFORMATION: synthetic oligonucleotide primer

<400> SEQUENCE: 22

```
ggaagatcta gaggaaccac ccccaccacc gcccgagcca ccgccaccag aggatttcag    60
ctccagcttg gtccc                                                    75
```

<210> SEQ ID NO 23
<211> LENGTH: 44
<212> TYPE: DNA
<213> ORGANISM: artificial
<220> FEATURE:
<223> OTHER INFORMATION: synthetic oligonucleotide primer

<400> SEQUENCE: 23

```
ggtggttcct ctagatcttc cctcgaggtr magcttcagg agtc                    44
```

<210> SEQ ID NO 24
<211> LENGTH: 44
<212> TYPE: DNA
<213> ORGANISM: artificial
<220> FEATURE:
<223> OTHER INFORMATION: synthetic oligonucleotide primer

<400> SEQUENCE: 24

```
ggtggttcct ctagatcttc cctcgaggtb cagctbcagc agtc                    44
```

<210> SEQ ID NO 25
<211> LENGTH: 44
<212> TYPE: DNA
<213> ORGANISM: artificial
<220> FEATURE:
<223> OTHER INFORMATION: synthetic oligonucleotide primer

<400> SEQUENCE: 25
ggtggttcct ctagatcttc cctcgaggtg cagctgaags astc                            44

<210> SEQ ID NO 26
<211> LENGTH: 44
<212> TYPE: DNA
<213> ORGANISM: artificial
<220> FEATURE:
<223> OTHER INFORMATION: synthetic oligonucleotide primer

<400> SEQUENCE: 26
ggtggttcct ctagatcttc cctcgaggtc carctgcaac artc                            44

<210> SEQ ID NO 27
<211> LENGTH: 44
<212> TYPE: DNA
<213> ORGANISM: artificial
<220> FEATURE:
<223> OTHER INFORMATION: synthetic oligonucleotide primer

<400> SEQUENCE: 27
ggtggttcct ctagatcttc cctcgaggty cagctbcagc artc                            44

<210> SEQ ID NO 28
<211> LENGTH: 44
<212> TYPE: DNA
<213> ORGANISM: artificial
<220> FEATURE:
<223> OTHER INFORMATION: synthetic oligonucleotide primer

<400> SEQUENCE: 28
ggtggttcct ctagatcttc cctcgaggty carctgcagc agtc                            44

<210> SEQ ID NO 29
<211> LENGTH: 44
<212> TYPE: DNA
<213> ORGANISM: artificial
<220> FEATURE:
<223> OTHER INFORMATION: synthetic oligonucleotide primer

<400> SEQUENCE: 29
ggtggttcct ctagatcttc cctcgaggtc cacgtgaagc agtc                            44

<210> SEQ ID NO 30
<211> LENGTH: 44
<212> TYPE: DNA
<213> ORGANISM: artificial
<220> FEATURE:
<223> OTHER INFORMATION: synthetic oligonucleotide primer

<400> SEQUENCE: 30
ggtggttcct ctagatcttc cctcgaggtg aasstggtgg aatc                            44

<210> SEQ ID NO 31
<211> LENGTH: 44
<212> TYPE: DNA
<213> ORGANISM: artificial
<220> FEATURE:

<223> OTHER INFORMATION: synthetic oligonucleotide primer

<400> SEQUENCE: 31
ggtggttcct ctagatcttc cctcgaggtg awgytggtgg agtc          44

<210> SEQ ID NO 32
<211> LENGTH: 44
<212> TYPE: DNA
<213> ORGANISM: artificial
<220> FEATURE:
<223> OTHER INFORMATION: synthetic oligonucleotide primer

<400> SEQUENCE: 32
ggtggttcct ctagatcttc cctcgaggtg cagskggtgg agtc          44

<210> SEQ ID NO 33
<211> LENGTH: 44
<212> TYPE: DNA
<213> ORGANISM: artificial
<220> FEATURE:
<223> OTHER INFORMATION: synthetic oligonucleotide primer

<400> SEQUENCE: 33
ggtggttcct ctagatcttc cctcgaggtg camctggtgg agtc          44

<210> SEQ ID NO 34
<211> LENGTH: 44
<212> TYPE: DNA
<213> ORGANISM: artificial
<220> FEATURE:
<223> OTHER INFORMATION: synthetic oligonucleotide primer

<400> SEQUENCE: 34
ggtggttcct ctagatcttc cctcgaggtg aagctgatgg artc          44

<210> SEQ ID NO 35
<211> LENGTH: 44
<212> TYPE: DNA
<213> ORGANISM: artificial
<220> FEATURE:
<223> OTHER INFORMATION: synthetic oligonucleotide primer

<400> SEQUENCE: 35
ggtggttcct ctagatcttc cctcgaggtg carcttgttg agtc          44

<210> SEQ ID NO 36
<211> LENGTH: 44
<212> TYPE: DNA
<213> ORGANISM: artificial
<220> FEATURE:
<223> OTHER INFORMATION: synthetic oligonucleotide primer

<400> SEQUENCE: 36
ggtggttcct ctagatcttc cctcgaggtr aagcttctcg agtc          44

<210> SEQ ID NO 37
<211> LENGTH: 44
<212> TYPE: DNA
<213> ORGANISM: artificial
<220> FEATURE:
<223> OTHER INFORMATION: synthetic oligonucleotide primer

<400> SEQUENCE: 37
ggtggttcct ctagatcttc cctcgaggtg aarsttgagg agtc          44

```
<210> SEQ ID NO 38
<211> LENGTH: 46
<212> TYPE: DNA
<213> ORGANISM: artificial
<220> FEATURE:
<223> OTHER INFORMATION: synthetic oligonucleotide primer

<400> SEQUENCE: 38
ggtggttcct ctagatcttc cctcgaggtt actctraaag wgtstg                    46

<210> SEQ ID NO 39
<211> LENGTH: 44
<212> TYPE: DNA
<213> ORGANISM: artificial
<220> FEATURE:
<223> OTHER INFORMATION: synthetic oligonucleotide primer

<400> SEQUENCE: 39
ggtggttcct ctagatcttc cctcgaggtc caactvcagc arcc                      44

<210> SEQ ID NO 40
<211> LENGTH: 44
<212> TYPE: DNA
<213> ORGANISM: artificial
<220> FEATURE:
<223> OTHER INFORMATION: synthetic oligonucleotide primer

<400> SEQUENCE: 40
ggtggttcct ctagatcttc cctcgaggtg aacttggaag tgtc                      44

<210> SEQ ID NO 41
<211> LENGTH: 44
<212> TYPE: DNA
<213> ORGANISM: artificial
<220> FEATURE:
<223> OTHER INFORMATION: synthetic oligonucleotide primer

<400> SEQUENCE: 41
ggtggttcct ctagatcttc cctcgaggtg aaggtcatcg agtc                      44

<210> SEQ ID NO 42
<211> LENGTH: 46
<212> TYPE: DNA
<213> ORGANISM: artificial
<220> FEATURE:
<223> OTHER INFORMATION: synthetic oligonucleotide primer

<400> SEQUENCE: 42
cctggccggc ctggccacta gtgacagatg gggstgtygt tttggc                    46

<210> SEQ ID NO 43
<211> LENGTH: 41
<212> TYPE: DNA
<213> ORGANISM: artificial
<220> FEATURE:
<223> OTHER INFORMATION: synthetic oligonucleotide primer

<400> SEQUENCE: 43
gaggaggagg aggaggaggc ggggcccagg cggccgagct c                         41

<210> SEQ ID NO 44
<211> LENGTH: 41
<212> TYPE: DNA
<213> ORGANISM: artificial
<220> FEATURE:
<223> OTHER INFORMATION: synthetic oligonucleotide primer
```

```
<400> SEQUENCE: 44
gaggaggagg aggaggagcc tggccggcct ggccactagt g                           41

<210> SEQ ID NO 45
<211> LENGTH: 22
<212> TYPE: DNA
<213> ORGANISM: artificial
<220> FEATURE:
<223> OTHER INFORMATION: synthetic oligonucleotide primer

<400> SEQUENCE: 45
aagacagcta tcgcgattgc ag                                                22

<210> SEQ ID NO 46
<211> LENGTH: 24
<212> TYPE: DNA
<213> ORGANISM: artificial
<220> FEATURE:
<223> OTHER INFORMATION: synthetic oligonucleotide primer

<400> SEQUENCE: 46
gcccccttat tagcgtttgc catc                                              24

<210> SEQ ID NO 47
<211> LENGTH: 260
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(260)
<223> OTHER INFORMATION: variable region of the heavy chain

<400> SEQUENCE: 47

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Gly Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Gly Ser Ser Arg
            115                 120                 125

Ser Ser Leu Glu Val Lys Leu Val Glu Ser Gly Pro Glu Leu Lys Lys
    130                 135                 140

Pro Gly Glu Thr Val Lys Ile Ser Cys Lys Ala Ser Gly Tyr Thr Phe
```

```
                        145                 150                 155                 160
Thr Asp Tyr Ser Met His Trp Val Asn Gln Ala Pro Gly Lys Gly Leu
                    165                 170                 175

Lys Trp Met Gly Trp Ile Asn Thr Glu Thr Gly Pro Ser Tyr Ala
                180                 185                 190

Asp Asp Phe Lys Gly Arg Phe Ala Phe Ser Leu Glu Thr Ser Ala Ser
                195                 200                 205

Thr Ala Tyr Leu Gln Ile Asn Asn Leu Lys Asn Glu Asp Thr Ala Thr
            210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Pro Pro Ser Val
                245                 250                 255

Thr Ser Gly Gln
            260

<210> SEQ ID NO 48
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 48

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
                20                  25                  30

Ser Ser Val Ser Tyr Met Tyr Trp Tyr Gln Gln Lys Pro Gly Ser Ser
                35                  40                  45

Pro Lys Pro Trp Ile Tyr Arg Thr Ser Asn Leu Ala Ser Gly Val Pro
            50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
                100                 105                 110

Ser Ser Gly Gly Gly Gly Ser Gly Gly Gly Gly Gly Ser Ser Arg
                115                 120                 125

Ser Ser Leu Glu Val Lys Leu Val Glu Ser Gly Pro Glu Leu Lys Lys
            130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175
```

```
Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
        210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Pro Pro Ser Val
            245                 250                 255

Thr Ser Gly Gln Ala Gly Gln
            260

<210> SEQ ID NO 49
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 49

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Ser Gly Ser Ser Arg
        115                 120                 125

Ser Ser Pro Glu Val Met Leu Val Glu Ser Gly Pro Glu Leu Lys Lys
    130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205
```

Thr Ala Tyr Leu Gln Ile Asn Asn Leu Lys Asn Glu Asp Thr Ala Thr
                210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Pro Pro Ser Val
                245                 250                 255

Thr Ser Gly Gln Ala Gly Gln
            260

<210> SEQ ID NO 50
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 50

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
                20                  25                  30

Ser Ser Val Ser Tyr Met Tyr Trp Tyr Gln Gln Lys Pro Gly Gln Pro
            35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln Gln Tyr
                85                  90                  95

His Ser Tyr Pro Pro Thr Phe Gly Ala Gly Thr Lys Leu Glu Ile Lys
            100                 105                 110

Ser Ser Gly Gly Gly Gly Ser Gly Gly Gly Gly Gly Ser Ser Arg
    115                 120                 125

Ser Ser Leu Glu Val Lys Leu Val Glu Ser Gly Pro Glu Leu Lys Lys
130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Tyr Gly Asp Tyr Phe Asp Tyr Trp Gly Gln
225                 230                 235                 240

```
225                 230                 235                 240

Gly Thr Thr Leu Thr Val Ser Ser Ala Lys Thr Thr Pro Pro Ser Val
                245                 250                 255

Thr Ser Gly Gln Ala Gly Gln
            260

<210> SEQ ID NO 51
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 51

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Gly Ser Ser Arg
        115                 120                 125

Ser Ser Leu Glu Val His Leu Val Glu Ser Gly Pro Glu Leu Lys Lys
130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Pro Pro Ser Val
                245                 250                 255
```

Thr Ser Gly Gln Ala Gly Gln
            260

<210> SEQ ID NO 52
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 52

Ala Gln Ala Ala Glu Leu Asp Ile Val Leu Ser Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Lys Pro Gly Ser Pro
        35                  40                  45

Pro Lys Pro Trp Ile Tyr Arg Thr Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Gly Ser Ser Arg
        115                 120                 125

Ser Ser Leu Glu Val Lys Leu Val Glu Ser Gly Pro Glu Leu Lys Lys
    130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Cys Gly Asp Tyr Phe Asp Tyr Trp Gly Gln
225                 230                 235                 240

Gly Thr Thr Leu Thr Val Ser Ser Ala Lys Thr Thr Pro Pro Ser Val
                245                 250                 255

Thr Ser Gly Gln Ala Gly Gln
            260

<210> SEQ ID NO 53

```
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 53

Ala Gln Ala Ala Glu Leu Asp Ile Val Leu Ser Gln Ser Pro Ala Ile
 1               5                  10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Thr Ser Asn Leu Ala Ser Gly Val Pro
 50                  55                  60

Ala Arg Phe Ser Gly Ser Gly Ser Gly Thr Ser Tyr Ser Leu Thr Ile
 65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Ser Ser Arg
        115                 120                 125

Ser Ser Leu Glu Val Lys Leu Val Glu Ser Gly Pro Glu Leu Lys Lys
    130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Pro Pro Ser Val
                245                 250                 255

Thr Ser Gly Gln Ala Gly Gln
            260

<210> SEQ ID NO 54
<211> LENGTH: 263
<212> TYPE: PRT
<213> ORGANISM: artificial
<220> FEATURE:
<223> OTHER INFORMATION: single-chain variable-fragment (scFv) of a
```

```
                        monoclonal antibody clone
<220> FEATURE:
<221> NAME/KEY: MISC_FEATURE
<222> LOCATION: (1)..(112)
<223> OTHER INFORMATION: variable region of the light chain
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 54

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Asp Gly Gly Ser Gly Gly Gly Gly Gly Ser Ser Ser Arg
        115                 120                 125

Ser Ser Leu Glu Val Lys Leu Val Glu Ser Gly Pro Glu Leu Lys Lys
    130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Gly Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Ala Pro Ser Val
                245                 250                 255

Thr Ser Gly Gln Ala Gly Gln
            260

<210> SEQ ID NO 55
<211> LENGTH: 263
<212> TYPE: PRT
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: MISC_FEATURE
<222> LOCATION: (1)..(112)
<223> OTHER INFORMATION: variable region of the light chain
```

```
<220> FEATURE:
<221> NAME/KEY: MISC_FEATURE
<222> LOCATION: (113)..(130)
<223> OTHER INFORMATION: linker
<220> FEATURE:
<221> NAME/KEY: MISC_FEATURE
<222> LOCATION: (131)..(263)
<223> OTHER INFORMATION: variable region of the heavy chain

<400> SEQUENCE: 55

Ala Gln Ala Ala Glu Leu Asp Ile Val Leu Thr Gln Ser Pro Ala Ile
1               5                   10                  15

Met Ser Ala Ser Pro Gly Glu Lys Val Thr Ile Ser Cys Ser Ala Ser
            20                  25                  30

Ser Ser Val Ser Tyr Met Tyr Trp Tyr Gln Gln Lys Pro Gly Ser Ser
        35                  40                  45

Pro Lys Pro Trp Ile Tyr Arg Pro Ser Asn Leu Ala Ser Gly Val Pro
    50                  55                  60

Ala Arg Phe Ser Gly Ser Gly Ser Gly Thr Ser Tyr Ser Leu Thr Ile
65                  70                  75                  80

Ser Ser Met Glu Ala Glu Asp Ala Ala Thr Tyr Tyr Cys Gln Gln Tyr
                85                  90                  95

His Ser Tyr Pro Pro Thr Phe Gly Ala Gly Thr Lys Leu Glu Leu Lys
            100                 105                 110

Ser Ser Gly Gly Gly Gly Ser Gly Gly Gly Gly Gly Ser Ser Arg
        115                 120                 125

Ser Ser Leu Glu Val Gln Leu Val Glu Ser Gly Pro Glu Leu Lys Lys
    130                 135                 140

Pro Gly Glu Thr Val Lys Ile Ser Cys Lys Ala Ser Gly Tyr Thr Phe
145                 150                 155                 160

Thr Asp Tyr Ser Met His Trp Val Asn Gln Ala Pro Lys Gly Leu
                165                 170                 175

Lys Trp Met Gly Trp Ile Asn Thr Glu Thr Gly Glu Pro Ser Tyr Ala
            180                 185                 190

Asp Asp Phe Lys Gly Arg Phe Ala Phe Ser Leu Glu Thr Ser Ala Ser
        195                 200                 205

Thr Ala Tyr Leu Gln Ile Asn Asn Leu Lys Asn Glu Asp Thr Ala Thr
    210                 215                 220

Tyr Phe Cys Ala Thr Asp Tyr Gly Asp Tyr Phe Asp Tyr Trp Gly Gln
225                 230                 235                 240

Gly Thr Thr Leu Thr Val Ser Ser Ala Lys Thr Thr Ala Pro Ser Val
                245                 250                 255

Thr Ser Gly Gln Ala Gly Gln
            260

<210> SEQ ID NO 56
<211> LENGTH: 846
<212> TYPE: DNA
<213> ORGANISM: artificial
<220> FEATURE:
<223> OTHER INFORMATION: single-chain variable-fragment (scFv) of a
      monoclonal antibody clone
<220> FEATURE:
<221> NAME/KEY: misc_feature
<222> LOCATION: (1)..(13)
<223> OTHER INFORMATION: SfiI restriction site
<220> FEATURE:
<221> NAME/KEY: misc_feature
<222> LOCATION: (337)..(390)
<223> OTHER INFORMATION: linker
<220> FEATURE:
```

<221> NAME/KEY: misc_feature
<222> LOCATION: (775)..(787)
<223> OTHER INFORMATION: SfiI restriction site
<220> FEATURE:
<221> NAME/KEY: misc_feature
<222> LOCATION: (790)..(807)
<223> OTHER INFORMATION: 6HIS tag
<220> FEATURE:
<221> NAME/KEY: misc_feature
<222> LOCATION: (814)..(843)
<223> OTHER INFORMATION: HA tag
<220> FEATURE:
<221> NAME/KEY: terminator
<222> LOCATION: (844)..(846)

<400> SEQUENCE: 56

```
ggcccaggcg gccgagctcg acattgttct ctcccagtct ccagcaatca tgtctgcatc      60
tccaggggag aaggtcacca tatcctgcag tgccagctca agtgtaagtt atatgtactg     120
gtaccagcag aaccaggatc ctcccccaaa ccctggattt atcgcacatc caacctggct     180
tctggagtcc ctgctcgctt cagtggcagt gggtctggga cctcttactc tctcacaatc     240
agcagcatgg aggctgaaga tgctgccact tattactgcc agcagtatca tagttaccca     300
cccacgttcg gtgctgggac caagctggag ctgaaatcct ctggtggcgg tggctcgggc     360
ggtggtgggg gtggttcctc tagatcttcc ctcgaggtga agctggtgga gtctggacct     420
gagctgaaga agcctggaga gacagtcaag atctcctgca aggcttctgg ttataccttc     480
acagactatt caatgcactg ggtgaatcag ctccaggaa agggtttaaa gtggatgggc      540
tggataaaca ctgagactgg tgagccatca tatgcagatg acttcaaggg acggtttgcc     600
ttctctttgg aaacctctgc cagcactgcc tatttgcaga tcaacaacct caaaaatgag     660
gacacggcta catatttctg tgctaccgat tacggggact actttgacta ctggggccaa     720
ggcaccactc tcacagtctc ctcagccaaa acgacacccc catctgtcac tagtggccag     780
gccggccagc accatcacca tcaccatggc gcatacccgt acgacgttcc ggactacgct     840
tcttag                                                                846
```

<210> SEQ ID NO 57
<211> LENGTH: 729
<212> TYPE: DNA
<213> ORGANISM: artificial
<220> FEATURE:
<223> OTHER INFORMATION: scFv polypeptide encoding sequence

<400> SEQUENCE: 57

```
atggacattg ttctctccca gtctccagca atcatgtctg catctccagg ggagaaggtc      60
accatatcct gcagtgccag ctcaagtgta agttatatgt actggtacca gcagaagcca    120
ggatcctccc ccaaaccctg gatttatcgc acatccaacc tggcttctgg agtccctgct    180
cgcttcagtg gcagtgggtc tgggacctct tactctctca atcagcag catggaggct      240
gaagatgctg ccacttatta ctgccagcag tatcatagtt acccacccac gttcggtgct    300
gggaccaagc tggagctgaa atcctctggt ggcggtggct cgggcggtgg tggggtggt    360
tcctctagat cttccctcga ggtgaagctg gtggagtctg gacctgagct gaagaagcct    420
ggagagacag tcaagatctc ctgcaaggct tctggttata ccttcacaga ctattcaatg    480
cactgggtga atcaggctcc aggaaagggt ttaaagtgga tgggctggat aaacactgag    540
actggtgagc catcatatgc agatgacttc aagggacggt ttgccttctc tttggaaacc    600
tctgccagca ctgcctattt gcagatcaac aacctcaaaa atgaggacac ggctacatat    660
```

```
ttctgtgcta ccgattacgg ggactacttt gactactggg gccaaggcac cactctcaca    720
gtctcctca                                                             729
```

<210> SEQ ID NO 58
<211> LENGTH: 243
<212> TYPE: PRT
<213> ORGANISM: artificial
<220> FEATURE:
<223> OTHER INFORMATION: scFv polypeptide

<400> SEQUENCE: 58

```
Met Asp Ile Val Leu Ser Gln Ser Pro Ala Ile Met Ser Ala Ser Pro
1               5                   10                  15

Gly Glu Lys Val Thr Ile Ser Cys Ser Ala Ser Ser Val Ser Tyr
                20                  25                  30

Met Tyr Trp Tyr Gln Gln Lys Pro Gly Ser Ser Pro Lys Pro Trp Ile
            35                  40                  45

Tyr Arg Thr Ser Asn Leu Ala Ser Gly Val Pro Ala Arg Phe Ser Gly
50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys Gln Gln Tyr His Ser Tyr Pro Pro
                85                  90                  95

Thr Phe Gly Ala Gly Thr Lys Leu Glu Leu Lys Ser Ser Gly Gly Gly
            100                 105                 110

Gly Ser Gly Gly Gly Gly Gly Ser Ser Arg Ser Ser Leu Glu Val
        115                 120                 125

Lys Leu Val Glu Ser Gly Pro Glu Leu Lys Lys Pro Gly Glu Thr Val
130                 135                 140

Lys Ile Ser Cys Lys Ala Ser Gly Tyr Thr Phe Thr Asp Tyr Ser Met
145                 150                 155                 160

His Trp Val Asn Gln Ala Pro Gly Lys Gly Leu Lys Trp Met Gly Trp
                165                 170                 175

Ile Asn Thr Glu Thr Gly Glu Pro Ser Tyr Ala Asp Asp Phe Lys Gly
            180                 185                 190

Arg Phe Ala Phe Ser Leu Glu Thr Ser Ala Ser Thr Ala Tyr Leu Gln
        195                 200                 205

Ile Asn Asn Leu Lys Asn Glu Asp Thr Ala Thr Tyr Phe Cys Ala Thr
210                 215                 220

Asp Tyr Gly Asp Tyr Phe Asp Tyr Trp Gly Gln Gly Thr Thr Leu Thr
225                 230                 235                 240

Val Ser Ser
```

<210> SEQ ID NO 59
<211> LENGTH: 159
<212> TYPE: DNA
<213> ORGANISM: Homo sapiens

<400> SEQUENCE: 59

```
aacagcgaca cgaatgtcc gctgagccac gacggttact gtctgcacga cggtgtttgt    60
atgtacatcg aagctctaga caaatacgct tgtaactgtg ttgttggtta catcggtgaa   120
cgctgtcagt accgcgacct gaaatggtgg gaactgcgc                          159
```

<210> SEQ ID NO 60
<211> LENGTH: 53
<212> TYPE: PRT

<213> ORGANISM: Homo sapiens

<400> SEQUENCE: 60

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 61
<211> LENGTH: 1170
<212> TYPE: DNA
<213> ORGANISM: Homo sapiens

<400> SEQUENCE: 61

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaaccgt tactgggacc aatcctgtat tcgctggggc taactatgcg     840
gcgtgggcag taaacgttgc gcaagttatc gatagcgaaa cagctgataa tttggaaaag     900
acaactgctg ctctttcgat acttcctggt atcggtagcg taatgggcat tgcagacggt     960
gccgttcacc acaatacaga agagatagtg cacaatcaa tagctttatc gtctttaatg    1020
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt                                     1170
```

<210> SEQ ID NO 62
<211> LENGTH: 390
<212> TYPE: PRT
<213> ORGANISM: Homo sapiens

<400> SEQUENCE: 62

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp

```
                    35                  40                  45
Asp Asp Trp Lys Gly Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe
385                 390

<210> SEQ ID NO 63
<211> LENGTH: 336
<212> TYPE: DNA
<213> ORGANISM: Homo sapiens

<400> SEQUENCE: 63
ggccctgtgc ctccctctac agccctcagg gagctcattg aggagctggt caacatcacc      60
cagaaccaga aggctccgct ctgcaatggc agcatggtat ggagcatcaa cctgacagct     120
```

-continued

```
ggcatgtact gtgcagccct ggaatccctg atcaacgtgt caggctgcag tgccatcgag      180
aagacccaga ggatgctgag cggattctgc ccgcacaagg tctcagctgg cagttttcc      240 agcttgcatg tccgagacac caaaatcgag gtggcccagt ttgtaaagga cctgctctta     300
catttaaaga aacttttcg cgagggacgg ttcaac                                 336
```

<210> SEQ ID NO 64
<211> LENGTH: 112
<212> TYPE: PRT
<213> ORGANISM: Homo sapiens

<400> SEQUENCE: 64

```
Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110
```

<210> SEQ ID NO 65
<211> LENGTH: 1086
<212> TYPE: DNA
<213> ORGANISM: Homo sapiens

<400> SEQUENCE: 65

```
cccgagggcg gcagcctggc cgcgctgacc gcgcaccagg cttgccacct gccgctggag      60
actttcaccc gtcatcgcca gccgcgcggc tgggaacaac tggagcagtg cggctatccg     120
gtgcagcggc tggtcgccct ctacctggcg gcgcggctgt cgtggaacca ggtcgaccag     180
gtgatccgca acgccctggc cagccccggc agcggcggcg acctgggcga agcgatccgc     240
gagcagccgg agcaggcccg tctggccctg accctggccg ccgccgagag cgagcgcttc     300
gtccggcagg gcaccggcaa cgacgaggcc ggcgcggcca cgccgacgt ggtgagcctg      360 acctgcccgg tcgccgccgg tgaatgcgcg ggcccggcgg acagcggcga cgccctgctg     420
gagcgcaact atcccactgg cgcggagttc ctcggcgacg cgggcgacgt cagcttcagc     480
acccgcggca cgcagaactg gacggtggag cggctgctcc aggcgcaccg ccaactggag     540
gagcgcggct atgtgttcgt cggctaccac ggcaccttcc tcgaagcggc gaaagcatc      600 gtcttcggcg gggtgcgcgc gcgcagccag gacctcgacg cgatctggcg cggttctat     660 atcgccggcg atccggcgct ggcctacggc tacgcccagg accaggaacc cgacgcacgc    720
ggccggatcc gcaacggtgc cctgctgcgg gtctatgtgc cgcgctcgag cctgccgggc    780
ttctaccgca ccagcctgac cctggccgcg ccggaggcgg cgggcgaggt cgaacggctg    840
atcggccatc cgctgccgct gcgcctggac gccatcaccg gccccgagga ggaaggcggg    900
cgcctggaga ccattctcgg ctggccgctg gccgagcgca ccgtggtgat tcccctcggcg   960 atccccaccg acccgcgcaa cgtcggcggc gacctcgacc cgtccagcat cccccgacaag 1020
```

```
gaacaggcga tcagcgccct gccggactac gccagccagc ccggcaaacc gccgaaggac    1080
gagcta                                                                1086
```

<210> SEQ ID NO 66
<211> LENGTH: 362
<212> TYPE: PRT
<213> ORGANISM: Homo sapiens

<400> SEQUENCE: 66

```
Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Ala Asp Val Val Ser Leu Thr Cys Pro Val Ala Ala Gly Glu
        115                 120                 125

Cys Ala Gly Pro Ala Asp Ser Gly Asp Ala Leu Leu Glu Arg Asn Tyr
    130                 135                 140

Pro Thr Gly Ala Glu Phe Leu Gly Asp Gly Asp Val Ser Phe Ser
145                 150                 155                 160

Thr Arg Gly Thr Gln Asn Trp Thr Val Glu Arg Leu Leu Gln Ala His
                165                 170                 175

Arg Gln Leu Glu Glu Arg Gly Tyr Val Phe Val Gly Tyr His Gly Thr
            180                 185                 190

Phe Leu Glu Ala Ala Gln Ser Ile Val Phe Gly Gly Val Arg Ala Arg
        195                 200                 205

Ser Gln Asp Leu Asp Ala Ile Trp Arg Gly Phe Tyr Ile Ala Gly Asp
    210                 215                 220

Pro Ala Leu Ala Tyr Gly Tyr Ala Gln Asp Gln Glu Pro Asp Ala Arg
225                 230                 235                 240

Gly Arg Ile Arg Asn Gly Ala Leu Leu Arg Val Tyr Val Pro Arg Ser
                245                 250                 255

Ser Leu Pro Gly Phe Tyr Arg Thr Ser Leu Thr Leu Ala Ala Pro Glu
            260                 265                 270

Ala Ala Gly Glu Val Glu Arg Leu Ile Gly His Pro Leu Pro Leu Arg
        275                 280                 285

Leu Asp Ala Ile Thr Gly Pro Glu Glu Gly Gly Arg Leu Glu Thr
    290                 295                 300

Ile Leu Gly Trp Pro Leu Ala Glu Arg Thr Val Val Ile Pro Ser Ala
305                 310                 315                 320

Ile Pro Thr Asp Pro Arg Asn Val Gly Gly Asp Leu Asp Pro Ser Ser
                325                 330                 335

Ile Pro Asp Lys Glu Gln Ala Ile Ser Ala Leu Pro Asp Tyr Ala Ser
            340                 345                 350
```

Gln Pro Gly Lys Pro Pro Lys Asp Glu Leu
        355                 360

<210> SEQ ID NO 67
<211> LENGTH: 1107
<212> TYPE: DNA
<213> ORGANISM: Homo sapiens

<400> SEQUENCE: 67

| | | | | | |
|---|---|---|---|---|---|
| cccgagggcg | gcagcctggc | cgcgctgacc | gcgcaccagg | cttgccacct | gccgctggag | 60 |
| actttcaccc | gtcatcgcca | gccgcgcggc | tgggaacaac | tggagcagtg | cggctatccg | 120 |
| gtgcagcggc | tggtcgccct | ctacctggcg | gcgcggctgt | cgtggaacca | ggtcgaccag | 180 |
| gtgatcgcca | acgccctggc | cagccccggc | agcggcggcg | acctgggcga | agcgatccgc | 240 |
| gagtcgccgg | agcaggcccg | tctggccctg | accctggccg | ccgccgagag | cgagcgcttc | 300 |
| gtccggcagg | gcaccggcaa | cgacgaggcc | ggcgcggcca | acgccgacgt | ggtgagcctg | 360 |
| acctgccccg | tcgccgccgg | tgaatgcgcg | ggcccggcgg | acagcggcga | cgccctgctg | 420 |
| gagcgcaact | atcccactgg | cgcggagttc | ctcggcgacg | gcggcgacgt | cagcttcagc | 480 |
| acccgcggca | cgcagaactg | gacggtggag | cggctgctcc | aggcgcaccg | ccaactggag | 540 |
| gagggaggct | atgtgttcgt | cggctaccac | ggcaccttcc | tcgaagcggc | gcaaagcatc | 600 |
| gtcttcggcg | gggtgcgcgc | gcgcagccag | gacctgacg | cgatctgggc | cggtttctat | 660 |
| atcgccggcg | atccggcgct | ggcctacggc | tacgcccagg | accaggaacc | cgacgcagcc | 720 |
| ggccggatcc | gcaacggtgc | cctgctgcgg | gtctatgtgc | cgcgctcgag | cctgccgggc | 780 |
| ttctacgcca | ccagcctgac | cctggccgcg | ccggaggcgg | cgggcgaggt | cgaacggctg | 840 |
| atcggccatc | cgctgccgct | cgcgcctgac | gccatcaccg | gccccgagga | gtcaggcggg | 900 |
| cgcctggaga | ccattctcgg | ctggccgctg | gccgagcgca | ccgtggtgat | tccctcggcg | 960 |
| atccccaccg | acccgcgcaa | cgtcggcggc | gacctcgacc | cgtccagcat | ccccgactcg | 1020 |
| gaacaggcga | tcagcgccct | gccggactac | gccagccagc | ccggcaaacc | gccgaaggac | 1080 |
| gagctagaag | cttccggagg | tcccgag | | | | 1107 |

<210> SEQ ID NO 68
<211> LENGTH: 369
<212> TYPE: PRT
<213> ORGANISM: Homo sapiens

<400> SEQUENCE: 68

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Ala Asn
    50                  55                  60

Ala Leu Ala Ser Pro Gly Ser Gly Gly Asp Leu Gly Glu Ala Ile Arg
65                  70                  75                  80

Glu Ser Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Ala Asp Val Val Ser Leu Thr Cys Pro Val Ala Ala Gly Glu

```
            115                 120                 125
    Cys Ala Gly Pro Ala Asp Ser Gly Asp Ala Leu Leu Glu Arg Asn Tyr
        130                 135                 140

Pro Thr Gly Ala Glu Phe Leu Gly Asp Gly Asp Val Ser Phe Ser
    145                 150                 155                 160

Thr Arg Gly Thr Gln Asn Trp Thr Val Glu Arg Leu Leu Gln Ala His
                    165                 170                 175

Arg Gln Leu Glu Glu Gly Gly Tyr Val Phe Val Gly Tyr His Gly Thr
                180                 185                 190

Phe Leu Glu Ala Ala Gln Ser Ile Val Phe Gly Gly Val Arg Ala Arg
                    195                 200                 205

Ser Gln Asp Leu Asp Ala Ile Trp Ala Gly Phe Tyr Ile Ala Gly Asp
                210                 215                 220

Pro Ala Leu Ala Tyr Gly Tyr Ala Gln Asp Gln Glu Pro Asp Ala Ala
    225                 230                 235                 240

Gly Arg Ile Arg Asn Gly Ala Leu Leu Arg Val Tyr Val Pro Arg Ser
                    245                 250                 255

Ser Leu Pro Gly Phe Tyr Ala Thr Ser Leu Thr Leu Ala Ala Pro Glu
                260                 265                 270

Ala Ala Gly Glu Val Glu Arg Leu Ile Gly His Pro Leu Pro Leu Arg
                275                 280                 285

Leu Asp Ala Ile Thr Gly Pro Glu Glu Ser Gly Gly Arg Leu Glu Thr
                290                 295                 300

Ile Leu Gly Trp Pro Leu Ala Glu Arg Thr Val Val Ile Pro Ser Ala
    305                 310                 315                 320

Ile Pro Thr Asp Pro Arg Asn Val Gly Gly Asp Leu Asp Pro Ser Ser
                    325                 330                 335

Ile Pro Asp Ser Glu Gln Ala Ile Ser Ala Leu Pro Asp Tyr Ala Ser
                340                 345                 350

Gln Pro Gly Lys Pro Pro Lys Asp Glu Leu Glu Ala Ser Gly Gly Pro
                355                 360                 365

Glu

<210> SEQ ID NO 69
    <211> LENGTH: 18
    <212> TYPE: PRT
    <213> ORGANISM: artificial
    <220> FEATURE:
    <223> OTHER INFORMATION: ARL linker

<400> SEQUENCE: 69

Gly Ser Thr Ser Gly Ser Gly Lys Pro Gly Ser Gly Glu Gly Ser Thr
    1               5                   10                  15

Lys Gly

<210> SEQ ID NO 70
    <211> LENGTH: 4
    <212> TYPE: PRT
    <213> ORGANISM: artificial
    <220> FEATURE:
    <223> OTHER INFORMATION: endoplasmic reticulum retention sequence

<400> SEQUENCE: 70

Lys Asp Glu Leu
    1

<210> SEQ ID NO 71
```

```
<211> LENGTH: 5
<212> TYPE: PRT
<213> ORGANISM: artificial
<220> FEATURE:
<223> OTHER INFORMATION: G4S linker

<400> SEQUENCE: 71

Gly Gly Gly Gly Ser
1               5

<210> SEQ ID NO 72
<211> LENGTH: 7
<212> TYPE: PRT
<213> ORGANISM: artificial
<220> FEATURE:
<223> OTHER INFORMATION: seven amino acid linker

<400> SEQUENCE: 72

Glu Ala Ser Gly Gly Pro Glu
1               5

<210> SEQ ID NO 73
<211> LENGTH: 5
<212> TYPE: PRT
<213> ORGANISM: artificial
<220> FEATURE:
<223> OTHER INFORMATION: C-terminal of PE38

<400> SEQUENCE: 73

Arg Glu Asp Leu Lys
1               5

<210> SEQ ID NO 74
<211> LENGTH: 18
<212> TYPE: PRT
<213> ORGANISM: artificial
<220> FEATURE:
<223> OTHER INFORMATION: linker peptide

<400> SEQUENCE: 74

Ser Ser Gly Gly Gly Gly Ser Gly Gly Gly Gly Gly Gly Ser Ser Arg
1               5                   10                  15

Ser Ser
```